(12) United States Patent
Shelton, IV et al.

(10) Patent No.: US 11,775,682 B2
(45) Date of Patent: Oct. 3, 2023

(54) DATA STRIPPING METHOD TO INTERROGATE PATIENT RECORDS AND CREATE ANONYMIZED RECORD

(71) Applicant: Cilag GmbH International, Zug (CH)

(72) Inventors: Frederick E. Shelton, IV, Hillsboro, OH (US); Jason L. Harris, Lebanon, OH (US); David C. Yates, Morrow, OH (US)

(73) Assignee: Cilag GmbH International, Zug (CH)

( * ) Notice: Subject to any disclaimer, the term of this patent is extended or adjusted under 35 U.S.C. 154(b) by 1 day.

(21) Appl. No.: 17/217,163

(22) Filed: Mar. 30, 2021

(65) Prior Publication Data

US 2021/0240852 A1  Aug. 5, 2021

Related U.S. Application Data

(63) Continuation of application No. 15/940,632, filed on Mar. 29, 2018, now Pat. No. 11,132,462.

(60) Provisional application No. 62/649,294, filed on Mar. 28, 2018, provisional application No. 62/611,341, filed on Dec. 28, 2017, provisional application No. 62/611,340, filed on Dec. 28, 2017, provisional application No. 62/611,339, filed on Dec. 28, 2017.

(51) Int. Cl.
*G06F 21/62* (2013.01)
*G16H 50/70* (2018.01)
*G16H 10/60* (2018.01)

(52) U.S. Cl.
CPC ......... *G06F 21/6254* (2013.01); *G16H 10/60* (2018.01); *G16H 50/70* (2018.01)

(58) Field of Classification Search
None
See application file for complete search history.

(56) References Cited

U.S. PATENT DOCUMENTS 1,853,416 A    4/1932   Hall
2,222,125 A    11/1940  Stehlik
(Continued)

FOREIGN PATENT DOCUMENTS

AU    2015201140 A1    3/2015
CA       2795323 A1    5/2014
(Continued)

OTHER PUBLICATIONS

US 10,504,709, 8/2018, Karancsi et al. (withdrawn)
(Continued)

*Primary Examiner* — Benjamin E Lanier

(57) ABSTRACT

Various surgical hubs and data stripping methods are disclosed. The surgical hub comprises a processor and a memory coupled to the processor. The memory stores instructions executable by the processor to interrogate a modular device coupled to the processor via a modular communication hub. The modular device is a source of data sets that include patient identity data and surgical procedure data. The processor also executes instructions to: receive a data set from the modular device; discard the patient identity data and any portion of the surgical procedure data that identifies the patient from the data set; extract anonymous data from the data set and create an anonymized data set; and configure operation of the surgical hub or the modular device based on the anonymized data set.

18 Claims, 37 Drawing Sheets

(56) References Cited

U.S. PATENT DOCUMENTS

| | | | |
|---|---|---|---|
| 3,082,426 A | 3/1963 | Miles | |
| 3,503,396 A | 3/1970 | Pierie et al. | |
| 3,584,628 A | 6/1971 | Green | |
| 3,626,457 A | 12/1971 | Duerr et al. | |
| 3,633,584 A | 1/1972 | Farrell | |
| 3,759,017 A | 9/1973 | Young | |
| 3,863,118 A | 1/1975 | Lander et al. | |
| 3,898,545 A | 8/1975 | Coppa et al. | |
| 3,912,121 A | 10/1975 | Steffen | |
| 3,915,271 A | 10/1975 | Harper | |
| 3,932,812 A | 1/1976 | Milligan | |
| 4,041,362 A | 8/1977 | Ichiyanagi | |
| 4,052,649 A | 10/1977 | Greenwell et al. | |
| 4,087,730 A | 5/1978 | Goles | |
| 4,157,859 A | 6/1979 | Terry | |
| 4,171,700 A | 10/1979 | Farin | |
| 4,202,722 A | 5/1980 | Paquin | |
| 4,412,539 A | 11/1983 | Jarvik | |
| 4,448,193 A | 5/1984 | Ivanov | |
| 4,523,695 A | 6/1985 | Braun et al. | |
| 4,608,160 A | 8/1986 | Zoch | |
| 4,614,366 A | 9/1986 | North et al. | |
| 4,633,874 A | 1/1987 | Chow et al. | |
| 4,701,193 A | 10/1987 | Robertson et al. | |
| 4,735,603 A | 4/1988 | Goodson et al. | |
| 4,788,977 A | 12/1988 | Farin et al. | |
| 4,827,911 A | 5/1989 | Broadwin et al. | |
| 4,849,752 A | 7/1989 | Bryant | |
| D303,787 S | 10/1989 | Messenger et al. | |
| 4,892,244 A | 1/1990 | Fox et al. | |
| 4,976,173 A | 12/1990 | Yang | |
| 5,010,341 A | 4/1991 | Huntley et al. | |
| 5,026,387 A | 6/1991 | Thomas | |
| 5,035,692 A | 7/1991 | Lyon et al. | |
| 5,042,460 A | 8/1991 | Sakurai et al. | |
| 5,047,043 A | 9/1991 | Kubota et al. | |
| 5,084,057 A | 1/1992 | Green et al. | |
| 5,100,402 A | 3/1992 | Fan | |
| D327,061 S | 6/1992 | Soren et al. | |
| 5,129,570 A | 7/1992 | Schulze et al. | |
| 5,151,102 A | 9/1992 | Kamiyama et al. | |
| 5,156,315 A | 10/1992 | Green et al. | |
| 5,158,585 A | 10/1992 | Saho et al. | |
| 5,171,247 A | 12/1992 | Hughett et al. | |
| 5,189,277 A | 2/1993 | Boisvert et al. | |
| 5,197,962 A | 3/1993 | Sansom et al. | |
| 5,204,669 A | 4/1993 | Dorfe et al. | |
| 5,217,003 A | 6/1993 | Wilk | |
| 5,242,474 A | 9/1993 | Herbst et al. | |
| 5,253,793 A | 10/1993 | Green et al. | |
| 5,271,543 A | 12/1993 | Grant et al. | |
| RE34,519 E | 1/1994 | Fox et al. | |
| 5,275,323 A | 1/1994 | Schulze et al. | |
| 5,318,516 A | 6/1994 | Cosmescu | |
| 5,318,563 A | 6/1994 | Malis et al. | |
| 5,322,055 A | 6/1994 | Davison et al. | |
| 5,342,349 A | 8/1994 | Kaufman | |
| 5,364,003 A | 11/1994 | Williamson, IV | |
| 5,383,880 A | 1/1995 | Hooven | |
| 5,385,544 A | 1/1995 | Edwards et al. | |
| 5,391,144 A | 2/1995 | Sakurai et al. | |
| 5,396,900 A | 3/1995 | Slater et al. | |
| 5,397,046 A | 3/1995 | Savage et al. | |
| 5,403,312 A | 4/1995 | Yates et al. | |
| 5,403,327 A | 4/1995 | Thornton et al. | |
| 5,413,267 A | 5/1995 | Solyntjes et al. | |
| 5,415,335 A | 5/1995 | Knodell, Jr. | |
| 5,417,699 A | 5/1995 | Klein et al. | |
| 5,439,468 A | 8/1995 | Schulze et al. | |
| 5,445,304 A | 8/1995 | Plyley et al. | |
| 5,462,545 A | 10/1995 | Wang et al. | |
| 5,465,895 A | 11/1995 | Knodel et al. | |
| 5,467,911 A | 11/1995 | Tsuruta et al. | |
| 5,474,566 A | 12/1995 | Alesi et al. | |
| 5,485,947 A | 1/1996 | Olson et al. | |
| 5,496,315 A | 3/1996 | Weaver et al. | |
| 5,496,317 A | 3/1996 | Goble et al. | |
| 5,503,320 A | 4/1996 | Webster et al. | |
| 5,507,773 A | 4/1996 | Huitema et al. | |
| 5,529,235 A | 6/1996 | Boiarski et al. | |
| 5,531,743 A | 7/1996 | Nettekoven et al. | |
| 5,545,148 A | 8/1996 | Wurster | |
| 5,552,685 A | 9/1996 | Young et al. | |
| 5,560,372 A | 10/1996 | Cory | |
| 5,584,425 A | 12/1996 | Savage et al. | |
| 5,610,379 A | 3/1997 | Muz et al. | |
| 5,610,811 A | 3/1997 | Honda | |
| 5,613,966 A | 3/1997 | Makower et al. | |
| 5,624,452 A | 4/1997 | Yates | |
| D379,346 S | 5/1997 | Mieki | |
| 5,626,587 A | 5/1997 | Bishop et al. | |
| 5,643,291 A | 7/1997 | Pier et al. | |
| 5,654,750 A | 8/1997 | Weil et al. | |
| 5,673,841 A | 10/1997 | Schulze et al. | |
| 5,673,842 A | 10/1997 | Bittner et al. | |
| 5,675,227 A | 10/1997 | Roos et al. | |
| 5,693,042 A | 12/1997 | Boiarski et al. | |
| 5,693,052 A | 12/1997 | Weaver | |
| 5,695,502 A | 12/1997 | Pier et al. | |
| 5,697,926 A | 12/1997 | Weaver | |
| 5,706,998 A | 1/1998 | Plyley et al. | |
| 5,718,359 A | 2/1998 | Palmer et al. | |
| 5,724,468 A | 3/1998 | Leone et al. | |
| 5,725,536 A | 3/1998 | Oberlin et al. | |
| 5,725,542 A | 3/1998 | Yoon | |
| 5,735,445 A | 4/1998 | Vidal et al. | |
| 5,735,848 A | 4/1998 | Yates et al. | |
| 5,746,209 A | 5/1998 | Yost et al. | |
| 5,749,362 A | 5/1998 | Funda et al. | |
| 5,749,893 A | 5/1998 | Vidal et al. | |
| 5,752,644 A | 5/1998 | Bolanos et al. | |
| 5,762,255 A | 6/1998 | Chrisman et al. | |
| 5,762,458 A | 6/1998 | Wang et al. | |
| 5,766,186 A | 6/1998 | Faraz et al. | |
| 5,769,791 A | 6/1998 | Benaron et al. | |
| 5,775,331 A | 7/1998 | Raymond et al. | |
| 5,796,188 A | 8/1998 | Bays | |
| 5,797,537 A | 8/1998 | Oberlin et al. | |
| 5,800,350 A | 9/1998 | Coppleson et al. | |
| D399,561 S | 10/1998 | Ellingson | |
| 5,817,093 A | 10/1998 | Williamson, IV et al. | |
| 5,820,009 A | 10/1998 | Melling et al. | |
| 5,833,690 A | 11/1998 | Yates et al. | |
| 5,836,849 A | 11/1998 | Mathiak et al. | |
| 5,836,869 A | 11/1998 | Kudo et al. | |
| 5,836,909 A | 11/1998 | Cosmescu | |
| 5,843,080 A | 12/1998 | Fleenor et al. | |
| 5,846,237 A | 12/1998 | Nettekoven | |
| 5,849,022 A | 12/1998 | Sakashita et al. | |
| 5,873,873 A | 2/1999 | Smith et al. | |
| 5,878,938 A | 3/1999 | Bittner et al. | |
| 5,893,849 A | 4/1999 | Weaver | |
| 5,906,625 A | 5/1999 | Bito et al. | |
| 5,942,333 A | 8/1999 | Arnett et al. | |
| 5,947,996 A | 9/1999 | Logeman | |
| 5,968,032 A | 10/1999 | Sleister | |
| 5,980,510 A | 11/1999 | Tsonton et al. | |
| 5,987,346 A | 11/1999 | Benaron et al. | |
| 5,997,528 A | 12/1999 | Bisch et al. | |
| 6,004,269 A | 12/1999 | Crowley et al. | |
| 6,010,054 A | 1/2000 | Johnson et al. | |
| 6,030,437 A | 2/2000 | Gourrier et al. | |
| 6,036,637 A | 3/2000 | Kudo | |
| 6,039,734 A | 3/2000 | Goble | |
| 6,039,735 A | 3/2000 | Greep | |
| 6,059,799 A | 5/2000 | Aranyi et al. | |
| 6,066,137 A | 5/2000 | Greep | |
| 6,079,606 A | 6/2000 | Milliman et al. | |
| 6,090,107 A | 7/2000 | Borgmeier et al. | |
| 6,099,537 A | 8/2000 | Sugai et al. | |
| 6,102,907 A | 8/2000 | Smethers et al. | |
| 6,109,500 A | 8/2000 | Alli et al. | |
| 6,113,598 A | 9/2000 | Baker | |
| 6,126,592 A | 10/2000 | Proch et al. | |

(56) References Cited

U.S. PATENT DOCUMENTS

| | | |
|---|---|---|
| 6,126,658 A | 10/2000 | Baker |
| 6,131,789 A | 10/2000 | Schulze et al. |
| 6,139,561 A | 10/2000 | Shibata et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,482,217 B1 | 11/2002 | Pintor et al. |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,695,199 B2 | 2/2004 | Whitman |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,071 B2 | 2/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,094,231 B1 | 8/2006 | Ellman et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,413,541 B2 | 8/2008 | Konishi |
| 7,422,136 B1 | 9/2008 | Marczyk |
| 7,422,139 B2 | 9/2008 | Shelton, IV et al. |
| 7,422,586 B2 | 9/2008 | Morris et al. |
| 7,423,972 B2 | 9/2008 | Shaham et al. |
| D579,876 S | 11/2008 | Novotney et al. |
| 7,445,620 B2 | 11/2008 | Kefer |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |

(56) References Cited

U.S. PATENT DOCUMENTS

| | | |
|---|---|---|
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,772 B2 | 4/2010 | Pauker et al. |
| 7,699,860 B2 | 4/2010 | Huitema et al. |
| 7,717,312 B2 | 5/2010 | Beetel |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,722,603 B2 | 5/2010 | McPherson |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,950,560 B2 | 5/2011 | Zemlok et al. |
| 7,951,148 B2 | 5/2011 | McClurken |
| 7,954,682 B2 | 6/2011 | Giordano et al. |
| 7,954,687 B2 | 6/2011 | Zemlok et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,993,354 B1 | 8/2011 | Brecher et al. |
| 7,993,954 B2 | 8/2011 | Wieting |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,095,327 B2 | 1/2012 | Tahara et al. |
| 8,096,459 B2 | 1/2012 | Ortiz et al. |
| 8,116,848 B2 | 2/2012 | Shahidi |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| 8,146,149 B2 | 3/2012 | Steinkogler et al. |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,241,322 B2 | 8/2012 | Whitman et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |

(56) References Cited

U.S. PATENT DOCUMENTS

| | | |
|---|---|---|
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |
| 8,453,906 B2 | 6/2013 | Huang et al. |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,473,066 B2 | 6/2013 | Aghassian et al. |
| D687,146 S | 7/2013 | Juzkiw et al. |
| 8,476,227 B2 | 7/2013 | Kaplan et al. |
| 8,478,418 B2 | 7/2013 | Fahey |
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,533,475 B2 | 9/2013 | Frikart et al. |
| 8,540,709 B2 | 9/2013 | Allen |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,568,411 B2 | 10/2013 | Falkenstein et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,617,155 B2 | 12/2013 | Johnson et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,663,222 B2 | 3/2014 | Anderson et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| 8,708,213 B2 | 4/2014 | Shelton, IV et al. |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,607 B2 | 9/2014 | Marczyk |
| 8,820,608 B2 | 9/2014 | Miyamoto |
| 8,827,134 B2 | 9/2014 | Viola et al. |
| 8,827,136 B2 | 9/2014 | Hessler |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,864,747 B2 | 10/2014 | Merchant et al. |
| 8,875,973 B2 | 11/2014 | Whitman |
| 8,876,857 B2 | 11/2014 | Burbank |
| 8,882,662 B2 | 11/2014 | Charles |
| 8,885,032 B2 | 11/2014 | Igarashi et al. |
| 8,886,790 B2 | 11/2014 | Harrang et al. |
| 8,893,946 B2 | 11/2014 | Boudreaux et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,934,684 B2 | 1/2015 | Mohamed |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |

(56) References Cited

U.S. PATENT DOCUMENTS

| | | |
|---|---|---|
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,023,079 B2 | 5/2015 | Boulnois et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,131,957 B2 | 9/2015 | Skarbnik et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,141,758 B2 | 9/2015 | Kress et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,198,835 B2 | 12/2015 | Swisher et al. |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,259,282 B2 | 2/2016 | Azizian et al. |
| 9,265,429 B2 | 2/2016 | St. Pierre et al. |
| 9,265,585 B2 | 2/2016 | Wingardner et al. |
| 9,265,959 B2 | 2/2016 | Drew et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,299,138 B2 | 3/2016 | Zellner et al. |
| 9,301,691 B2 | 4/2016 | Hufnagel et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch, Jr. et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |

(56) References Cited

U.S. PATENT DOCUMENTS

| | | |
|---|---|---|
| 9,341,704 B2 | 5/2016 | Picard et al. |
| 9,345,481 B2 | 5/2016 | Hall et al. |
| 9,345,490 B2 | 5/2016 | Ippisch |
| 9,345,544 B2 | 5/2016 | Hourtash et al. |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Durie |
| 9,364,200 B2 | 6/2016 | Whitman et al. |
| 9,364,230 B2 | 6/2016 | Shelton, IV et al. |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,404,868 B2 | 8/2016 | Yamanaka et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,219 B2 | 11/2016 | Moore et al. |
| 9,498,231 B2 | 11/2016 | Haider et al. |
| 9,498,291 B2 | 11/2016 | Balaji et al. |
| 9,509,566 B2 | 11/2016 | Chu et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,580 B2 | 12/2016 | Humayun et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,545,216 B2 | 1/2017 | D'Angelo et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,585,658 B2 | 3/2017 | Shelton, IV |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| 9,603,609 B2 | 3/2017 | Kawashima et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,096 B1 | 5/2017 | Heaton, II et al. |
| 9,636,112 B2 | 5/2017 | Penna et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,614 B2 | 5/2017 | Swensgard et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |

(56) References Cited

U.S. PATENT DOCUMENTS

| | | |
|---|---|---|
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,737,371 B2 | 8/2017 | Romo et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,560 B2 | 9/2017 | Ballakur et al. |
| 9,750,563 B2 | 9/2017 | Shikhman et al. |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,467 B2 | 12/2017 | Harper et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach et al. |
| 9,888,864 B2 | 2/2018 | Rondoni et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,943,964 B2 | 4/2018 | Hares |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |

(56) References Cited

U.S. PATENT DOCUMENTS

| | | |
|---|---|---|
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter, III et al. |
| 10,117,651 B2 | 11/2018 | Whitman et al. |
| 10,117,702 B2 | 11/2018 | Danziger et al. |
| 10,118,119 B2 | 11/2018 | Sappok |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,130,373 B2 | 11/2018 | Castro et al. |
| 10,130,432 B2 | 11/2018 | Auld et al. |
| 10,133,248 B2 | 11/2018 | Fitzsimmons et al. |
| 10,135,242 B2 | 11/2018 | Baber et al. |
| 10,136,246 B2 | 11/2018 | Yamada |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonifas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1* | 2/2019 | Fletcher ............. G06F 21/6245 |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,245,040 B2 | 4/2019 | Milliman |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |

(56) References Cited

U.S. PATENT DOCUMENTS

| | | |
|---|---|---|
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,610 B2 | 5/2019 | Srivastava |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,868 B2 | 5/2019 | Tsuboi et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,042 B2 | 7/2019 | Schoenle et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,344 B2 | 10/2019 | Notz et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,684 B2 | 11/2019 | Toth et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,507,278 B2 | 12/2019 | Gao et al. |
| 10,510,267 B2 | 12/2019 | Jarc et al. |
| 10,512,413 B2 | 12/2019 | Schepis et al. |
| 10,512,461 B2 | 12/2019 | Gupta et al. |
| 10,512,499 B2 | 12/2019 | McHenry et al. |
| 10,512,509 B2 | 12/2019 | Bowling et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |

(56) References Cited

U.S. PATENT DOCUMENTS

| | | |
|---|---|---|
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,537,396 B2 | 1/2020 | Zingaretti et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,349 B2 | 2/2020 | Wedekind et al. |
| 10,561,422 B2 | 2/2020 | Schellin et al. |
| 10,561,470 B2 | 2/2020 | Hourtash et al. |
| 10,561,471 B2 | 2/2020 | Nichogi |
| 10,561,560 B2 | 2/2020 | Boutoussov et al. |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savaii et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,962 B2 | 3/2020 | Friedrichs et al. |
| 10,582,964 B2 | 3/2020 | Weinberg et al. |
| 10,586,074 B2 * | 3/2020 | Rose .................. G06F 21/6254 |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,100 B2 | 6/2020 | Frushour |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,498 B2 | 8/2020 | Watanabe et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,673 B2 | 9/2020 | Allen, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |

(56) References Cited

U.S. PATENT DOCUMENTS

| | | |
|---|---|---|
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,806,445 B2 | 10/2020 | Penna et al. |
| 10,806,453 B2 | 10/2020 | Chen et al. |
| 10,806,454 B2 | 10/2020 | Kopp |
| 10,806,499 B2 | 10/2020 | Castaneda et al. |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,828,028 B2 | 11/2020 | Harris et al. |
| 10,828,030 B2 | 11/2020 | Weir et al. |
| 10,835,206 B2 | 11/2020 | Bell et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| D904,612 S | 12/2020 | Wynn et al. |
| 10,849,697 B2 | 12/2020 | Yates et al. |
| 10,849,700 B2 | 12/2020 | Kopp et al. |
| 10,856,768 B2 | 12/2020 | Osadchy et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,888,321 B2 | 1/2021 | Shelton, IV et al. |
| 10,888,322 B2 | 1/2021 | Morgan et al. |
| 10,892,899 B2 | 1/2021 | Shelton, IV et al. |
| 10,892,995 B2 | 1/2021 | Shelton, IV et al. |
| 10,893,863 B2 | 1/2021 | Shelton, IV et al. |
| 10,893,864 B2 | 1/2021 | Harris et al. |
| 10,893,884 B2 | 1/2021 | Stoddard et al. |
| 10,898,105 B2 | 1/2021 | Weprin et al. |
| 10,898,183 B2 | 1/2021 | Shelton, IV et al. |
| 10,898,186 B2 | 1/2021 | Bakos et al. |
| 10,898,189 B2 | 1/2021 | McDonald, II |
| 10,898,256 B2 | 1/2021 | Yates et al. |
| 10,898,280 B2 | 1/2021 | Kopp |
| 10,898,622 B2 | 1/2021 | Shelton, IV et al. |
| 10,902,944 B1 | 1/2021 | Casey et al. |
| 10,903,685 B2 | 1/2021 | Yates et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,912,559 B2 | 2/2021 | Harris et al. |
| 10,912,567 B2 | 2/2021 | Shelton, IV et al. |
| 10,912,580 B2 | 2/2021 | Green et al. |
| 10,912,619 B2 | 2/2021 | Jarc et al. |
| 10,916,415 B2 | 2/2021 | Karancsi et al. |
| 10,918,385 B2 | 2/2021 | Overmyer et al. |
| 10,930,400 B2 | 2/2021 | Robbins et al. |
| D914,878 S | 3/2021 | Shelton, IV et al. |
| 10,932,705 B2 | 3/2021 | Muhsin et al. |
| 10,932,772 B2 | 3/2021 | Shelton, IV et al. |
| 10,932,784 B2 | 3/2021 | Mozdzierz et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,939,313 B2 | 3/2021 | Eom et al. |
| 10,943,454 B2 | 3/2021 | Shelton, IV et al. |
| 10,944,728 B2 | 3/2021 | Wiener et al. |
| 10,945,727 B2 | 3/2021 | Shelton, IV et al. |
| 10,950,982 B2 | 3/2021 | Regnier et al. |
| 10,952,708 B2 | 3/2021 | Scheib et al. |
| 10,952,732 B2 | 3/2021 | Binmoeller et al. |
| 10,954,935 B2 | 3/2021 | O'Shea et al. |
| 10,959,727 B2 | 3/2021 | Hunter et al. |
| 10,959,729 B2 | 3/2021 | Ehrenfels et al. |
| 10,959,744 B2 | 3/2021 | Shelton, IV et al. |
| 10,959,788 B2 | 3/2021 | Grover et al. |
| 10,960,150 B2 | 3/2021 | Zergiebel et al. |
| 10,962,449 B2 | 3/2021 | Unuma et al. |
| 10,966,590 B2 | 4/2021 | Takahashi et al. |
| 10,966,791 B2 | 4/2021 | Harris et al. |
| 10,966,798 B2 | 4/2021 | Tesar et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,973,682 B2 | 4/2021 | Vezzu et al. |
| 10,980,536 B2 | 4/2021 | Weaner et al. |
| 10,980,537 B2 | 4/2021 | Shelton, IV et al. |
| 10,980,560 B2 | 4/2021 | Shelton, IV et al. |
| 10,980,595 B2 | 4/2021 | Wham |
| 10,980,610 B2 | 4/2021 | Rosenberg et al. |
| 10,987,102 B2 | 4/2021 | Gonzalez et al. |
| 10,987,178 B2 | 4/2021 | Shelton, IV et al. |
| 10,992,698 B2 | 4/2021 | Patel et al. |
| 10,993,715 B2 | 5/2021 | Shelton, IV et al. |
| 10,998,098 B2 | 5/2021 | Greene et al. |
| 11,000,276 B2 | 5/2021 | Shelton, IV et al. |
| 11,000,278 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,563 B2 | 5/2021 | Shelton, IV et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,045,197 B2 | 6/2021 | Shelton, IV et al. |
| 11,045,591 B2 | 6/2021 | Shelton, IV et al. |
| 11,051,817 B2 | 7/2021 | Shelton, IV et al. |
| 11,051,836 B2 | 7/2021 | Shelton, IV et al. |
| 11,051,873 B2 | 7/2021 | Wiener et al. |
| 11,051,876 B2 | 7/2021 | Shelton, IV et al. |
| 11,051,902 B2 | 7/2021 | Kruecker et al. |
| 11,056,244 B2 | 7/2021 | Shelton, IV et al. |
| 11,058,423 B2 | 7/2021 | Shelton, IV et al. |
| 11,058,498 B2 | 7/2021 | Shelton, IV et al. |
| 11,058,501 B2 | 7/2021 | Tokarchuk et al. |
| 11,064,997 B2 | 7/2021 | Shelton, IV et al. |
| 11,069,012 B2 | 7/2021 | Shelton, IV et al. |
| 11,071,560 B2 | 7/2021 | Deck et al. |
| 11,071,595 B2 | 7/2021 | Johnson et al. |
| 11,076,921 B2 | 8/2021 | Shelton, IV et al. |
| 11,083,458 B2 | 8/2021 | Harris et al. |
| 11,090,047 B2 | 8/2021 | Shelton, IV et al. |
| 11,090,048 B2 | 8/2021 | Fanelli et al. |
| 11,090,075 B2 | 8/2021 | Hunter et al. |
| 11,096,688 B2 | 8/2021 | Shelton, IV et al. |
| 11,096,693 B2 | 8/2021 | Shelton, IV et al. |
| 11,100,631 B2 | 8/2021 | Yates et al. |
| 11,103,268 B2 | 8/2021 | Shelton, IV et al. |
| 11,109,866 B2 | 9/2021 | Shelton, IV et al. |
| 11,109,878 B2 | 9/2021 | Shelton, IV et al. |
| 11,114,195 B2 | 9/2021 | Shelton, IV et al. |
| 11,116,485 B2 | 9/2021 | Scheib et al. |
| 11,123,070 B2 | 9/2021 | Shelton, IV et al. |
| 11,129,611 B2 | 9/2021 | Shelton, IV et al. |
| 11,129,634 B2 | 9/2021 | Scheib et al. |

(56) References Cited

U.S. PATENT DOCUMENTS

| | | |
|---|---|---|
| 11,129,636 B2 | 9/2021 | Shelton, IV et al. |
| 11,129,669 B2 | 9/2021 | Stulen et al. |
| 11,129,670 B2 | 9/2021 | Shelton, IV et al. |
| 11,132,462 B2 * | 9/2021 | Shelton, IV .......... G06F 21/6254 |
| 11,134,942 B2 | 10/2021 | Harris et al. |
| 11,141,160 B2 | 10/2021 | Shelton, IV et al. |
| 11,141,213 B2 | 10/2021 | Yates et al. |
| 11,147,607 B2 | 10/2021 | Yates et al. |
| 11,160,551 B2 | 11/2021 | Shelton, IV et al. |
| 11,160,605 B2 | 11/2021 | Shelton, IV et al. |
| 11,166,716 B2 | 11/2021 | Shelton, IV et al. |
| 11,166,772 B2 | 11/2021 | Shelton, IV et al. |
| 11,179,150 B2 | 11/2021 | Yates et al. |
| 11,179,151 B2 | 11/2021 | Shelton, IV et al. |
| 11,179,155 B2 | 11/2021 | Shelton, IV et al. |
| 11,179,175 B2 | 11/2021 | Houser et al. |
| 11,179,204 B2 | 11/2021 | Shelton, IV et al. |
| 11,179,208 B2 | 11/2021 | Yates et al. |
| 11,185,325 B2 | 11/2021 | Shelton, IV et al. |
| 11,185,330 B2 | 11/2021 | Huitema et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,570 B2 | 12/2021 | Shelton, IV et al. |
| 11,207,065 B2 | 12/2021 | Harris et al. |
| 11,207,067 B2 | 12/2021 | Shelton, IV et al. |
| 11,207,090 B2 | 12/2021 | Shelton, IV et al. |
| 11,213,293 B2 | 1/2022 | Worthington et al. |
| 11,213,294 B2 | 1/2022 | Shelton, IV et al. |
| 11,213,359 B2 | 1/2022 | Shelton, IV et al. |
| 11,218,822 B2 | 1/2022 | Morgan et al. |
| 11,219,453 B2 | 1/2022 | Shelton, IV et al. |
| 11,224,426 B2 | 1/2022 | Shelton, IV et al. |
| 11,229,436 B2 | 1/2022 | Shelton, IV et al. |
| 11,229,471 B2 | 1/2022 | Shelton, IV et al. |
| 11,234,756 B2 | 2/2022 | Shelton, IV et al. |
| 11,241,230 B2 | 2/2022 | Shelton, IV et al. |
| 11,253,256 B2 | 2/2022 | Harris et al. |
| 11,253,315 B2 | 2/2022 | Yates et al. |
| 11,257,589 B2 | 2/2022 | Shelton, IV et al. |
| 11,259,806 B2 | 3/2022 | Shelton, IV et al. |
| 11,259,807 B2 | 3/2022 | Shelton, IV et al. |
| 11,259,830 B2 | 3/2022 | Nott et al. |
| 11,266,409 B2 | 3/2022 | Huitema et al. |
| 11,266,468 B2 | 3/2022 | Shelton, IV et al. |
| 11,272,931 B2 | 3/2022 | Boudreaux et al. |
| 11,273,001 B2 | 3/2022 | Shelton, IV et al. |
| 11,273,290 B2 | 3/2022 | Kowshik |
| 11,278,280 B2 | 3/2022 | Shelton, IV et al. |
| 11,278,281 B2 | 3/2022 | Shelton, IV et al. |
| 11,284,890 B2 | 3/2022 | Nalagatla et al. |
| 11,284,936 B2 | 3/2022 | Shelton, IV et al. |
| 11,291,440 B2 | 4/2022 | Harris et al. |
| 11,291,441 B2 | 4/2022 | Giordano et al. |
| 11,291,444 B2 | 4/2022 | Boudreaux et al. |
| 11,291,445 B2 | 4/2022 | Shelton, IV et al. |
| 11,291,465 B2 | 4/2022 | Parihar et al. |
| 11,291,495 B2 | 4/2022 | Yates et al. |
| 11,291,510 B2 | 4/2022 | Shelton, IV et al. |
| 11,298,128 B2 | 4/2022 | Messerly et al. |
| 11,298,129 B2 | 4/2022 | Bakos et al. |
| 11,298,130 B2 | 4/2022 | Bakos et al. |
| 11,298,148 B2 | 4/2022 | Jayme et al. |
| 11,304,699 B2 | 4/2022 | Shelton, IV et al. |
| 11,304,720 B2 | 4/2022 | Kimball et al. |
| 11,304,745 B2 | 4/2022 | Shelton, IV et al. |
| 11,304,763 B2 | 4/2022 | Shelton, IV et al. |
| 11,308,075 B2 | 4/2022 | Shelton, IV et al. |
| 11,311,306 B2 | 4/2022 | Shelton, IV et al. |
| 11,311,342 B2 | 4/2022 | Parihar et al. |
| D950,728 S | 5/2022 | Bakos et al. |
| D952,144 S | 5/2022 | Boudreaux |
| 11,317,915 B2 | 5/2022 | Boudreaux et al. |
| 11,317,919 B2 | 5/2022 | Shelton, IV et al. |
| 11,317,937 B2 | 5/2022 | Nott et al. |
| 11,322,248 B2 | 5/2022 | Grantcharov et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,337,746 B2 | 5/2022 | Boudreaux |
| 11,344,326 B2 | 5/2022 | Faller et al. |
| 11,350,932 B2 | 6/2022 | Shelton, IV et al. |
| 11,350,959 B2 | 6/2022 | Messerly et al. |
| 11,350,978 B2 | 6/2022 | Henderson et al. |
| 11,357,503 B2 | 6/2022 | Bakos et al. |
| 11,364,075 B2 | 6/2022 | Yates et al. |
| 11,369,377 B2 | 6/2022 | Boudreaux et al. |
| 11,373,755 B2 | 6/2022 | Shelton, IV et al. |
| 11,376,002 B2 | 7/2022 | Shelton, IV et al. |
| 11,376,098 B2 | 7/2022 | Shelton, IV et al. |
| 11,382,697 B2 | 7/2022 | Shelton, IV et al. |
| 11,382,715 B2 | 7/2022 | Arai et al. |
| 11,389,164 B2 | 7/2022 | Yates et al. |
| 11,389,188 B2 | 7/2022 | Gee et al. |
| 11,399,858 B2 | 8/2022 | Sawhney et al. |
| 11,406,382 B2 | 8/2022 | Shelton, IV et al. |
| 11,406,390 B2 | 8/2022 | Shelton, IV et al. |
| 11,410,259 B2 | 8/2022 | Harris et al. |
| 11,413,042 B2 | 8/2022 | Shelton, IV et al. |
| 11,419,606 B2 | 8/2022 | Overmyer et al. |
| 11,419,630 B2 | 8/2022 | Yates et al. |
| 11,419,667 B2 | 8/2022 | Messerly et al. |
| 11,423,007 B2 | 8/2022 | Shelton, IV et al. |
| 11,424,027 B2 | 8/2022 | Shelton, IV |
| D964,564 S | 9/2022 | Boudreaux |
| 11,432,885 B2 | 9/2022 | Shelton, IV et al. |
| 11,446,052 B2 | 9/2022 | Shelton, IV et al. |
| 11,457,944 B2 | 10/2022 | Scoggins |
| 11,464,511 B2 | 10/2022 | Timm et al. |
| 11,464,513 B2 | 10/2022 | Shelton, IV et al. |
| 11,464,514 B2 | 10/2022 | Yates et al. |
| 11,464,532 B2 | 10/2022 | Nott et al. |
| 11,464,535 B2 | 10/2022 | Shelton, IV et al. |
| 11,464,559 B2 | 10/2022 | Nott et al. |
| 11,471,156 B2 | 10/2022 | Shelton, IV et al. |
| 11,471,206 B2 | 10/2022 | Henderson et al. |
| 11,478,244 B2 | 10/2022 | DiNardo et al. |
| 11,504,191 B2 | 11/2022 | Mccloud et al. |
| 11,504,192 B2 | 11/2022 | Shelton, IV et al. |
| 11,510,671 B2 | 11/2022 | Shelton, IV et al. |
| 11,510,675 B2 | 11/2022 | Shelton, IV et al. |
| 11,510,720 B2 | 11/2022 | Morgan et al. |
| 11,510,741 B2 | 11/2022 | Shelton, IV et al. |
| 11,517,309 B2 | 12/2022 | Bakos et al. |
| 11,517,315 B2 | 12/2022 | Huitema et al. |
| 11,529,187 B2 | 12/2022 | Shelton, IV et al. |
| 11,534,196 B2 | 12/2022 | Black |
| 11,540,824 B2 | 1/2023 | Shelton, IV et al. |
| 11,540,855 B2 | 1/2023 | Messerly et al. |
| 11,547,468 B2 | 1/2023 | Shelton, IV et al. |
| 11,571,212 B2 | 2/2023 | Yates et al. |
| 2001/0056237 A1 | 12/2001 | Cane et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2002/0144147 A1 | 10/2002 | Basson et al. |
| 2002/0169584 A1 | 11/2002 | Fu et al. |
| 2002/0194023 A1 | 12/2002 | Turley et al. |
| 2003/0009111 A1 | 1/2003 | Cory et al. |
| 2003/0009154 A1 | 1/2003 | Whitman |
| 2003/0018329 A1 | 1/2003 | Hooven |
| 2003/0046109 A1 | 3/2003 | Uchikubo |
| 2003/0050654 A1 | 3/2003 | Whitman et al. |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0120284 A1 | 6/2003 | Palacios et al. |
| 2003/0130711 A1 | 7/2003 | Pearson et al. |
| 2003/0210812 A1 | 11/2003 | Khamene et al. |
| 2003/0223877 A1 | 12/2003 | Anstine et al. |
| 2004/0015053 A1 | 1/2004 | Bieger et al. |
| 2004/0078236 A1 | 4/2004 | Stoodley et al. |
| 2004/0092992 A1 | 5/2004 | Adams et al. |

(56) References Cited

U.S. PATENT DOCUMENTS

| | | |
|---|---|---|
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0229496 A1 | 11/2004 | Robinson et al. |
| 2004/0243147 A1 | 12/2004 | Lipow |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0020918 A1 | 1/2005 | Wilk et al. |
| 2005/0021027 A1 | 1/2005 | Shields et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0070800 A1 | 3/2005 | Takahashi |
| 2005/0100867 A1 | 5/2005 | Hilscher et al. |
| 2005/0131390 A1 | 6/2005 | Heinrich et al. |
| 2005/0139629 A1 | 6/2005 | Schwemberger et al. |
| 2005/0143759 A1 | 6/2005 | Kelly |
| 2005/0148854 A1 | 7/2005 | Ito et al. |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1 | 9/2005 | Montpetit |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0213832 A1 | 9/2005 | Schofield et al. |
| 2005/0222631 A1 | 10/2005 | Dalal et al. |
| 2005/0228246 A1 | 10/2005 | Lee et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2005/0288425 A1 | 12/2005 | Lee et al. |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0142739 A1 | 6/2006 | DiSilestro et al. |
| 2006/0184160 A1 | 8/2006 | Ozaki et al. |
| 2006/0241399 A1 | 10/2006 | Fabian |
| 2006/0282009 A1 | 12/2006 | Oberg et al. |
| 2006/0287645 A1 | 12/2006 | Tashiro et al. |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0085528 A1 | 4/2007 | Govari et al. |
| 2007/0156019 A1 | 7/2007 | Larkin et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175951 A1 | 8/2007 | Shelton et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0192139 A1 | 8/2007 | Cookson et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0239028 A1 | 10/2007 | Houser et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0019393 A1 | 1/2008 | Yamaki |
| 2008/0033404 A1 | 2/2008 | Romoda et al. |
| 2008/0039742 A1 | 2/2008 | Hashimshony et al. |
| 2008/0040151 A1 | 2/2008 | Moore |
| 2008/0058593 A1 | 3/2008 | Gu et al. |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0164296 A1 | 7/2008 | Shelton et al. |
| 2008/0167644 A1 | 7/2008 | Shelton et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0223904 A1 | 9/2008 | Marczyk |
| 2008/0234708 A1 | 9/2008 | Houser et al. |
| 2008/0235052 A1 | 9/2008 | Node-Langlois et al. |
| 2008/0245841 A1 | 10/2008 | Smith et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048611 A1 | 2/2009 | Funda et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0157072 A1 | 6/2009 | Wham et al. |
| 2009/0182577 A1 | 7/2009 | Squilla et al. |
| 2009/0188094 A1 | 7/2009 | Cunningham et al. |
| 2009/0192591 A1 | 7/2009 | Ryan et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0259489 A1 | 10/2009 | Kimura et al. |
| 2009/0270678 A1 | 10/2009 | Scott et al. |
| 2009/0281541 A1 | 11/2009 | Ibrahim et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |

(56) References Cited

U.S. PATENT DOCUMENTS

| | | |
|---|---|---|
| 2010/0137886 A1 | 6/2010 | Zergiebel et al. |
| 2010/0162402 A1* | 6/2010 | Rachlin .......... G06F 21/60 |
| | | 726/26 |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0022032 A1 | 1/2011 | Zemlok et al. |
| 2011/0036890 A1 | 2/2011 | Ma |
| 2011/0043612 A1 | 2/2011 | Keller et al. |
| 2011/0046618 A1 | 2/2011 | Minar et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0087502 A1 | 4/2011 | Yelton et al. |
| 2011/0105277 A1 | 5/2011 | Shauli |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0218526 A1 | 9/2011 | Mathur |
| 2011/0237883 A1 | 9/2011 | Chun |
| 2011/0238079 A1 | 9/2011 | Hannaford et al. |
| 2011/0251612 A1 | 10/2011 | Faller et al. |
| 2011/0264000 A1 | 10/2011 | Paul et al. |
| 2011/0264078 A1 | 10/2011 | Lipow et al. |
| 2011/0265311 A1 | 11/2011 | Kondo et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0012638 A1 | 1/2012 | Huang et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203067 A1 | 8/2012 | Higgins et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0245958 A1 | 9/2012 | Lawrence et al. |
| 2012/0253329 A1 | 10/2012 | Zemlok et al. |
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0090755 A1 | 4/2013 | Kiryu et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0131845 A1 | 5/2013 | Guilleminot |
| 2013/0144284 A1 | 6/2013 | Behnke, II et al. |
| 2013/0153635 A1 | 6/2013 | Hodgkinson |
| 2013/0165776 A1 | 6/2013 | Blomqvist |
| 2013/0178853 A1 | 7/2013 | Hyink et al. |
| 2013/0190755 A1 | 7/2013 | Deborski et al. |
| 2013/0191647 A1 | 7/2013 | Ferrara, Jr. et al. |
| 2013/0193188 A1 | 8/2013 | Shelton, IV et al. |
| 2013/0196703 A1 | 8/2013 | Masoud et al. |
| 2013/0197531 A1 | 8/2013 | Boukhny et al. |
| 2013/0201356 A1 | 8/2013 | Kennedy et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0039491 A1 | 2/2014 | Bakos et al. |
| 2014/0058407 A1 | 2/2014 | Tsekos et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R. et al. |
| 2014/0117256 A1 | 5/2014 | Mueller et al. |
| 2014/0121669 A1 | 5/2014 | Claus |
| 2014/0142963 A1 | 5/2014 | Hill et al. |
| 2014/0148729 A1 | 5/2014 | Schmitz et al. |
| 2014/0148803 A1 | 5/2014 | Taylor |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0171787 A1 | 6/2014 | Garbey et al. |
| 2014/0176576 A1 | 6/2014 | Spencer |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |

(56) References Cited

U.S. PATENT DOCUMENTS

| | | |
|---|---|---|
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch, Jr. et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276748 A1 | 9/2014 | Ku et al. |
| 2014/0276749 A1 | 9/2014 | Johnson |
| 2014/0287393 A1 | 9/2014 | Kumar et al. |
| 2014/0296694 A1 | 10/2014 | Jaworski |
| 2014/0303660 A1 | 10/2014 | Boyden et al. |
| 2014/0303990 A1 | 10/2014 | Schoenefeld et al. |
| 2014/0336943 A1 | 11/2014 | Pellini et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0057675 A1 | 2/2015 | Akeel et al. |
| 2015/0062316 A1 | 3/2015 | Haraguchi et al. |
| 2015/0066000 A1 | 3/2015 | An et al. |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0083774 A1 | 3/2015 | Measamer et al. |
| 2015/0099458 A1 | 4/2015 | Weisner et al. |
| 2015/0108198 A1 | 4/2015 | Estrella |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0141980 A1 | 5/2015 | Jadhav et al. |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0201918 A1 | 7/2015 | Kumar et al. |
| 2015/0202014 A1 | 7/2015 | Kim et al. |
| 2015/0208934 A1 | 7/2015 | Sztrubel et al. |
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282733 A1 | 10/2015 | Fielden et al. |
| 2015/0282821 A1 | 10/2015 | Look et al. |
| 2015/0289925 A1 | 10/2015 | Voegele et al. |
| 2015/0296042 A1 | 10/2015 | Aoyama |
| 2015/0297200 A1 | 10/2015 | Fitzsimmons et al. |
| 2015/0297222 A1 | 10/2015 | Huitema et al. |
| 2015/0297311 A1 | 10/2015 | Tesar |
| 2015/0302157 A1 | 10/2015 | Collar et al. |
| 2015/0305828 A1 | 10/2015 | Park et al. |
| 2015/0310174 A1* | 10/2015 | Coudert ............... G06F 16/22 726/5 |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2016/0000437 A1 | 1/2016 | Giordano et al. |
| 2016/0001411 A1 | 1/2016 | Alberti |
| 2016/0015471 A1 | 1/2016 | Piron et al. |
| 2016/0019346 A1 | 1/2016 | Boston et al. |
| 2016/0022374 A1 | 1/2016 | Haider et al. |
| 2016/0034648 A1 | 2/2016 | Mohlenbrock et al. |
| 2016/0038224 A1 | 2/2016 | Couture et al. |
| 2016/0038253 A1 | 2/2016 | Piron et al. |
| 2016/0048780 A1 | 2/2016 | Sethumadhavan et al. |
| 2016/0058439 A1 | 3/2016 | Shelton, IV et al. |
| 2016/0066913 A1 | 3/2016 | Swayze et al. |
| 2016/0100837 A1 | 4/2016 | Huang et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0157717 A1 | 6/2016 | Gaster |
| 2016/0158468 A1 | 6/2016 | Tang et al. |
| 2016/0166336 A1 | 6/2016 | Razzaque et al. |
| 2016/0174998 A1 | 6/2016 | Lal et al. |
| 2016/0175025 A1 | 6/2016 | Strobl |
| 2016/0180045 A1 | 6/2016 | Syed |
| 2016/0182637 A1 | 6/2016 | Adriaens et al. |
| 2016/0184054 A1 | 6/2016 | Lowe |
| 2016/0192960 A1 | 7/2016 | Bueno et al. |
| 2016/0203599 A1 | 7/2016 | Gillies et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249920 A1 | 9/2016 | Gupta et al. |
| 2016/0267227 A1* | 9/2016 | Takeyama ............... G16Z 99/00 |
| 2016/0270732 A1 | 9/2016 | Källbäck et al. |
| 2016/0270861 A1 | 9/2016 | Guru et al. |
| 2016/0275259 A1 | 9/2016 | Nolan et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287337 A1 | 10/2016 | Aram et al. |
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310204 A1 | 10/2016 | Mchenry et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0331460 A1 | 11/2016 | Cheatham, III et al. |
| 2016/0331473 A1 | 11/2016 | Yamamura |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0350490 A1 | 12/2016 | Martinez et al. |
| 2016/0354160 A1 | 12/2016 | Crowley et al. |
| 2016/0354162 A1 | 12/2016 | Yen et al. |
| 2016/0361070 A1 | 12/2016 | Ardel et al. |
| 2016/0367305 A1 | 12/2016 | Hareland |
| 2016/0367401 A1 | 12/2016 | Claus |
| 2016/0374710 A1 | 12/2016 | Sinelnikov et al. |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0005911 A1 | 1/2017 | Kasargod et al. |
| 2017/0007247 A1 | 1/2017 | Shelton, IV et al. |
| 2017/0027603 A1 | 2/2017 | Pandey |
| 2017/0042604 A1 | 2/2017 | McFarland et al. |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |

(56) References Cited

U.S. PATENT DOCUMENTS

| | | |
|---|---|---|
| 2017/0086930 A1 | 3/2017 | Thompson et al. |
| 2017/0105754 A1 | 4/2017 | Boudreaux et al. |
| 2017/0105787 A1 | 4/2017 | Witt et al. |
| 2017/0116873 A1* | 4/2017 | Lendvay ................ G09B 5/02 |
| 2017/0119477 A1 | 5/2017 | Amiot et al. |
| 2017/0127499 A1 | 5/2017 | Unoson et al. |
| 2017/0132374 A1 | 5/2017 | Lee et al. |
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0164996 A1 | 6/2017 | Honda et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0172674 A1 | 6/2017 | Hanuschik et al. |
| 2017/0172676 A1 | 6/2017 | Itkowitz et al. |
| 2017/0173262 A1 | 6/2017 | Veltz |
| 2017/0177807 A1 | 6/2017 | Fabian |
| 2017/0178069 A1 | 6/2017 | Paterra et al. |
| 2017/0185732 A1 | 6/2017 | Niklewski et al. |
| 2017/0196583 A1 | 7/2017 | Sugiyama |
| 2017/0202595 A1 | 7/2017 | Shelton, IV |
| 2017/0202608 A1 | 7/2017 | Shelton, IV et al. |
| 2017/0209145 A1 | 7/2017 | Swayze et al. |
| 2017/0215944 A1 | 8/2017 | Keffeler |
| 2017/0224332 A1 | 8/2017 | Hunter et al. |
| 2017/0224428 A1 | 8/2017 | Kopp |
| 2017/0231553 A1 | 8/2017 | Igarashi et al. |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0255751 A1* | 9/2017 | Sanmugalingham ........................ G06F 21/6254 |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281186 A1 | 10/2017 | Shelton, IV et al. |
| 2017/0289617 A1 | 10/2017 | Song et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0319268 A1 | 11/2017 | Akagane |
| 2017/0325876 A1 | 11/2017 | Nakadate et al. |
| 2017/0325878 A1 | 11/2017 | Messerly et al. |
| 2017/0333147 A1 | 11/2017 | Bernstein |
| 2017/0333152 A1 | 11/2017 | Wade |
| 2017/0337043 A1 | 11/2017 | Brincat et al. |
| 2017/0360358 A1 | 12/2017 | Amiot et al. |
| 2017/0360499 A1 | 12/2017 | Greep et al. |
| 2017/0367583 A1 | 12/2017 | Black et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0014764 A1 | 1/2018 | Bechtel et al. |
| 2018/0021058 A1 | 1/2018 | Meglan |
| 2018/0042659 A1 | 2/2018 | Rupp et al. |
| 2018/0050196 A1 | 2/2018 | Pawsey et al. |
| 2018/0052971 A1 | 2/2018 | Hanina et al. |
| 2018/0065248 A1 | 3/2018 | Barral et al. |
| 2018/0078170 A1 | 3/2018 | Panescu et al. |
| 2018/0082480 A1 | 3/2018 | White et al. |
| 2018/0085102 A1 | 3/2018 | Kikuchi |
| 2018/0098049 A1 | 4/2018 | Sugano et al. |
| 2018/0098816 A1 | 4/2018 | Govari et al. |
| 2018/0108438 A1 | 4/2018 | Ryan et al. |
| 2018/0116735 A1 | 5/2018 | Tierney et al. |
| 2018/0122506 A1 | 5/2018 | Grantcharov et al. |
| 2018/0132895 A1 | 5/2018 | Silver |
| 2018/0144243 A1 | 5/2018 | Hsieh et al. |
| 2018/0144314 A1 | 5/2018 | Miller |
| 2018/0153436 A1 | 6/2018 | Olson |
| 2018/0153574 A1 | 6/2018 | Faller et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0172420 A1 | 6/2018 | Hein et al. |
| 2018/0177383 A1 | 6/2018 | Noonan et al. |
| 2018/0182475 A1 | 6/2018 | Cossler et al. |
| 2018/0183684 A1 | 6/2018 | Jacobson et al. |
| 2018/0193579 A1 | 7/2018 | Hanrahan et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0233235 A1 | 8/2018 | Angelides |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0247128 A1 | 8/2018 | Alvi et al. |
| 2018/0247711 A1 | 8/2018 | Terry |
| 2018/0250086 A1 | 9/2018 | Grubbs |
| 2018/0250825 A1 | 9/2018 | Hashimoto et al. |
| 2018/0263699 A1 | 9/2018 | Murphy et al. |
| 2018/0263710 A1 | 9/2018 | Sakaguchi et al. |
| 2018/0268320 A1 | 9/2018 | Shekhar |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0296289 A1 | 10/2018 | Rodriguez-Navarro et al. |
| 2018/0300506 A1 | 10/2018 | Kawakami et al. |
| 2018/0303552 A1 | 10/2018 | Ryan et al. |
| 2018/0304471 A1 | 10/2018 | Tokuchi |
| 2018/0310986 A1 | 11/2018 | Batchelor et al. |
| 2018/0315492 A1 | 11/2018 | Bishop et al. |
| 2018/0317916 A1 | 11/2018 | Wixey |
| 2018/0325619 A1 | 11/2018 | Rauniyar et al. |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0353186 A1 | 12/2018 | Mozdzierz et al. |
| 2018/0357383 A1 | 12/2018 | Allen et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |

(56) References Cited

U.S. PATENT DOCUMENTS

| | | |
|---|---|---|
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0045515 A1 | 2/2019 | Kwasnick et al. |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0059986 A1 | 2/2019 | Shelton, IV et al. |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0099221 A1 | 4/2019 | Schmidt et al. |
| 2019/0099226 A1 | 4/2019 | Hallen |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0122330 A1* | 4/2019 | Saget ................ G06T 3/0081 |
| 2019/0125320 A1 | 5/2019 | Shelton, IV et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0163875 A1 | 5/2019 | Allen et al. |
| 2019/0167296 A1 | 6/2019 | Tsubuku et al. |
| 2019/0192044 A1 | 6/2019 | Ravi et al. |
| 2019/0192157 A1 | 6/2019 | Scott et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200997 A1 | 7/2019 | Shelton, IV et al. |
| 2019/0201021 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201034 A1 | 7/2019 | Shelton, IV et al. |
| 2019/0201036 A1 | 7/2019 | Nott et al. |
| 2019/0201038 A1 | 7/2019 | Yates et al. |
| 2019/0201039 A1 | 7/2019 | Widenhouse et al. |
| 2019/0201042 A1 | 7/2019 | Nott et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201075 A1 | 7/2019 | Shelton, IV et al. |
| 2019/0201076 A1 | 7/2019 | Honda et al. |
| 2019/0201085 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201102 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |
| 2019/0201123 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201130 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201594 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205567 A1 | 7/2019 | Shelton, IV et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274711 A1 | 9/2019 | Scoggins et al. |
| 2019/0274713 A1 | 9/2019 | Scoggins et al. |
| 2019/0274714 A1 | 9/2019 | Cuti et al. |
| 2019/0274718 A1 | 9/2019 | Denzinger et al. |
| 2019/0274719 A1 | 9/2019 | Stulen |
| 2019/0274749 A1 | 9/2019 | Brady et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298350 A1 | 10/2019 | Shelton, IV et al. |
| 2019/0298353 A1 | 10/2019 | Shelton, IV et al. |
| 2019/0298464 A1 | 10/2019 | Abbott |
| 2019/0307520 A1 | 10/2019 | Peine et al. |
| 2019/0311802 A1 | 10/2019 | Kokubo et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0365569 A1 | 12/2019 | Skovgaard et al. |
| 2019/0374140 A1 | 12/2019 | Tucker et al. |
| 2019/0374292 A1 | 12/2019 | Barral et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054321 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078078 A1 | 3/2020 | Henderson et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |

(56) References Cited

U.S. PATENT DOCUMENTS

| | | |
|---|---|---|
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0222149 A1 | 7/2020 | Valentine et al. |
| 2020/0226751 A1 | 7/2020 | Jin et al. |
| 2020/0230803 A1 | 7/2020 | Yamashita et al. |
| 2020/0237372 A1 | 7/2020 | Park |
| 2020/0261086 A1 | 8/2020 | Zeiner et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0348662 A1 | 11/2020 | Cella et al. |
| 2020/0352664 A1 | 11/2020 | King et al. |
| 2020/0388385 A1 | 12/2020 | De Los Reyes et al. |
| 2020/0405304 A1 | 12/2020 | Mozdzierz et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzadi et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0220058 A1 | 7/2021 | Messerly et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0157306 A1 | 5/2022 | Albrecht et al. |
| 2022/0160438 A1 | 5/2022 | Shelton, IV et al. |
| 2022/0175374 A1 | 6/2022 | Shelton, IV et al. |
| 2022/0230738 A1 | 7/2022 | Shelton, IV et al. |
| 2022/0241027 A1 | 8/2022 | Shelton, IV et al. |
| 2022/0249097 A1 | 8/2022 | Shelton, IV et al. |
| 2022/0323092 A1 | 10/2022 | Shelton, IV et al. |
| 2022/0323095 A1 | 10/2022 | Nott et al. |
| 2022/0323150 A1 | 10/2022 | Yates et al. |
| 2022/0331011 A1 | 10/2022 | Shelton, IV et al. |
| 2022/0331018 A1 | 10/2022 | Parihar et al. |
| 2022/0346792 A1 | 11/2022 | Shelton, IV et al. |
| 2022/0370117 A1 | 11/2022 | Messerly et al. |
| 2022/0370126 A1 | 11/2022 | Shelton, IV et al. |
| 2022/0374414 A1 | 11/2022 | Shelton, IV et al. |
| 2022/0395276 A1 | 12/2022 | Yates et al. |
| 2022/0401099 A1 | 12/2022 | Shelton, IV et al. |
| 2022/0406452 A1 | 12/2022 | Shelton, IV |
| 2022/0409302 A1 | 12/2022 | Shelton, IV et al. |
| 2023/0000518 A1 | 1/2023 | Nott et al. |
| 2023/0037577 A1 | 2/2023 | Kimball et al. |
| 2023/0064821 A1 | 3/2023 | Shelton, IV |

FOREIGN PATENT DOCUMENTS

| | | | |
|---|---|---|---|
| CN | 101617950 A | 1/2010 | |
| CN | 104490448 B | 3/2017 | |
| CN | 206097107 U | 4/2017 | |
| CN | 107811710 A * | 3/2018 | ............ A61B 34/35 |
| CN | 108652695 A | 10/2018 | |
| DE | 3016131 A1 | 10/1981 | |
| DE | 3824913 A1 | 2/1990 | |
| DE | 4002843 C1 | 4/1991 | |
| DE | 102005051367 A1 | 4/2007 | |
| DE | 102016207666 A1 | 11/2017 | |
| EP | 0000756 B1 | 10/1981 | |
| EP | 0408160 A1 | 1/1991 | |
| EP | 0473987 A1 | 3/1992 | |
| EP | 0929263 B1 | 7/1999 | |
| EP | 1214913 A2 | 6/2002 | |
| EP | 2730209 A1 | 5/2014 | |
| EP | 2732772 A1 | 5/2014 | |
| EP | 2942023 A2 | 11/2015 | |
| EP | 3047806 A1 | 7/2016 | |
| EP | 3056923 A1 | 8/2016 | |
| EP | 3095399 A2 | 11/2016 | |
| EP | 3120781 A2 | 1/2017 | |
| EP | 3135225 A2 | 3/2017 | |
| EP | 3141181 A1 | 3/2017 | |
| FR | 2838234 A1 | 10/2003 | |
| GB | 2037167 A1 | 7/1980 | |
| GB | 2509523 A | 7/2014 | |
| JP | S5191993 U | 7/1976 | |
| JP | S5373315 A | 6/1978 | |
| JP | S57185848 A | 11/1982 | |
| JP | S58207752 A | 12/1983 | |
| JP | S63315049 A | 12/1988 | |
| JP | H06142113 A | 5/1994 | |
| JP | H06209902 A | 8/1994 | |
| JP | H07132122 A | 5/1995 | |
| JP | H08332169 A | 12/1996 | |

(56) References Cited

FOREIGN PATENT DOCUMENTS

| | | |
|---|---|---|
| JP | H09154850 A | 6/1997 |
| JP | H11197159 A | 7/1999 |
| JP | 2000058355 A | 2/2000 |
| JP | 2001029353 A | 2/2001 |
| JP | 2001195686 A | 7/2001 |
| JP | 2001314411 A | 11/2001 |
| JP | 2001340350 A | 12/2001 |
| JP | 2002272758 A | 9/2002 |
| JP | 2003153918 A | 5/2003 |
| JP | 2006117143 A | 5/2006 |
| JP | 2006288431 A | 10/2006 |
| JP | 2007123394 A | 5/2007 |
| JP | 2007139822 A | 6/2007 |
| JP | 2007300312 A | 11/2007 |
| JP | 2009039515 A | 2/2009 |
| JP | 2010057642 A | 3/2010 |
| JP | 2010131265 A | 6/2010 |
| JP | 2012065698 A | 4/2012 |
| JP | 2012239669 A | 12/2012 |
| JP | 2012533346 A | 12/2012 |
| JP | 2013081282 A | 5/2013 |
| JP | 2013144057 A | 7/2013 |
| JP | 2014155207 A | 8/2014 |
| JP | 2015085454 A | 5/2015 |
| JP | 2016514017 A | 5/2016 |
| JP | 2016174836 A | 10/2016 |
| JP | 2017047022 A | 3/2017 |
| JP | 2017513561 A | 6/2017 |
| JP | 2017526510 A | 9/2017 |
| JP | 2017532168 A | 11/2017 |
| KR | 20140104587 A | 8/2014 |
| KR | 101587721 B1 | 1/2016 |
| WO | WO-9734533 A1 | 9/1997 |
| WO | WO-9808449 A1 | 3/1998 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2006001264 A1 | 1/2006 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014116961 A1 | 7/2014 |
| WO | WO-2014134196 A1 | 9/2014 |
| WO | WO-2015030157 A1 | 3/2015 |
| WO | WO-2015054665 A1 | 4/2015 |
| WO | WO-2015129395 A1 | 9/2015 |
| WO | WO-2016093049 A1 | 6/2016 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 A2 | 4/2017 |
| WO | WO-2017058695 A1 | 4/2017 |
| WO | WO-2017151996 A1 | 9/2017 |
| WO | WO-2017183353 A1 | 10/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." Inter-

(56) References Cited

OTHER PUBLICATIONS national Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode,"Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "ARCM", Video, Sep. 2012, YouTube, 5 screenshots, Retrieved from internet: <https://www.youtube.com/watch?v=UldQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An intuitive control console for robotic surgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1755-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.
Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
"Surgical instrumentation: the true cost of instrument trays and a potential strategy for optimization"; Mhlaba et al.; Sep. 23, 2015 (Year: 2015).
Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdfXP055530863.
Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.
Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.
Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).
Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.
Lalys, et al., "Automatic knowledge-based recognition of low-level tasks in ophthalmological procedures", Int J CARS, vol. 8, No. 1, pp. 1-49, Apr. 19, 2012.
Hu, Jinwen, Stimulations of adaptive temperature control with self-focused hyperthermia system for tumor treatment, Jan. 9, 2012, Ultrasonics 53, pp. 171-177, (Year: 2012).
Hussain et al., "A survey on resource allocation in high performance distributed computing systems", Parallel Computing, vol. 39, No. 11, pp. 709-736 (2013).
Anonymous: "Quality of service—Wikipedia", Dec. 7, 2017, Retrieved from the Internet: URL:https://en.wikipedia.org/w/index.php?title=Quality_of_service&oldid=814298744#Applications [retrieved on Feb. 14, 2023], pp. 1-12.
Anonymous: "Differentiated services—Wikipedia", Dec. 14, 2017, Retrieved from the Internet: URL:https://en.wikipedia.org/w/index.php?title=Differentiated_services&oldid=815415620 [retrieved on Feb. 14, 2023], pp. 1-7.

(56) References Cited

OTHER PUBLICATIONS

Anonymous: "Cloud computing—Wikipedia", Dec. 19, 2017, Retrieved from the Internet: URL:https://en.wikipedia.org/w/index.php?title=Cloud_computing&oldid=816206558 [retrieved Feb. 14, 2023], pp. 1-21.

\* cited by examiner

DATA STRIPPING METHOD TO INTERROGATE PATIENT RECORDS AND CREATE ANONYMIZED RECORD

CROSS REFERENCE TO RELATED APPLICATIONS

This application claims priority to U.S. patent application Ser. No. 15/940,632, titled DATA STRIPPING METHOD TO INTERROGATE PATIENT RECORDS AND CREATE ANONYMIZED RECORD, filed Mar. 29, 2018, which issued on Sep. 28, 2021 as U.S. Pat. No. 11,132,462, the disclosure of which is herein incorporated by reference in its entirety.

U.S. patent application Ser. No. 15/940,632 claims the benefit of priority under 35 U.S.C. 119(e) to U.S. Provisional Patent Application Ser. No. 62/649,294, titled DATA STRIPPING METHOD TO INTERROGATE PATIENT RECORDS AND CREATE ANONYMIZED RECORD, filed Mar. 28, 2018, the disclosure of which is herein incorporated by reference in its entirety.

U.S. patent application Ser. No. 15/940,632 also claims the benefit of priority under 35 U.S.C. 119(e) to U.S. Provisional Patent Application Ser. No. 62/611,341, titled INTERACTIVE SURGICAL PLATFORM, filed Dec. 28, 2017, of U.S. Provisional Patent Application Ser. No. 62/611,340, titled CLOUD-BASED MEDICAL ANALYTICS, filed Dec. 28, 2017, of U.S. Provisional Patent Application Ser. No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to various surgical systems. Surgical procedures are typically performed in surgical operating theaters or rooms in a healthcare facility such as, for example, a hospital. A sterile field is typically created around the patient. The sterile field may include the scrubbed team members, who are properly attired, and all furniture and fixtures in the area. Various surgical devices and systems are utilized in performance of a surgical procedure.

SUMMARY

In one general aspect, a surgical hub is provided. The surgical hub comprises a processor and a memory coupled to the processor. The memory stores instructions executable by the processor to interrogate a modular device coupled to the processor via a modular communication hub. The modular device is a source of data sets that include patient identity data and surgical procedure data. The processor also executes instructions to: receive a data set from the modular device; discard the patient identity data and any portion of the surgical procedure data that identifies the patient from the data set; extract anonymous data from the data set and create an anonymized data set; and configure operation of the surgical hub or the modular device based on the anonymized data set.

In another general aspect, another surgical hub and data stripping method is provided. A surgical hub is coupled to a modular device by a communication hub, and a method is provided of stripping data originating from the modular device. The surgical hub comprises a processor and a memory coupled to the processor. The memory stores instructions executable by the processor, comprising: interrogating, by a processor, a modular device coupled to the processor via a modular communication hub. The modular device is a source of data sets that include patient identity data and surgical procedure data. The modular communication hub is configured to connect modular devices located in one or more operating theaters to a surgical hub. The memory stored instructions executable by the processor further comprise: receiving, by the processor, a data set from the modular device by the processor via the communication hub; discarding, by the processor, the patient identity data and any portion of the surgical procedure data that identifies the patient from the data set; extracting, by the processor, anonymous data from the data set and create an anonymized data set; and configuring, by the processor, operation of the surgical hub or the modular device based on the anonymized data set.

In yet another general aspect, a non-transitory computer-readable medium stores computer-readable instructions that, when executed, cause a machine to: interrogate a modular device coupled to the processor via the modular communication hub, wherein the modular device is a source of data sets that include patient identity data and surgical procedure data; receive a data set from the modular device; discard the patient identity data and any portion of the surgical procedure data that identifies the patient from the data set; extract anonymous data from the data set and create an anonymized data set; and configure operation of the surgical hub or the modular device based on the anonymized data set.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

DESCRIPTION

Figure 1:
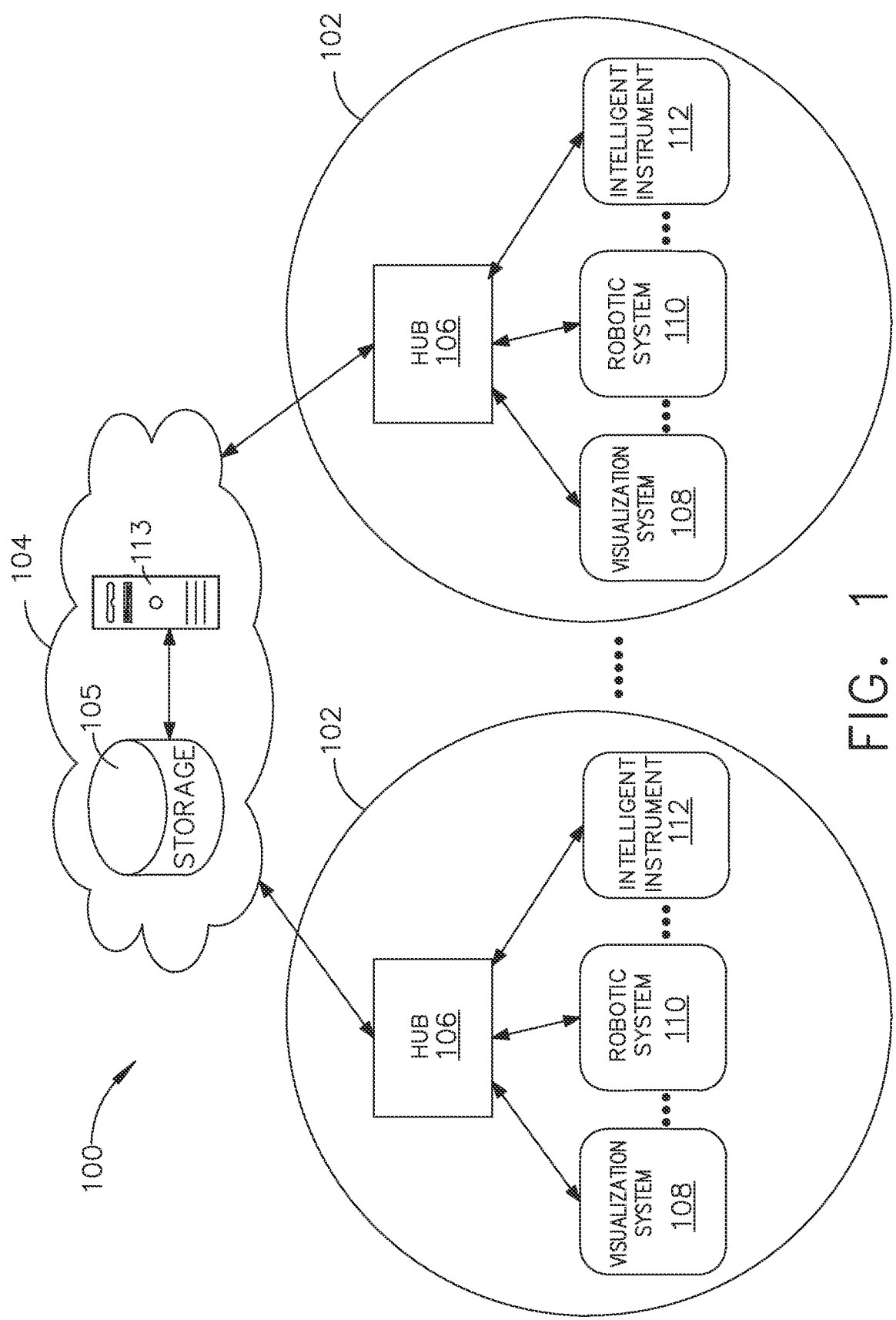
FIG. 1 is a block diagram of a computer-implemented interactive surgical system, in accordance with at least one aspect of the present disclosure.

Applicant of the present application owns the following U.S. Provisional Patent Applications, filed on Mar. 28, 2018, each of which is herein incorporated by reference in its entirety:

U.S. Provisional Patent Application Ser. No. 62/649,302, titled INTERACTIVE SURGICAL SYSTEMS WITH ENCRYPTED COMMUNICATION CAPABILITIES;

U.S. Provisional Patent Application Ser. No. 62/649,294, titled DATA STRIPPING METHOD TO INTERROGATE PATIENT RECORDS AND CREATE ANONYMIZED RECORD;

U.S. Provisional Patent Application Ser. No. 62/649,300, titled SURGICAL HUB SITUATIONAL AWARENESS;

U.S. Provisional Patent Application Ser. No. 62/649,309, titled SURGICAL HUB SPATIAL AWARENESS TO DETERMINE DEVICES IN OPERATING THEATER;

U.S. Provisional Patent Application Ser. No. 62/649,310, titled COMPUTER IMPLEMENTED INTERACTIVE SURGICAL SYSTEMS;

U.S. Provisional Patent Application Ser. No. 62/649,291, titled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, titled ADAPTIVE CONTROL PROGRAM UPDATES FOR SURGICAL DEVICES;

U.S. Provisional Patent Application Ser. No. 62/649,333, titled CLOUD-BASED MEDICAL ANALYTICS FOR CUSTOMIZATION AND RECOMMENDATIONS TO A USER;

U.S. Provisional Patent Application Ser. No. 62/649,327, titled CLOUD-BASED MEDICAL ANALYTICS FOR SECURITY AND AUTHENTICATION TRENDS AND REACTIVE MEASURES;

U.S. Provisional Patent Application Ser. No. 62/649,315, titled DATA HANDLING AND PRIORITIZATION IN A CLOUD ANALYTICS NETWORK;

U.S. Provisional Patent Application Ser. No. 62/649,313, titled CLOUD INTERFACE FOR COUPLED SURGICAL DEVICES;

U.S. Provisional Patent Application Ser. No. 62/649,320, titled DRIVE ARRANGEMENTS FOR ROBOT-ASSISTED SURGICAL PLATFORMS;

U.S. Provisional Patent Application Ser. No. 62/649,307, titled AUTOMATIC TOOL ADJUSTMENTS FOR ROBOT-ASSISTED SURGICAL PLATFORMS; and U.S. Provisional Patent Application Ser. No. 62/649,323, titled SENSING ARRANGEMENTS FOR ROBOT-ASSISTED SURGICAL PLATFORMS.

Applicant of the present application owns the following U.S. patent applications, filed on Mar. 29, 2018, each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES, now U.S. Pat. No. 10,944,728;

U.S. patent application Ser. No. 15/940,648, titled INTERACTIVE SURGICAL SYSTEMS WITH CONDITION HANDLING OF DEVICES AND DATA CAPABILITIES, now U.S. Patent Application Publication No. 2019/0206004;

U.S. patent application Ser. No. 15/940,656, titled SURGICAL HUB COORDINATION OF CONTROL AND COMMUNICATION OF OPERATING ROOM DEVICES, now U.S. Patent Application Publication No. 2019/0201141;

U.S. patent application Ser. No. 15/940,666, titled SPATIAL AWARENESS OF SURGICAL HUBS IN OPERATING ROOMS, now U.S. Patent Application Publication No. 2019/0206551;

U.S. patent application Ser. No. 15/940,670, titled COOPERATIVE UTILIZATION OF DATA DERIVED FROM SECONDARY SOURCES BY INTELLIGENT SURGICAL HUBS, now U.S. Patent Application Publication No. 2019/0201116;

U.S. patent application Ser. No. 15/940,677, titled SURGICAL HUB CONTROL ARRANGEMENTS, now U.S. Patent Application Publication No. 2019/0201143;

U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS, now U.S. Patent Application Publication No. 2019/0200863;

U.S. patent application Ser. No. 15/940,645, titled SELF DESCRIBING DATA PACKETS GENERATED AT AN ISSUING INSTRUMENT, now U.S. Pat. No. 10,892,899;

U.S. patent application Ser. No. 15/940,649, titled DATA PAIRING TO INTERCONNECT A DEVICE MEASURED PARAMETER WITH AN OUTCOME, now U.S. Patent Application Publication No. 2019/0205567;

U.S. patent application Ser. No. 15/940,654, titled SURGICAL HUB SITUATIONAL AWARENESS, now U.S. Patent Application Publication No. 2019/0201140;

U.S. patent application Ser. No. 15/940,663, titled SURGICAL SYSTEM DISTRIBUTED PROCESSING, now U.S. Patent Application Publication No. 2019/0201033;

U.S. patent application Ser. No. 15/940,668, titled AGGREGATION AND REPORTING OF SURGICAL HUB DATA, now U.S. Patent Application Publication No. 2019/0201115;

U.S. patent application Ser. No. 15/940,671, titled SURGICAL HUB SPATIAL AWARENESS TO DETERMINE DEVICES IN OPERATING THEATER, now U.S. Patent Application Publication No. 2019/0201104;

U.S. patent application Ser. No. 15/940,686, titled DISPLAY OF ALIGNMENT OF STAPLE CARTRIDGE TO PRIOR LINEAR STAPLE LINE, now U.S. Patent Application Publication No. 2019/0201105;

U.S. patent application Ser. No. 15/940,700, titled STERILE FIELD INTERACTIVE CONTROL DISPLAYS, now U.S. Patent Application Publication No. 2019/0205001;

U.S. patent application Ser. No. 15/940,629, titled COMPUTER IMPLEMENTED INTERACTIVE SURGICAL SYSTEMS, now U.S. Patent Application Publication No. 2019/0201112;

U.S. patent application Ser. No. 15/940,704, titled USE OF LASER LIGHT AND RED-GREEN-BLUE COLORATION TO DETERMINE PROPERTIES OF BACK SCATTERED LIGHT, now U.S. Patent Application Publication No. 2019/0206050;

U.S. patent application Ser. No. 15/940,722, titled CHARACTERIZATION OF TISSUE IRREGULARITIES THROUGH THE USE OF MONO-CHROMATIC LIGHT REFRACTIVITY, now U.S. Patent Application Publication No. 2019/0200905; and U.S. patent application Ser. No. 15/940,742, titled DUAL CMOS ARRAY IMAGING, now U.S. Patent Application Publication No. 2019/0200906.

Applicant of the present application owns the following U.S. patent applications, filed on Mar. 29, 2018, each of which is herein incorporated by reference in its entirety:

- U.S. patent application Ser. No. 15/940,636, titled ADAPTIVE CONTROL PROGRAM UPDATES FOR SURGICAL DEVICES, now U.S. Patent Application Publication No. 2019/0206003;
- U.S. patent application Ser. No. 15/940,653, titled ADAPTIVE CONTROL PROGRAM UPDATES FOR SURGICAL HUBS, now U.S. Patent Application Publication No. 2019/0201114;
- U.S. patent application Ser. No. 15/940,660, titled CLOUD-BASED MEDICAL ANALYTICS FOR CUSTOMIZATION AND RECOMMENDATIONS TO A USER, now U.S. Patent Application Publication No. 2019/0206555;
- U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET, now U.S. Pat. No. 10,932,872;
- U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION, now U.S. Patent Application Publication No. 2019/0201119;
- U.S. patent application Ser. No. 15/940,634, titled CLOUD-BASED MEDICAL ANALYTICS FOR SECURITY AND AUTHENTICATION TRENDS AND REACTIVE MEASURES, now U.S. Patent Application Publication No. 2019/0201138;
- U.S. patent application Ser. No. 15/940,706, titled DATA HANDLING AND PRIORITIZATION IN A CLOUD ANALYTICS NETWORK, now U.S. Patent Application Publication No. 2019/0206561; and
- U.S. patent application Ser. No. 15/940,675, titled CLOUD INTERFACE FOR COUPLED SURGICAL DEVICES, now U.S. Pat. No. 10,849,697.

Applicant of the present application owns the following U.S. patent applications, filed on Mar. 29, 2018, each of which is herein incorporated by reference in its entirety:

- U.S. patent application Ser. No. 15/940,627, titled DRIVE ARRANGEMENTS FOR ROBOT-ASSISTED SURGICAL PLATFORMS, now U.S. Patent Application Publication No. 2019/0201111;
- U.S. patent application Ser. No. 15/940,637, titled COMMUNICATION ARRANGEMENTS FOR ROBOT-ASSISTED SURGICAL PLATFORMS, now U.S. Patent Application Publication No. 2019/0201139;
- U.S. patent application Ser. No. 15/940,642, titled CONTROLS FOR ROBOT-ASSISTED SURGICAL PLATFORMS, now U.S. Patent Application Publication No. 2019/0201113;
- U.S. patent application Ser. No. 15/940,676, titled AUTOMATIC TOOL ADJUSTMENTS FOR ROBOT-ASSISTED SURGICAL PLATFORMS, now U.S. Patent Application Publication No. 2019/0201142;
- U.S. patent application Ser. No. 15/940,680, titled CONTROLLERS FOR ROBOT-ASSISTED SURGICAL PLATFORMS, now U.S. Patent Application Publication No. 2019/0201135;
- U.S. patent application Ser. No. 15/940,683, titled COOPERATIVE SURGICAL ACTIONS FOR ROBOT-ASSISTED SURGICAL PLATFORMS, now U.S. Patent Application Publication No. 2019/0201145;
- U.S. patent application Ser. No. 15/940,690, titled DISPLAY ARRANGEMENTS FOR ROBOT-ASSISTED SURGICAL PLATFORMS, now U.S. Patent Application Publication No. 2019/0201118; and
- U.S. patent application Ser. No. 15/940,711, titled SENSING ARRANGEMENTS FOR ROBOT-ASSISTED SURGICAL PLATFORMS, now U.S. Patent Application Publication No. 2019/0201120.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
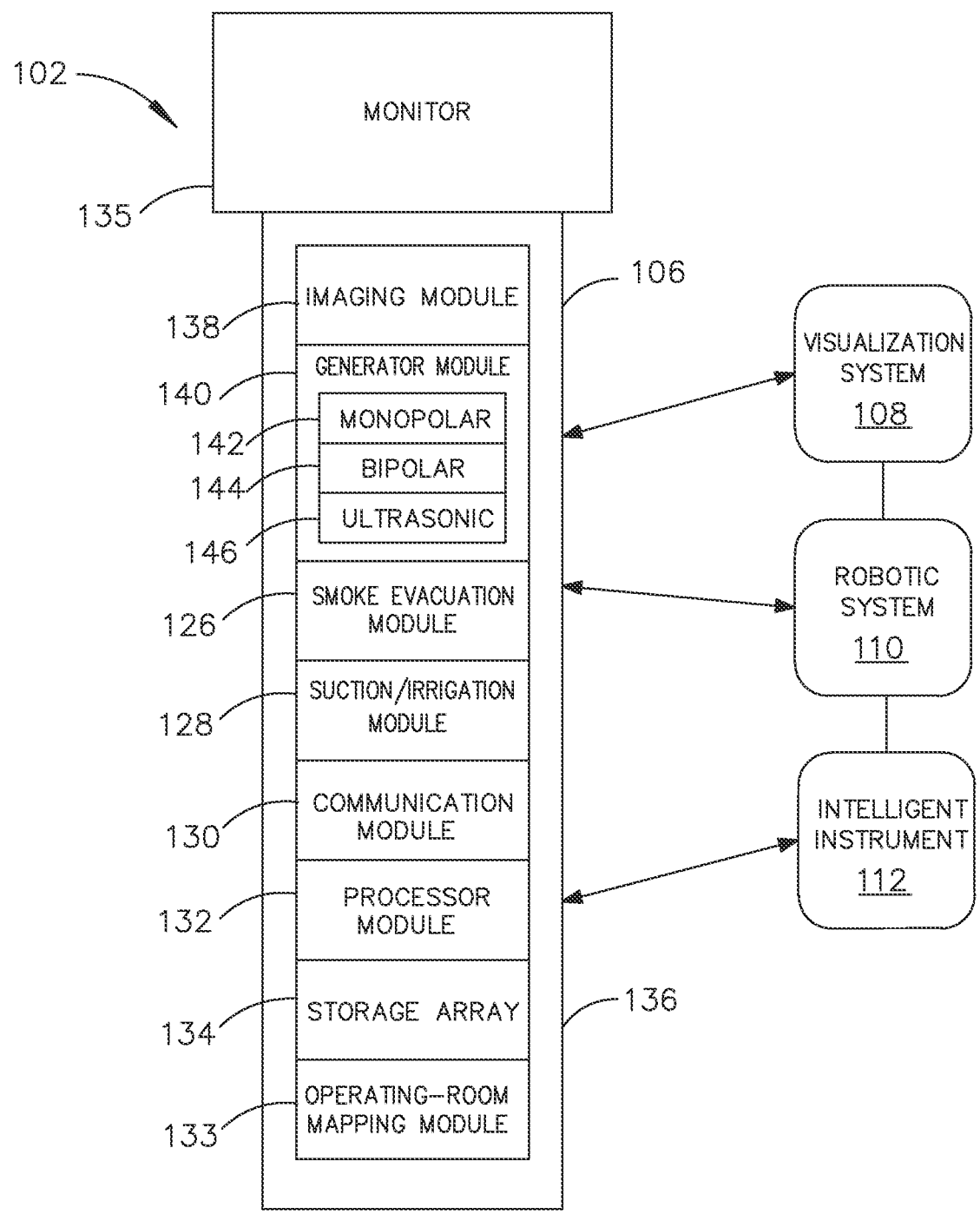
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
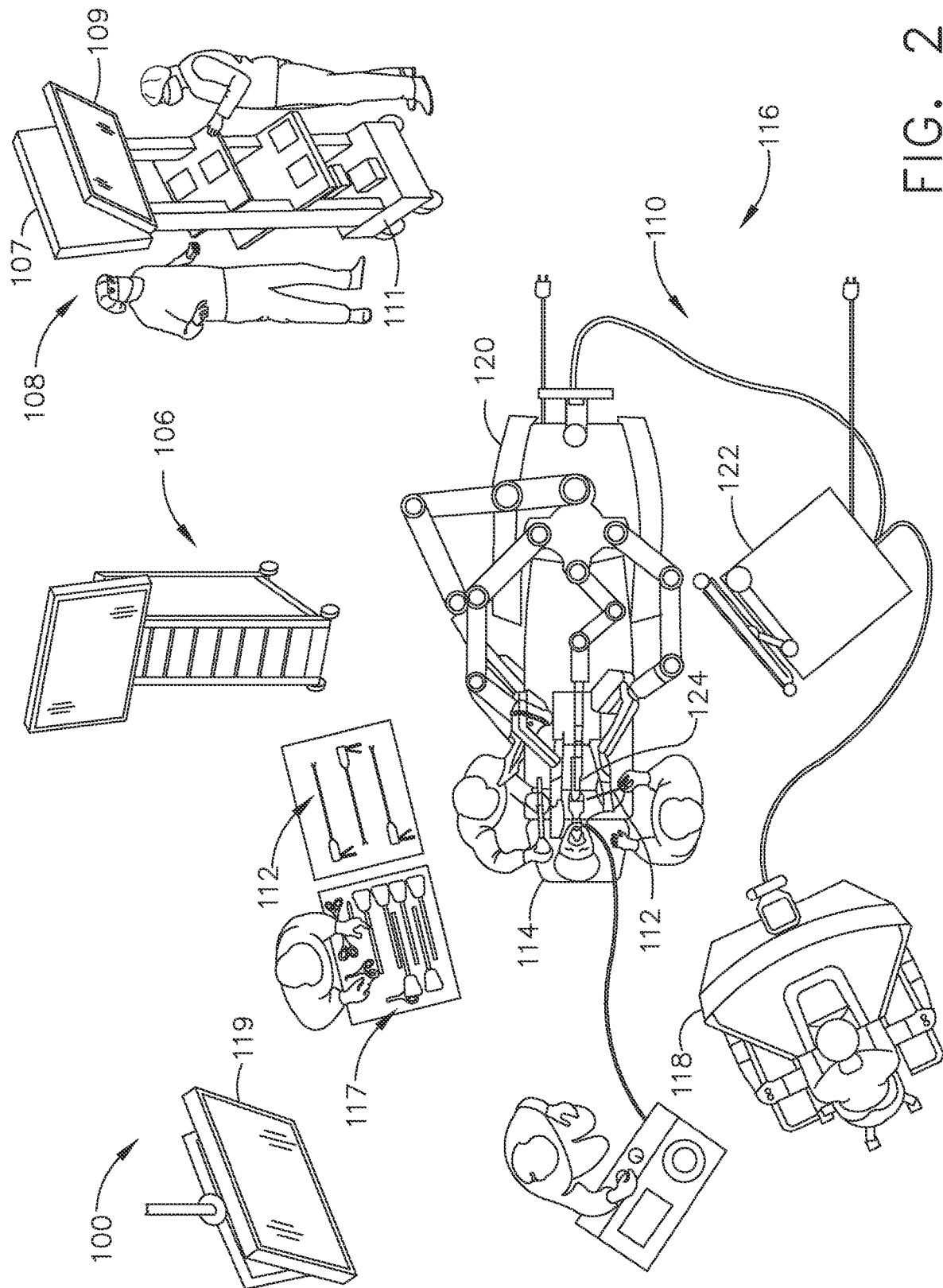
FIG. 2 is a surgical system being used to perform a surgical procedure in an operating room, in accordance with at least one aspect of the present disclosure.

In various aspects, the visualization system 108 includes one or more imaging sensors, one or more image processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snap-shot of a surgical site, as recorded by an imaging device 124, on a non-sterile display 107 or 109, while maintaining a live feed of the surgical site on the primary display 119. The snap-shot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snap-shot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts.

Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
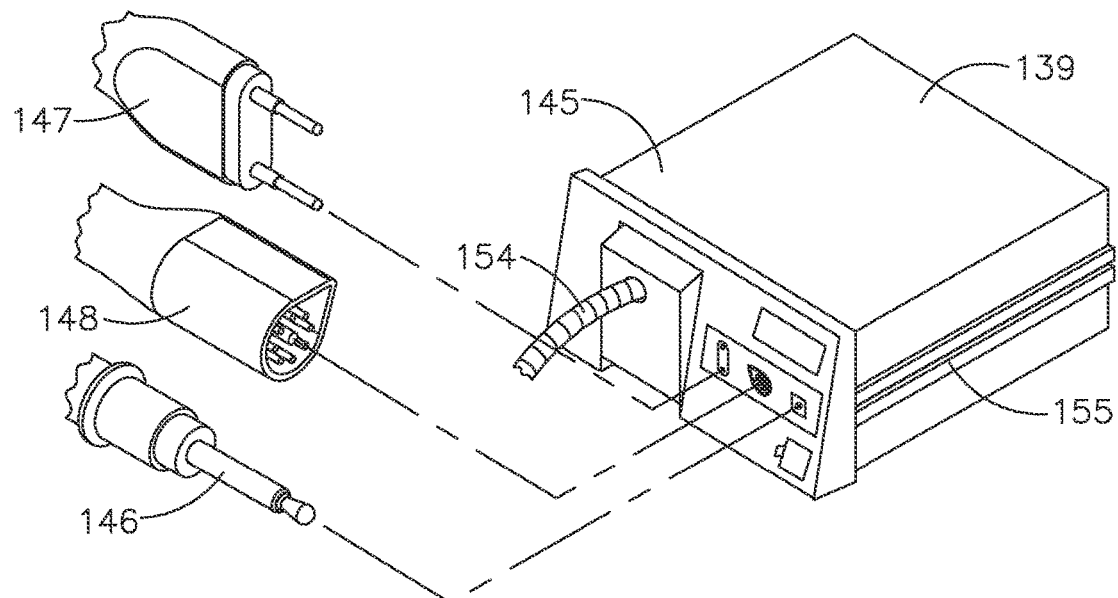
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
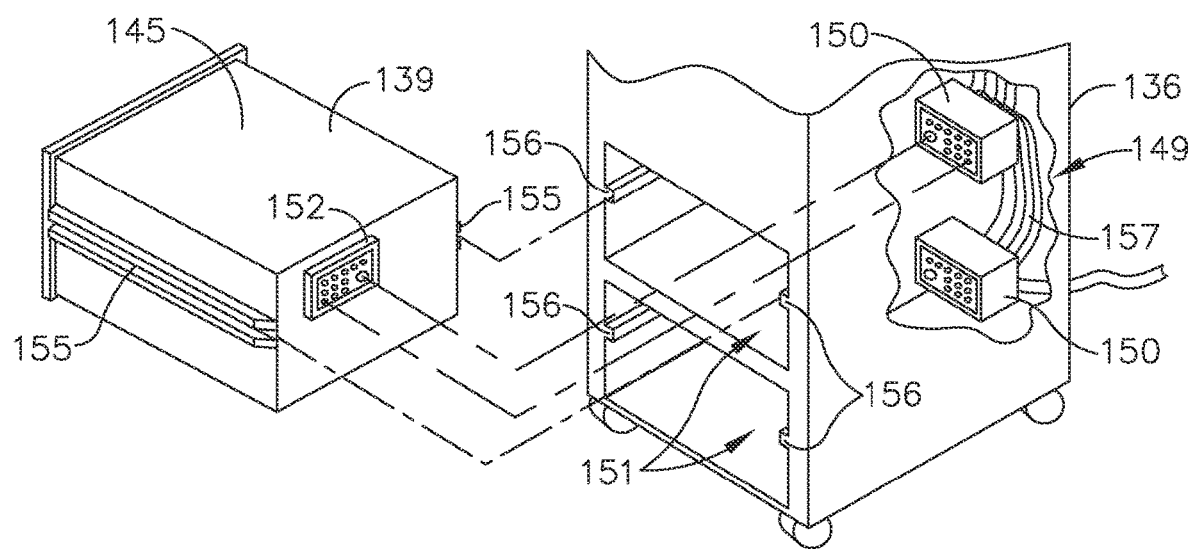
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
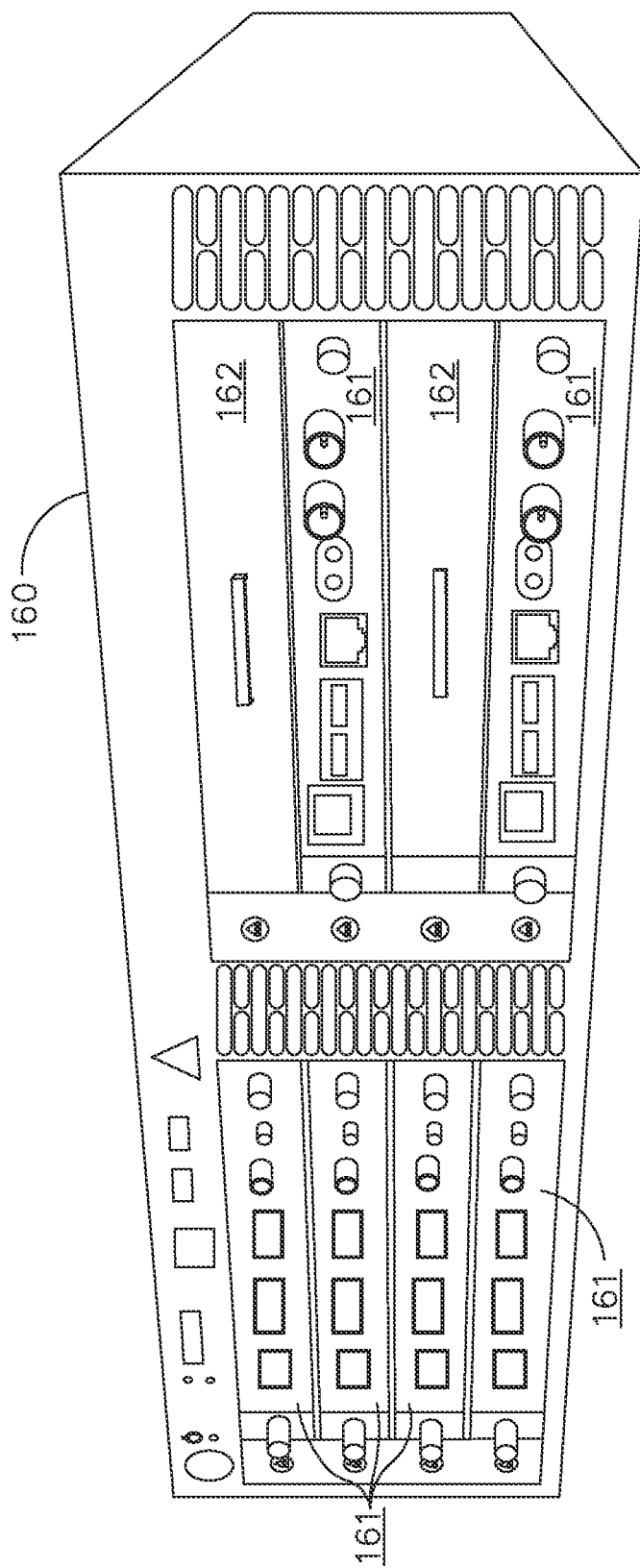
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
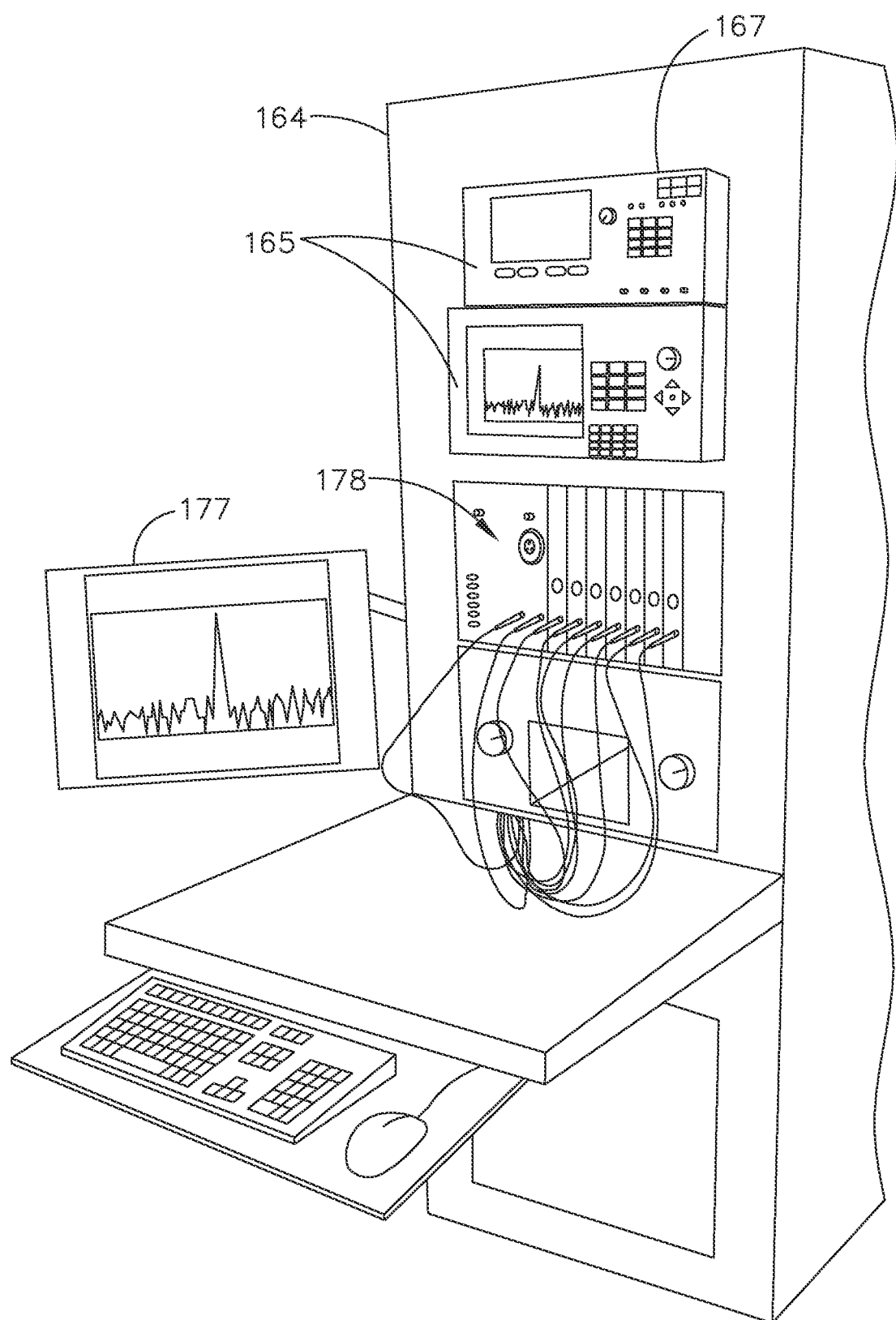
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Pat. No. 10,098,527, titled SYSTEM FOR PERFORMING A MINIMALLY INVASIVE SURGICAL PROCEDURE, which issued on Oct. 16, 2018, each of which is herein incorporated by reference in its entirety.

Figure 8:
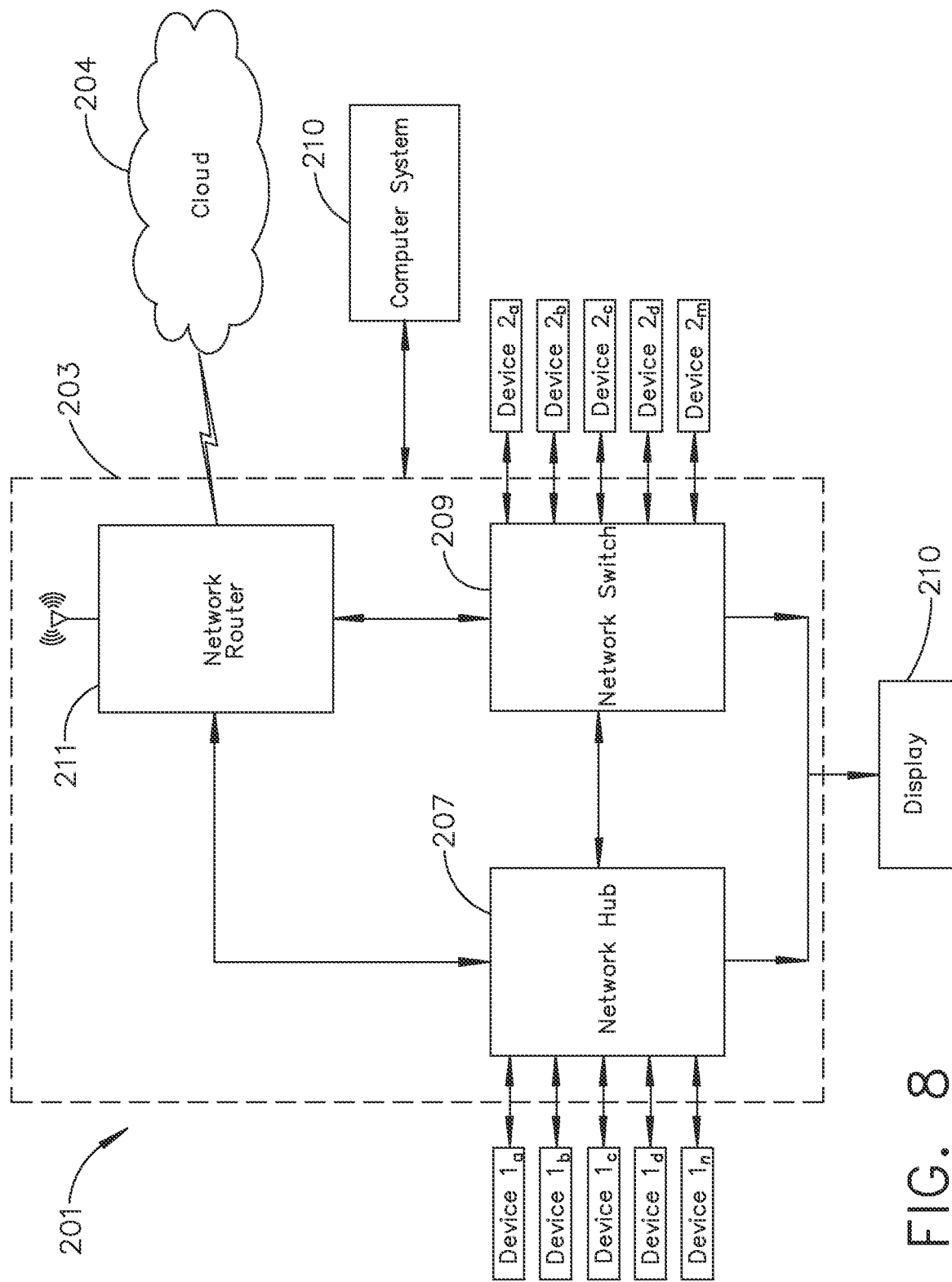
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/internet protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
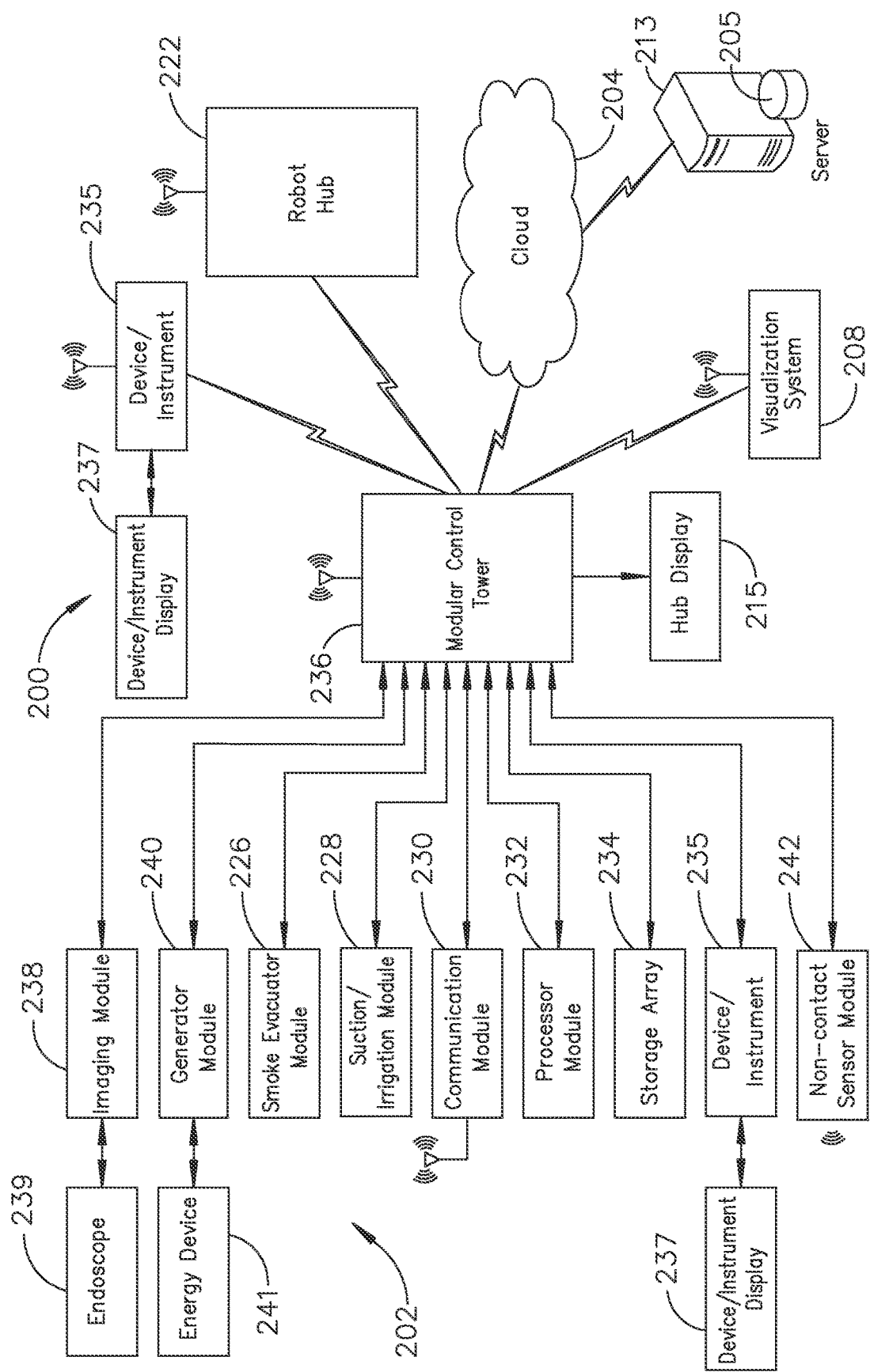
FIG. 9 illustrates a computer-implemented interactive surgical system, in accordance with at least one aspect of the present disclosure.
Figure 10:
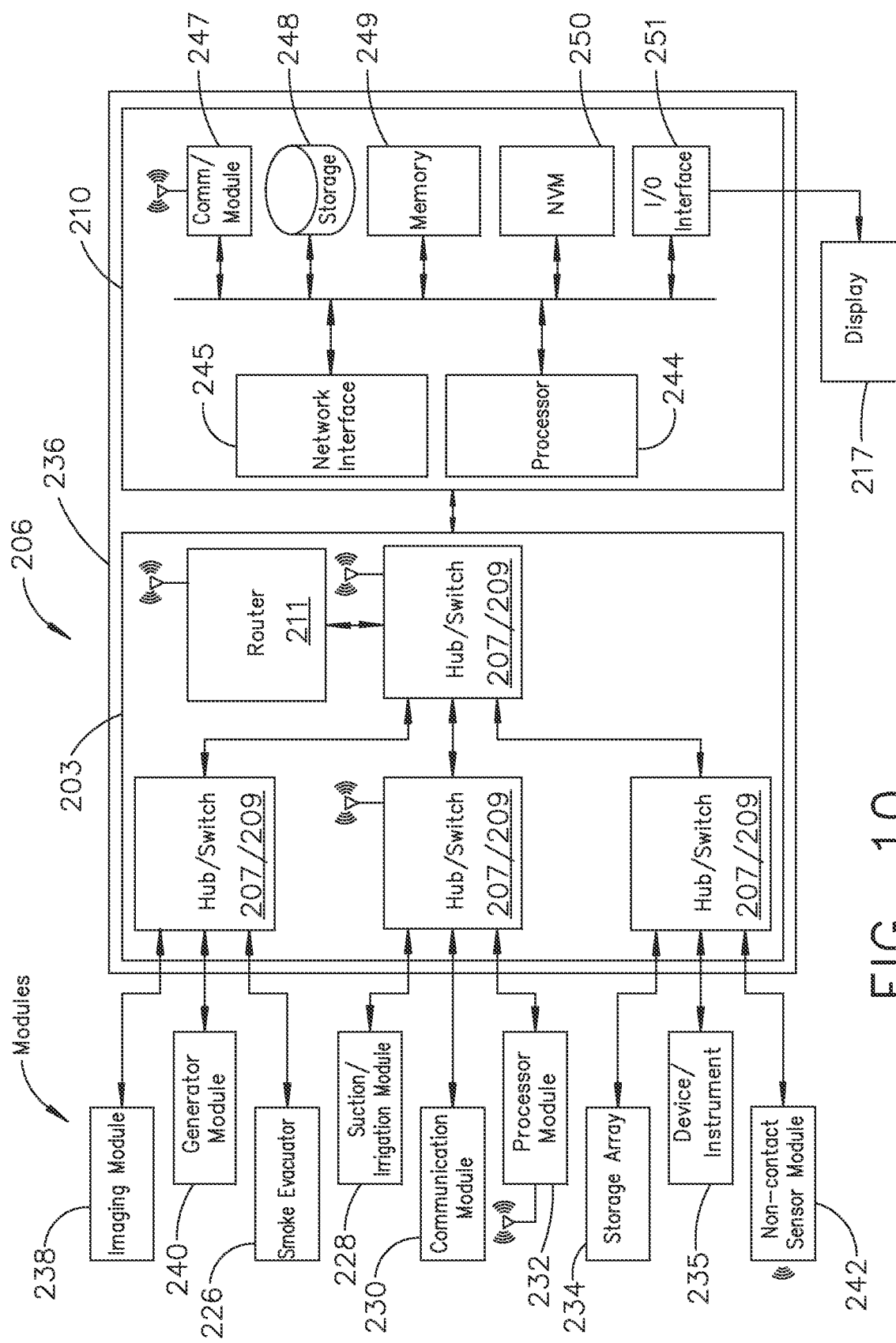
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
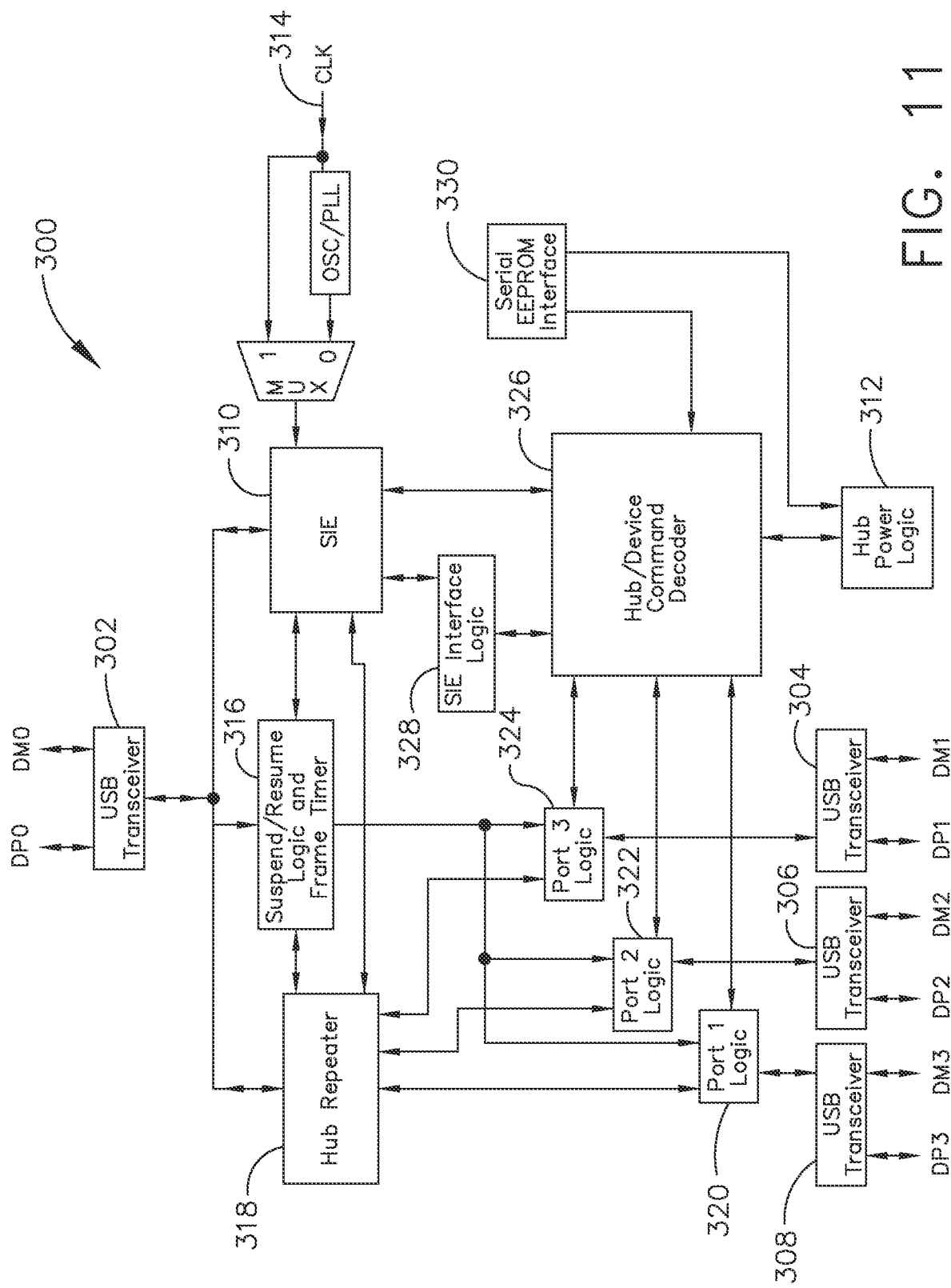
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, according to one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
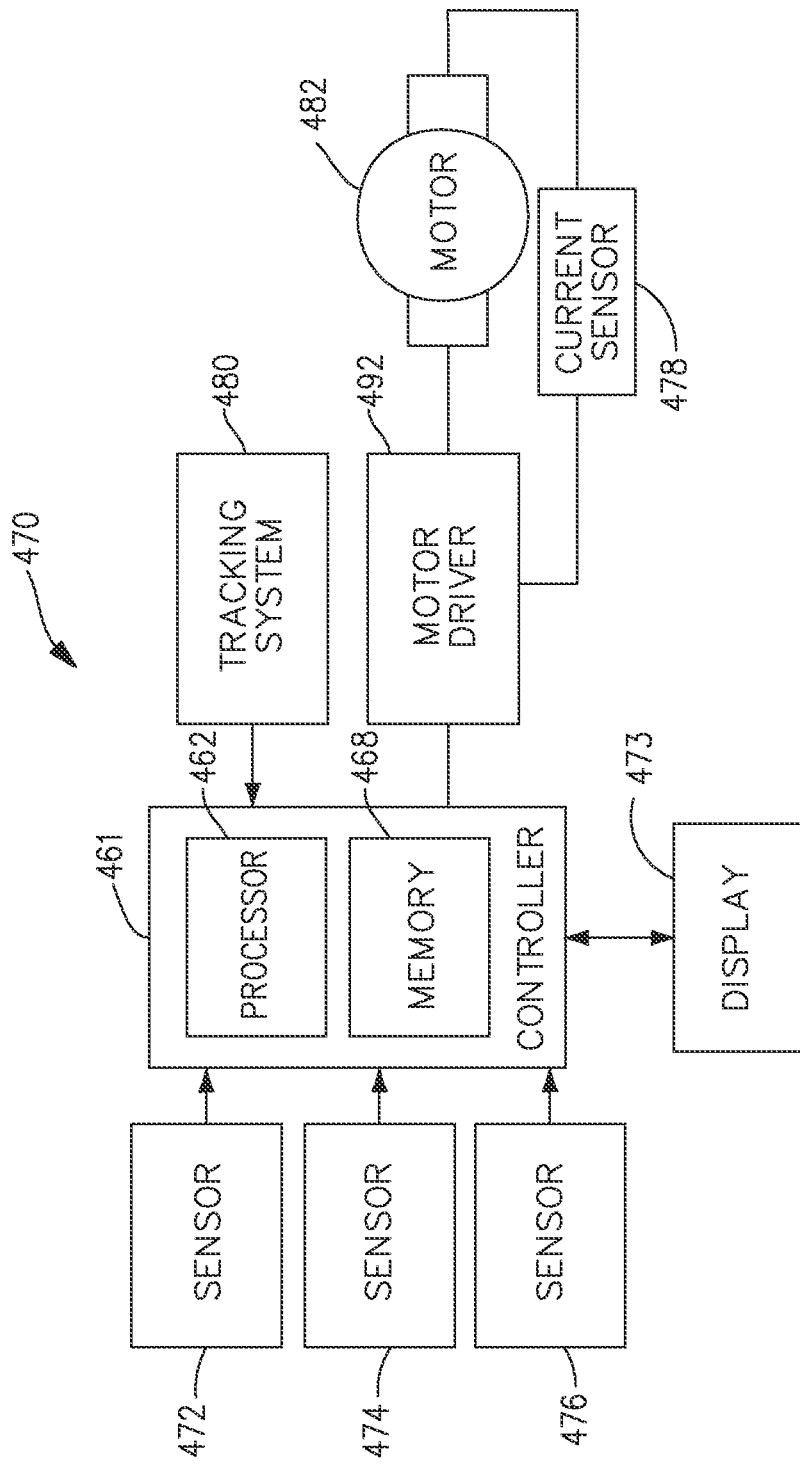
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICK- NESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. Pat. No. 10,881,399, titled TECHNIQUES FOR ADAPTIVE CONTROL OF MOTOR VELOCITY OF A SURGICAL STAPLING AND CUTTING INSTRUMENT, which issued on Jan. 5, 2021, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
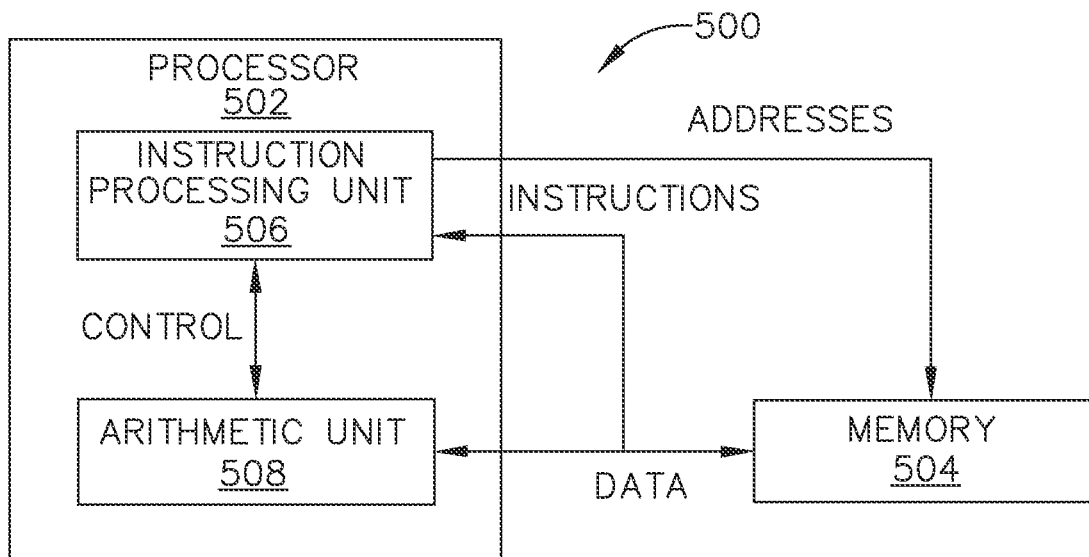
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
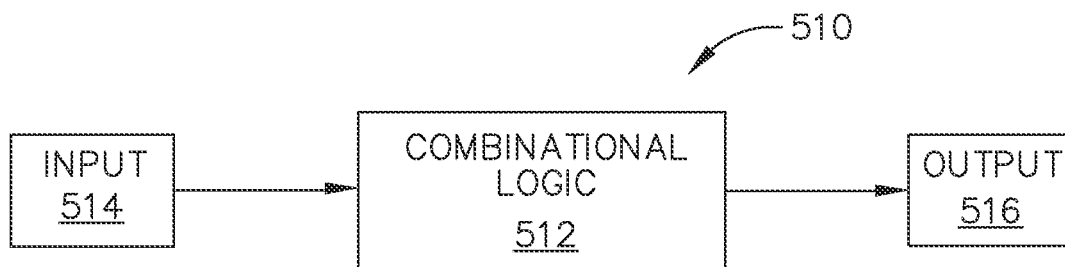
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
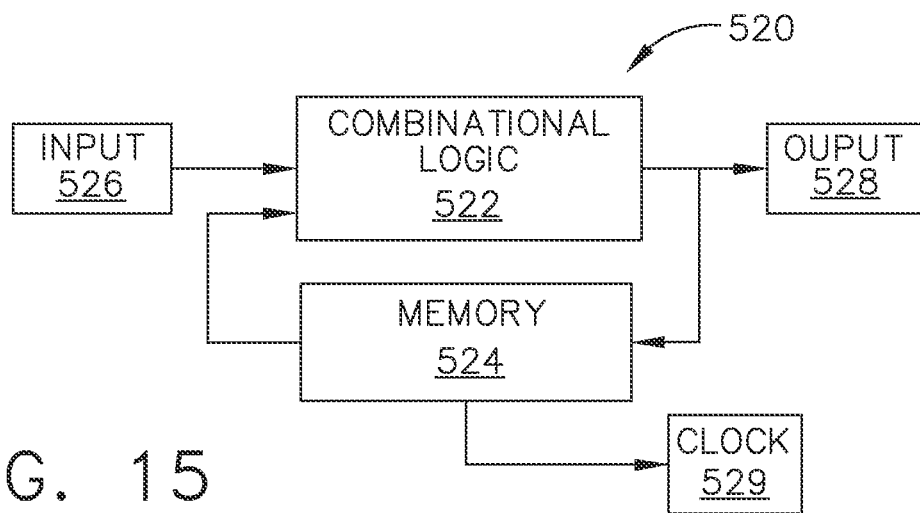
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
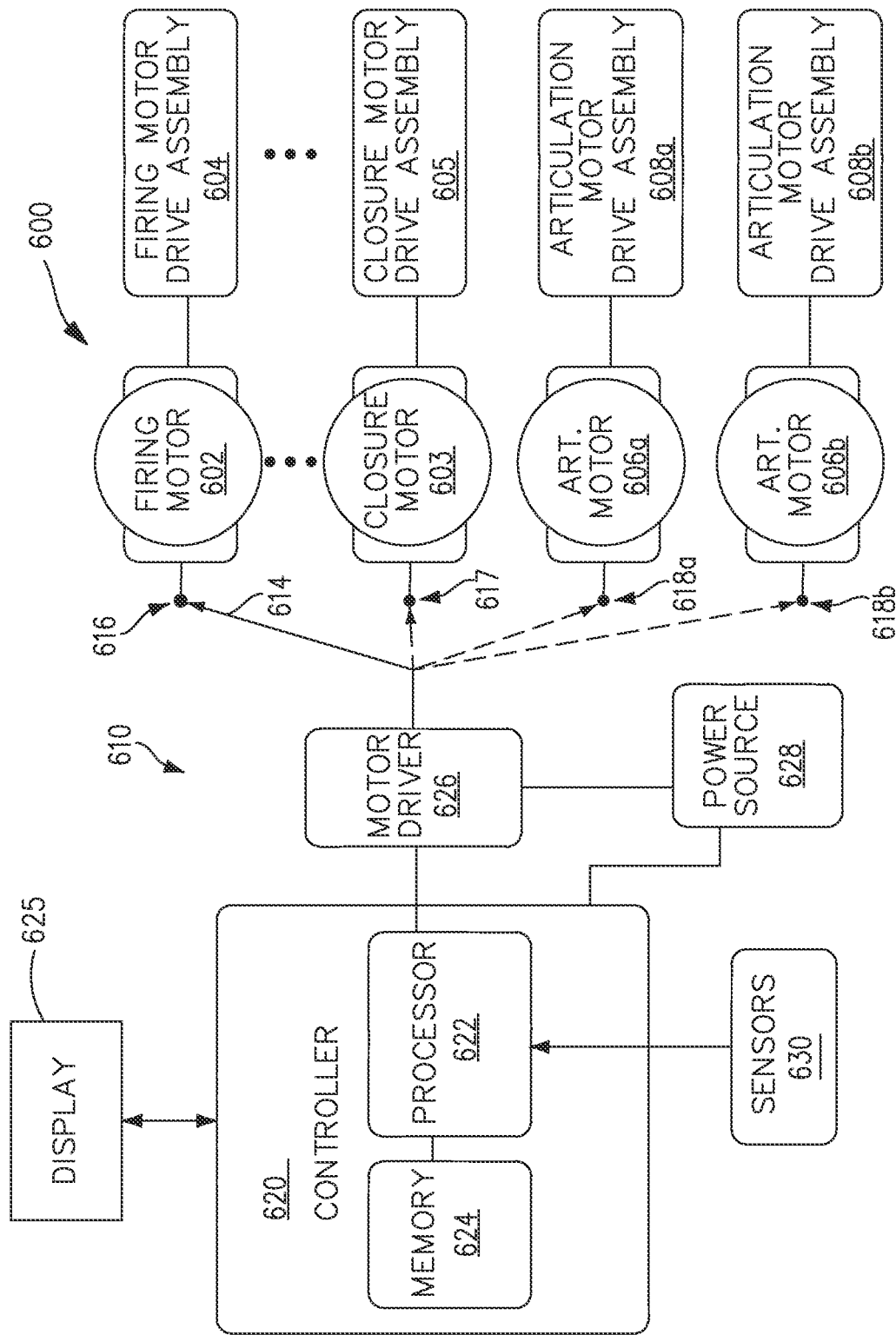
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
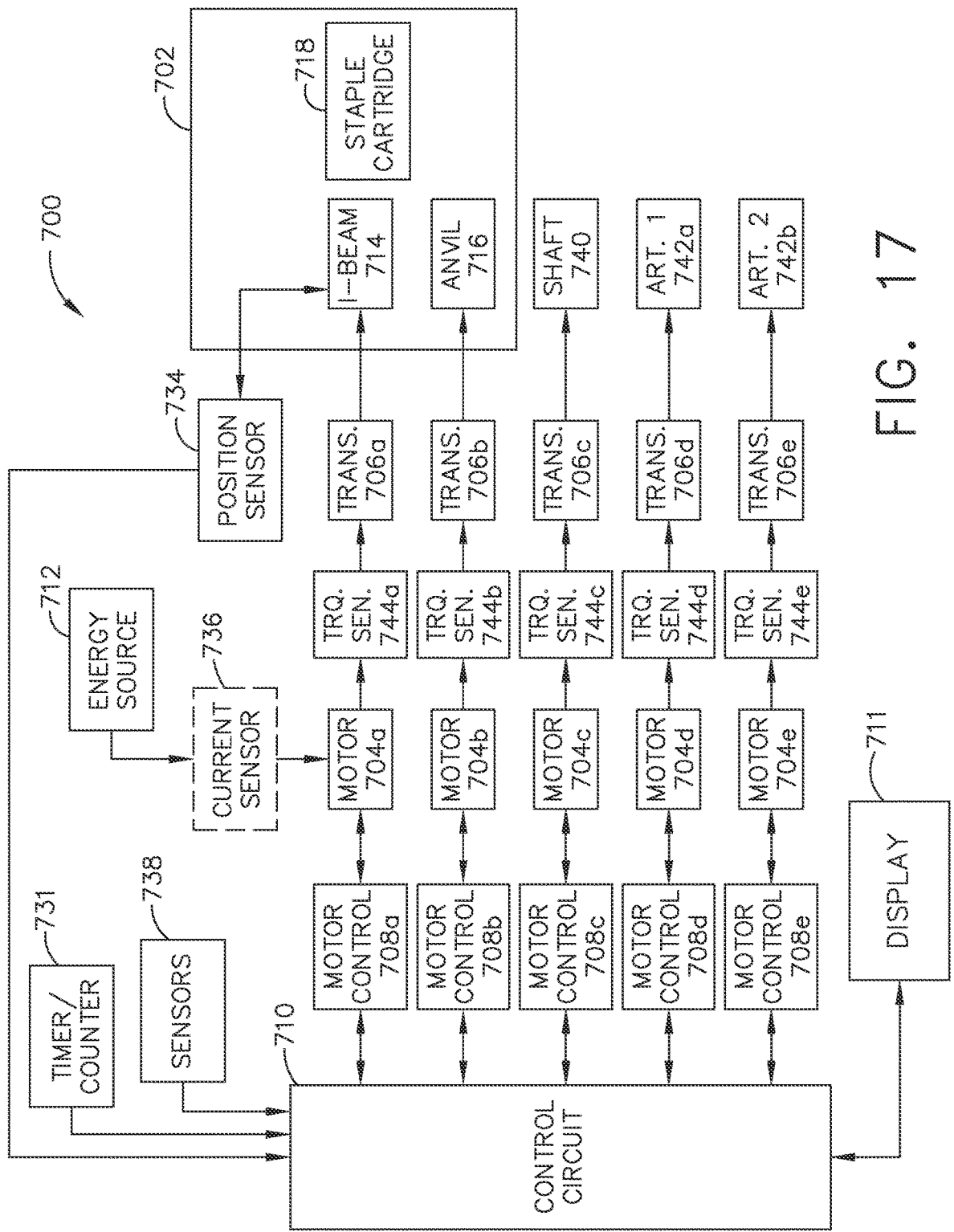
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in a open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the I-beam 714. The transmission 706a comprises movable mechanical elements such as rotating elements and a firing member to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the I-beam 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. Pat. No. 10,932,772, titled CLOSED LOOP VELOCITY CONTROL TECHNIQUES FOR ROBOTIC SURGICAL INSTRUMENT, which issued on Mar. 2, 2021, which is herein incorporated by reference in its entirety.

Figure 18:
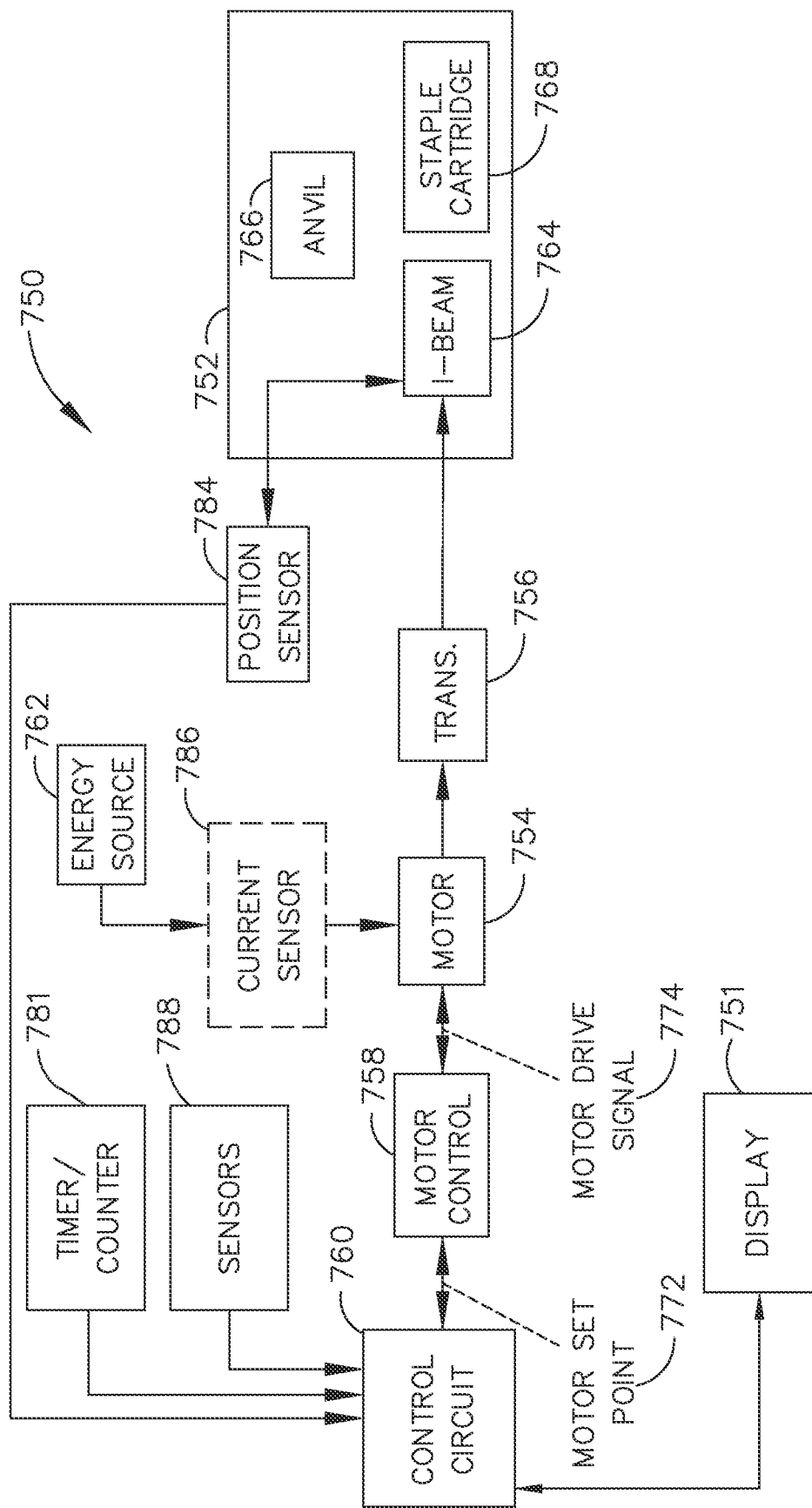
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member according to one aspect of this disclosure. In one aspect, the surgical instrument 750 is programmed to control the distal translation of a displacement member such as the I-beam 764. The surgical instrument 750 comprises an end effector 752 that may comprise an anvil 766, an I-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. Pat. No. 10,743,872, titled SYSTEM AND METHODS FOR CONTROLLING A DISPLAY OF A SURGICAL INSTRUMENT, which issued on Aug. 18, 2020, which is herein incorporated by reference in its entirety.

Figure 19:
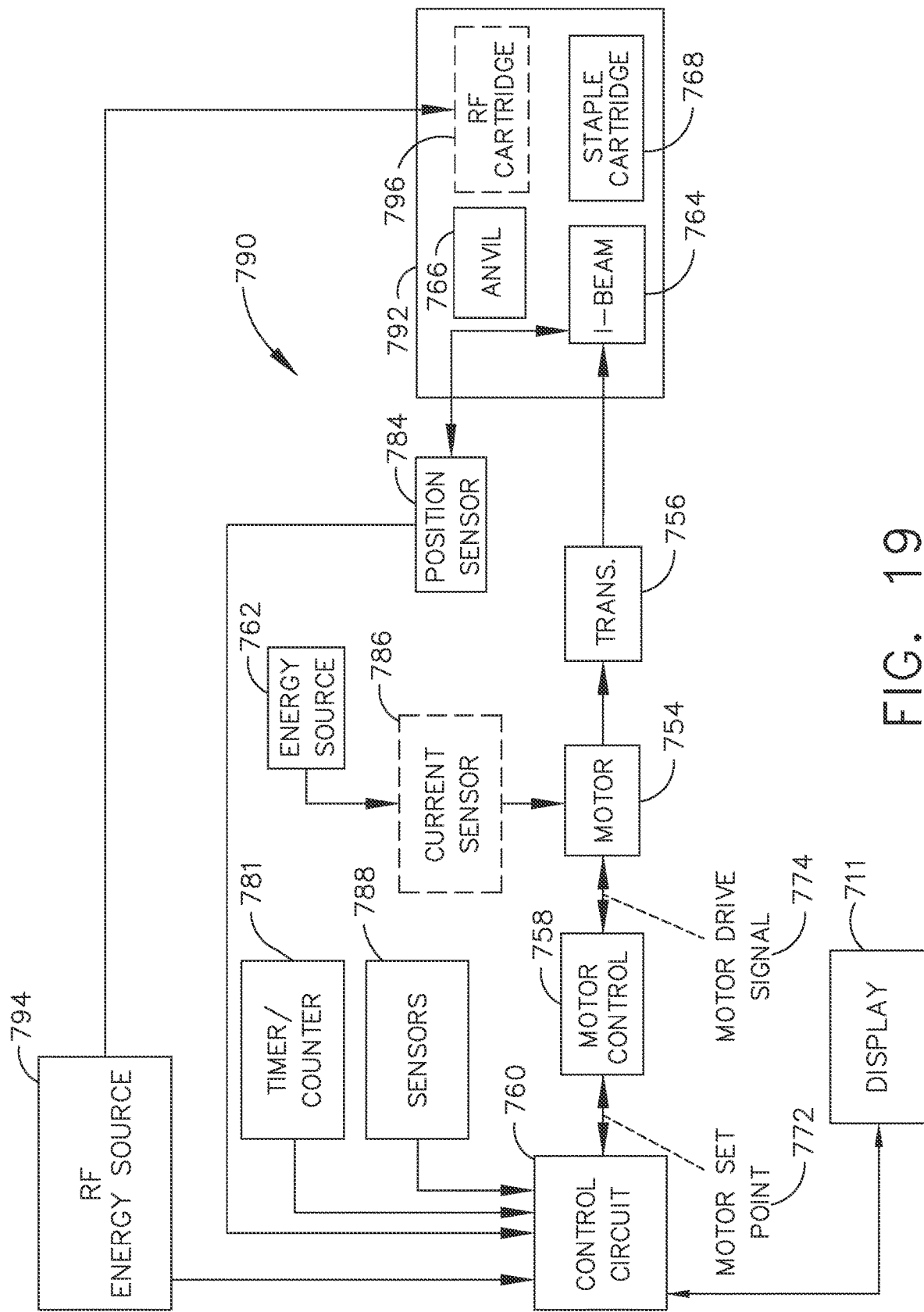
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line).

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly owned U.S. Pat. No. 10,881,399, titled TECHNIQUES FOR ADAPTIVE CONTROL OF MOTOR VELOCITY OF A SURGICAL STAPLING AND CUTTING INSTRUMENT, which issued on Jan. 5, 2021, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. Patent Application Publication No. 2019/0000478, titled SURGICAL SYSTEM COUPLABLE WITH STAPLE CARTRIDGE AND RADIO FREQUENCY CARTRIDGE, AND METHOD OF USING SAME, which published on Jan. 3, 2019, which is herein incorporated by reference in its entirety.

Generator Hardware

Figure 20:
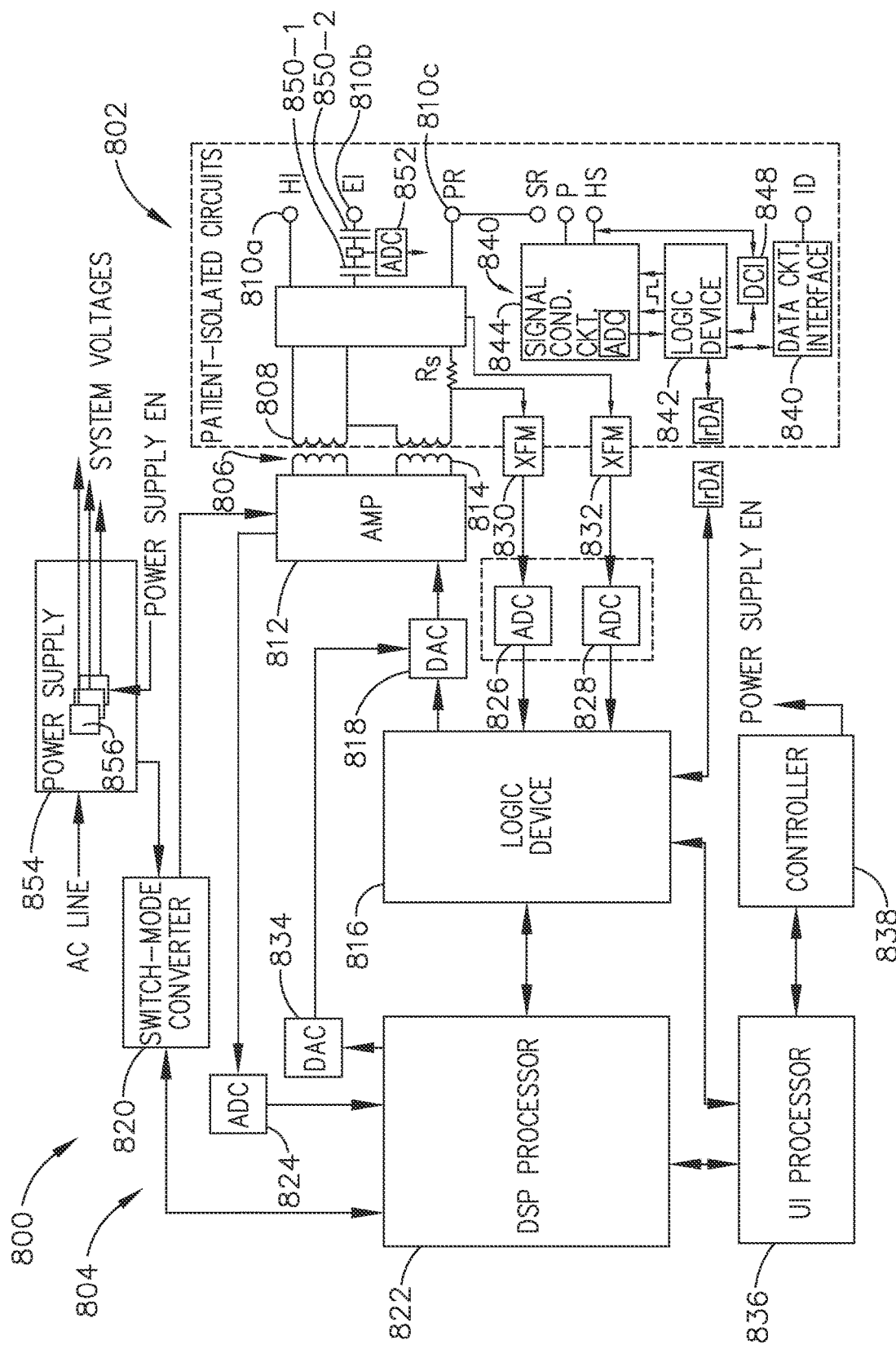
FIG. 20 is a simplified block diagram of a generator configured to provide inductorless tuning, among other benefits, in accordance with at least one aspect of the present disclosure.

FIG. 20 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810a, 810b, 810c for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810a, 810c may output an ultrasonic drive signal (e.g., a 420V root-mean-square (RMS) drive signal) to an ultrasonic surgical instrument, and drive signal outputs 810b, 810c may output an RF electrosurgical drive signal (e.g., a 100V RMS drive signal) to an RF electrosurgical instrument, with the drive signal output 810b corresponding to the center tap of the power transformer 806.

In certain forms, the ultrasonic and electrosurgical drive signals may be provided simultaneously to distinct surgical instruments and/or to a single surgical instrument, such as the multifunction surgical instrument, having the capability to deliver both ultrasonic and electrosurgical energy to tissue. It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue, while the electrosurgical RF energy may be employed for vessel sealing.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, Mass., for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy.

The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, Calif., for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In one form, the instrument interface circuit 840 may comprise a first data circuit interface 846 to enable information exchange between the logic circuit 842 (or other element of the instrument interface circuit 840) and a first data circuit disposed in or otherwise associated with a surgical instrument. In certain forms, for example, a first data circuit may be disposed in a cable integrally attached to a surgical instrument handpiece or in an adaptor for interfacing a specific surgical instrument type or model with the generator 800. The first data circuit may be implemented in any suitable manner and may communicate with the generator according to any suitable protocol, including, for example, as described herein with respect to the first data circuit. In certain forms, the first data circuit may comprise a non-volatile storage device, such as an EEPROM device. In certain forms, the first data circuit interface 846 may be implemented separately from the logic circuit 842 and comprise suitable circuitry (e.g., discrete logic devices, a processor) to enable communication between the logic circuit 842 and the first data circuit. In other forms, the first data circuit interface 846 may be integral with the logic circuit 842.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810b to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

Figure 21:
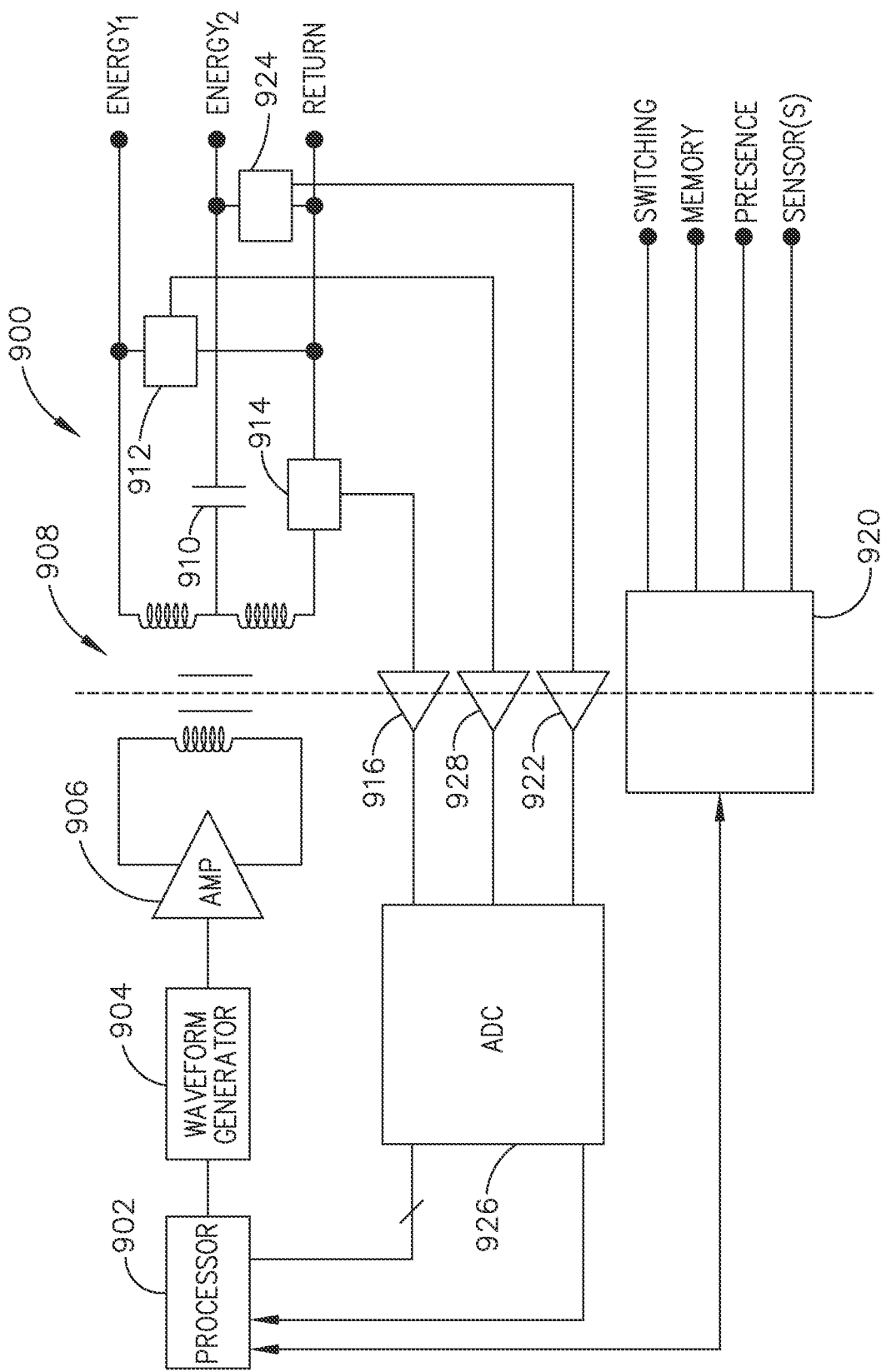
FIG. 21 illustrates an example of a generator, which is one form of the generator of FIG. 20, in accordance with at least one aspect of the present disclosure.

FIG. 21 illustrates an example of a generator 900, which is one form of the generator 800 (FIG. 20). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue.

The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 21. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Pat. No. 10,624,691, titled TECHNIQUES FOR OPERATING GENERATOR FOR DIGITALLY GENERATING ELECTRICAL SIGNAL WAVEFORMS AND SURGICAL INSTRUMENTS, which issued on Apr. 21, 2020, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Data Management and Collection

In one aspect the surgical hub provides data storage capabilities. The data storage includes creation and use of self-describing data including identification features, management of redundant data sets, and storage of the data in a manner of paired data sets which can be grouped by surgery but not necessarily keyed to actual surgical dates and surgeons to maintain data anonymity. The following description incorporates by reference all of the "hub" and "cloud" analytics system hardware and software processing techniques to implement the specific data management and collection techniques described hereinbelow, as incorporated by reference herein. FIGS. 22-41 will be described in the context of the interactive surgical system 100 environment including a surgical hub 106, 206 described in connection FIGS. 1-11 and intelligent instruments and generators described in connection with FIGS. 12-21.

Electronic Medical Record (EMR) Interaction

Figure 22:
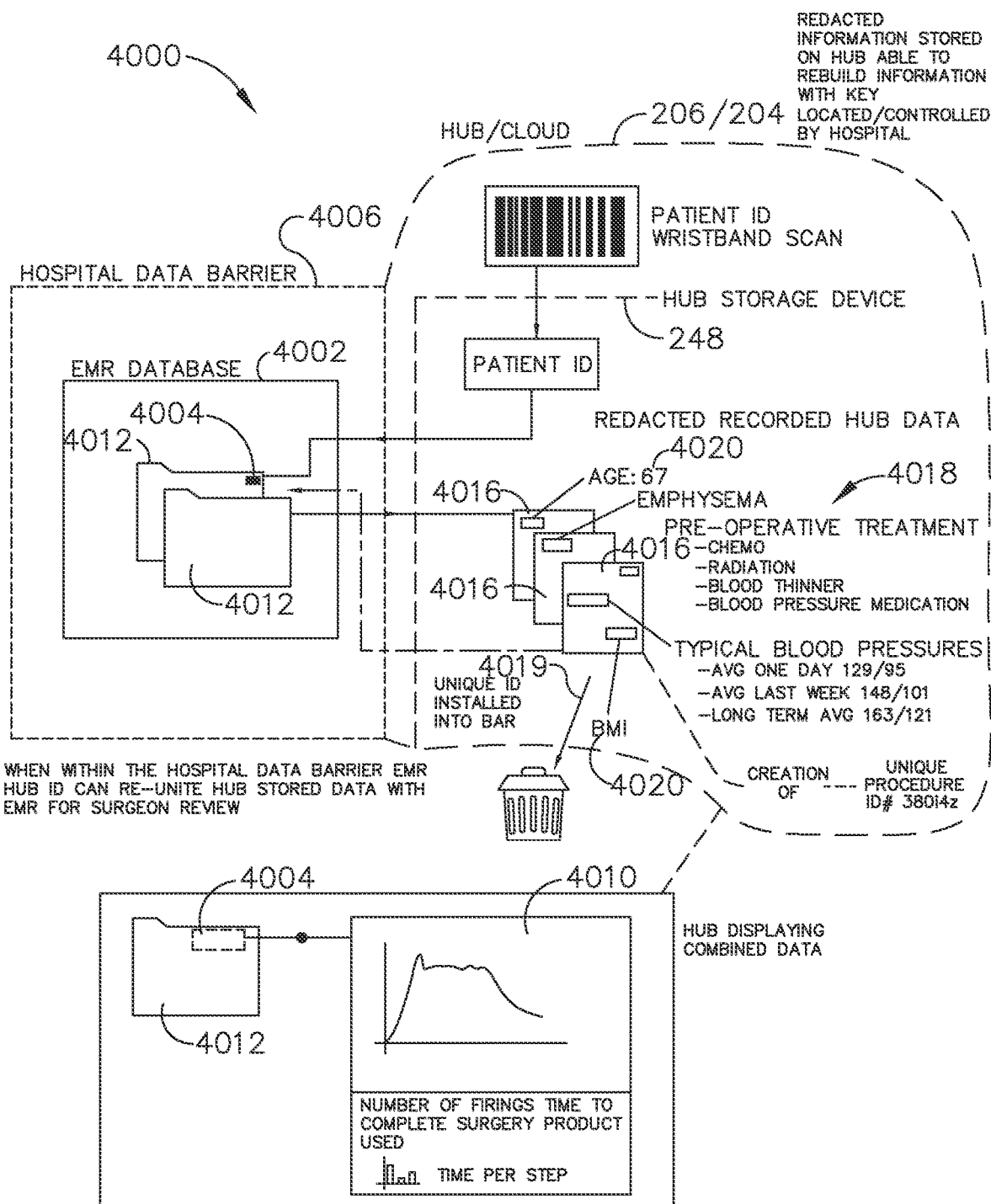
FIG. 22 is a diagram illustrating a technique for interacting with a patient Electronic Medical Record (EMR) database, in accordance with at least one aspect of the present disclosure.

FIG. 22 is a diagram 4000 illustrating a technique for interacting with a patient Electronic Medical Record (EMR) database 4002, according to one aspect of the present disclosure. In one aspect, the present disclosure provides a method of embedding a key 4004 within the EMR database 4002 located within the hospital or medical facility. A data barrier 4006 is provided to preserve patient data privacy and allows the reintegration of stripped and isolated data pairs, as described hereinbelow, from the surgical hub 106, 206 or the cloud 104, 204, to be reassembled. A schematic diagram of the surgical hub 206 is described generally in FIGS. 1-11 and in particular in FIGS. 9-10. Therefore, in the description of FIG. 22, the reader is guided to FIG. 1-11 and in particular FIGS. 9-10 for any implementation details of the surgical hub 206 that may be omitted here for conciseness and clarity of disclosure. Returning to FIG. 22, the method allows the users full access to all the data collected during a surgical procedure and patient information stored in the form of electronic medical records 4012. The reassembled data can be displayed on a monitor 4010 coupled to the surgical hub 206 or secondary monitors but is not permanently stored on any surgical hub storage device 248. The reassembled data is temporarily stored in a storage device 248 located either in the surgical hub 206 or the cloud 204 and is deleted at the end of its use and overwritten to insure it cannot be recovered. The key 4004 in the EMR database 4002 is used to reintegrate anonymized hub data back into full integrated patient electronic medical records 4012 data.

As shown in FIG. 22, the EMR database 4002 is located within the hospital data barrier 4006. The EMR database 4002 may be configured for storing, retrieving, and managing associative arrays, or other data structures known today as a dictionary or hash. Dictionaries contain a collection of objects, or records, which in turn have many different fields within them, each containing data. The patient electronic medical records 4012 may be stored and retrieved using a key 4004 that uniquely identifies the patient electronic medical record 4012, and is used to quickly find the data within the EMR database 4002. The key-value EMR database 4002 system treats the data as a single opaque collection which may have different fields for every record.

Information from the EMR database 4002 may be transmitted to the surgical hub 206 and the patient electronic medical records 4012 data is redacted and stripped before it is sent to an analytics system based either on the hub 206 or the cloud 204. An anonymous data file 4016 is created by redacting personal patient data and stripping relevant patient data 4018 from the patient electronic medical record 4012. As used herein, the redaction process includes deleting or removing personal patient information from the patient electronic medical record 4012 to create a redacted record that includes only anonymous patient data. A redacted record is a record from which sensitive patient information has been expunged. Un-redacted data may be deleted 4019. The relevant patient data 4018 may be referred to herein as stripped/extracted data 4018. The relevant patient data 4018 is used by the surgical hub 206 or cloud 204 processing engines for analytic purposes and may be stored on the storage device 248 of the surgical hub 206 or may be stored on the cloud 204 based analytics system storage device 205. The surgical hub anonymous data file 4016 can be rebuilt using a key 4004 stored in the EMR database 4002 to reintegrate the surgical hub anonymous data file 4016 back into a fully integrated patient electronic medical record 4012. The relevant patient data 4018 that is used in analytic processes may include information such as the patient's diagnoses of emphysema, pre-operative treatment (e.g., chemotherapy, radiation, blood thinner, blood pressure medication, etc.), typical blood pressures, or any data that alone cannot be used to ascertain the identity of the patient. Data 4020 to be redacted includes personal information removed from the patient electronic medical record 4012, may include age, employer, body mass index (BMI), or any data that can be used to ascertain the identify of the patient. The surgical hub 206 creates a unique anonymous procedure ID number (e.g., 380i4z), for example, as described in FIG. 23. Within the EMR database 4002 located in the hospital data barrier 4006, the surgical hub 206 can reunite the data in the anonymous data file 4016 stored on the surgical hub 206 storage device 248 with the data in the patient electronic medical record 4012 stored on the EMR database 4002 for surgeon review. The surgical hub 206 displays the combined patient electronic medical record 4012 on a display or monitor 4010 coupled to the surgical hub 206. Ultimately, un-redacted data is deleted 4019 from the surgical hub 206 storage 248.

Creation of a Hospital Data Barrier, Inside which the Data from Hubs can be Compared Using Non-Anonymized Data and Outside of which the Data has to be Stripped In one aspect, the present disclosure provides a surgical hub 206 as described in FIGS. 9 and 10, for example, where the surgical hub 206 comprises a processor 244; and a memory 249 coupled to the processor 244. The memory 249 stores instructions executable by the processor 244 to interrogate a surgical instrument 235, retrieve a first data set from the surgical instrument 235, interrogate a medical imaging device 238, retrieve a second data set from the medical imaging device 238, associate the first and second data sets by a key, and transmit the associated first and second data sets to a remote network, e.g., the cloud 204, outside of the surgical hub 206. The surgical instrument 235 is a first source of patient data and the first data set is associated with a surgical procedure. The medical imaging device 238 is a second source of patient data and the second data set is associated with an outcome of the surgical procedure. The first and second data records are uniquely identified by the key.

In another aspect, the surgical hub 206 provides a memory 249 storing instructions executable by the processor 244 to retrieve the first data set using the key, anonymize the first data set, retrieve the second data set using the key, anonymize the second data set, pair the anonymized first and second data sets, and determine success rate of surgical procedures grouped by the surgical procedure based on the anonymized paired first and second data sets.

In another aspect, the surgical hub 206 provides a memory 249 storing instructions executable by the processor 244 to retrieve the anonymized first data set, retrieve the anonymized second data set, and reintegrate the anonymized first and second data sets using the key.

In another aspect, the first and second data sets define first and second data payloads in respective first and second data packets.

In various aspects, the present disclosure provides a control circuit to associate the first and second data sets by a key as described above. In various aspects, the present disclosure provides a non-transitory computer readable medium storing computer readable instructions which, when executed, causes a machine to associate the first and second data sets by a key as described above.

During a surgical procedure it would be desirable to monitor data associated with the surgical procedure to enable configuration and operation of instruments used during the procedure to improve surgical outcomes. The technical challenge is to retrieve the data in a manner that maintains the anonymity of the patient to maintain privacy of the data associated with the patient. The data may be used for conglomeration with other data without individualizing the data.

One solution provides a surgical hub 206 to interrogate an electronic medical records database 4002 for patient electronic medical records 4012 data, strip out desirable or relevant patient data 4018 from the patient electronic medical record 4012, and redact any personal information that could be used to identify the patient. The redaction technique removes any information that could be used to correlate the stripped relevant patient data 4018 to a specific patient, surgery, or time. The surgical hub 206 and the instruments 235 coupled to the surgical hub 206 can then be configured and operated based on the stripped relevant patient data 4018.

As disclosed in connection with FIG. 22, extracting (or stripping) relevant patient data 4018 from a patient electronic medical record 4012 while redacting any information that can be used to correlate the patient with the surgery or a scheduled time of the surgery enables the relevant patient data 4018 to be anonymized. The anonymous data file 4016 can then be sent to the cloud 204 for aggregation, processing, and manipulation. The anonymous data file 4016 can be used to configure the surgical instrument 235, or any of the modules shown in FIGS. 9 and 10 or the surgical hub 206 during the surgery based on the extracted anonymous data file 4016.

In one aspect, a hospital data barrier 4006 is created such that inside the data barrier 4006 data from various surgical hubs 206 can be compared using non-anonymized un-redacted data and outside the data barrier 4006 data from various surgical hubs 206 are stripped to maintain anonymity and protect the privacy of the patient and the surgeon. This aspect is discussed further in connection with FIG. 26.

In one aspect, the data from a surgical hub 206 can be exchanged between surgical hubs 206 (e.g., hub-to-hub, switch-to-switch, or router-to-router) to provide in-hospital analysis and display of the data. FIG. 1 shows an example of multiple hubs 106 in communication which each other and with the cloud 104. This aspect also is discussed further in connection with FIG. 26.

In another aspect, an artificial time measure is substituted for a real time clock for all information stored internally within an instrument 235, a robot located in a robot hub 222, a surgical hub 206, and/or hospital computer equipment. The anonymized data, which may include anonymized patient and surgeon data, is transmitted to the server 213 in the cloud 204 and it is stored in the cloud storage device 205 coupled to the server 213. The substitution of an artificial real time clock enables anonymizing the patient data and surgeon data while maintaining data continuity. In one aspect, the instrument 235, robot hub 222, surgical hub 206, and/or the cloud 204 are configured to obscure patient identification (ID) while maintaining data continuity. This aspect is discussed further in connection with FIG. 23.

Within the surgical hub 206, a local decipher key 4004 allows information retrieved from the surgical hub 206 itself to reinstate the real-time information from the anonymized data set located in the anonymous data file 4016. The data stored on the hub 206 or the cloud 204, however, cannot be reinstated to real-time information from the anonymized data set in the anonymous data file 4016. The key 4004 is held locally in the surgical hub 206 computer/storage device 248 in an encrypted format. The surgical hub 206 network processor ID is part of the decryption mechanism such that if the key 4004 and data is removed, the anonymized data set in the anonymous data file 4016 cannot be restored without being on the original surgical hub 206 computer/storage device 248.

Figure 23:
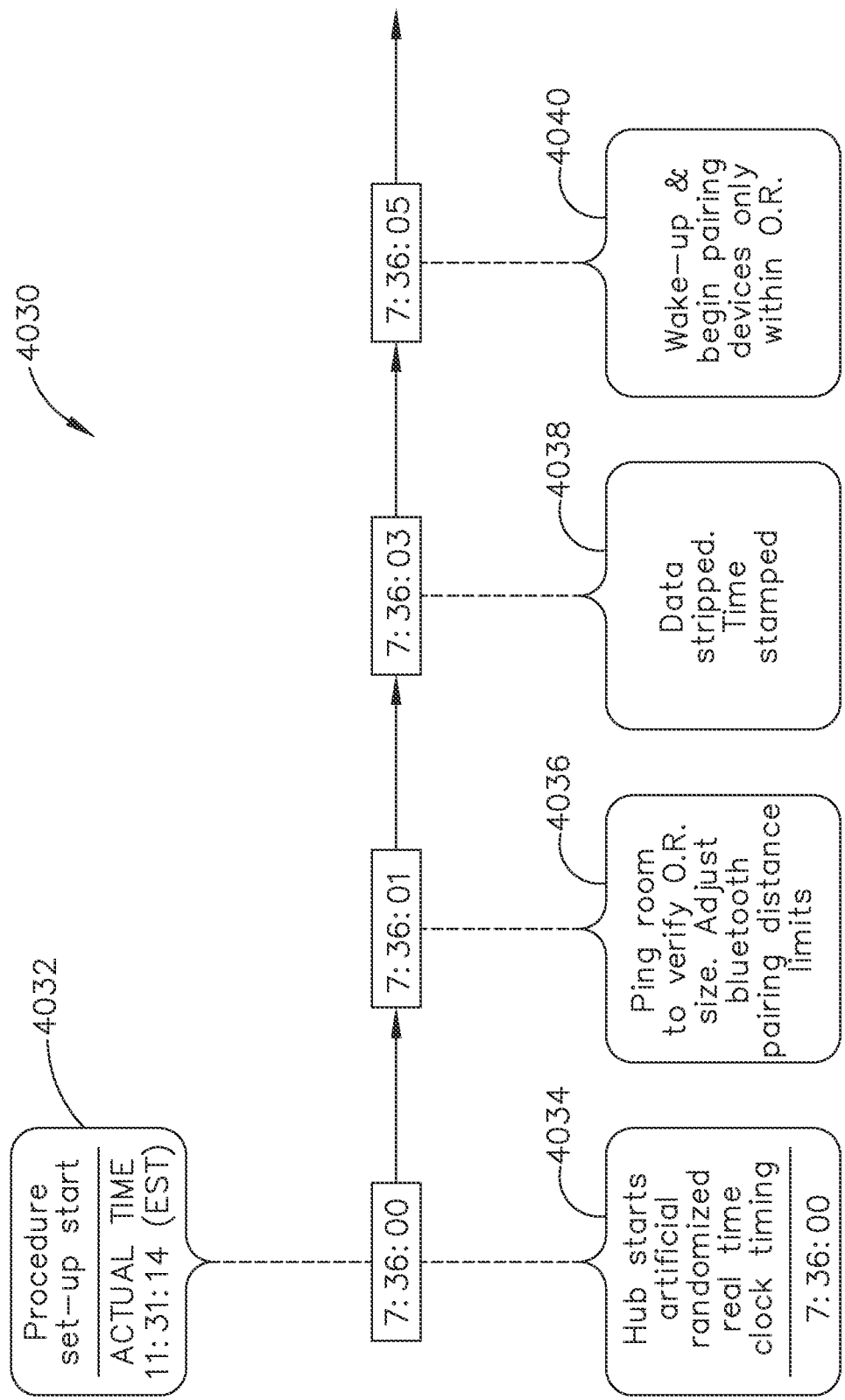
FIG. 23 illustrates a process of anonymizing a surgical procedure by substituting an artificial time measure for a real time clock for all information stored internally within the instrument, robot, surgical hub, and/or hospital computer equipment, in accordance with at least one aspect of the present disclosure.

Substituting Artificial Time Measure for Real Time Clock for all Internally Stored Information and Sent to the Cloud as a Means to Anonymizing the Patient and Surgeon Data FIG. 23 illustrates a process 4030 of anonymizing a surgical procedure by substituting an artificial time measure for a real time clock for all information stored internally within the instrument, robot, surgical hub, and/or hospital computer equipment, according to one aspect of the present disclosure. As shown in FIG. 23, the surgical procedure set-up start time 4032 was scheduled to begin at an actual time of 11:31:14 (EST) based on a real time clock. At the stated procedure set-up start time 4032, the surgical hub 206 starts 4034 an artificial randomized real time clock timing scheme at artificial real time at 07:36:00. The surgical hub 206 then ultrasonically pings 4036 the operating theater (e.g., sends out a burst of ultrasound and listens for the echo when it bounces off the perimeter walls of an operating theater (e.g., a fixed, mobile, temporary, or field the operating room) as described in connection with FIG. 24 to verify the size of the operating theater and to adjust short range wireless, e.g., Bluetooth, pairing distance limits at artificial real time 07:36:01. At artificial real time 07:36:03, the surgical hub 206 strips 4038 the relevant data and applies a time stamp to the stripped data. At artificial real time 07:36:05, the surgical hub 206 wakes up and begins pairing 4040 only devices located within the operating theater as verified using the ultrasonic pinging 4036 process.

Figure 24:
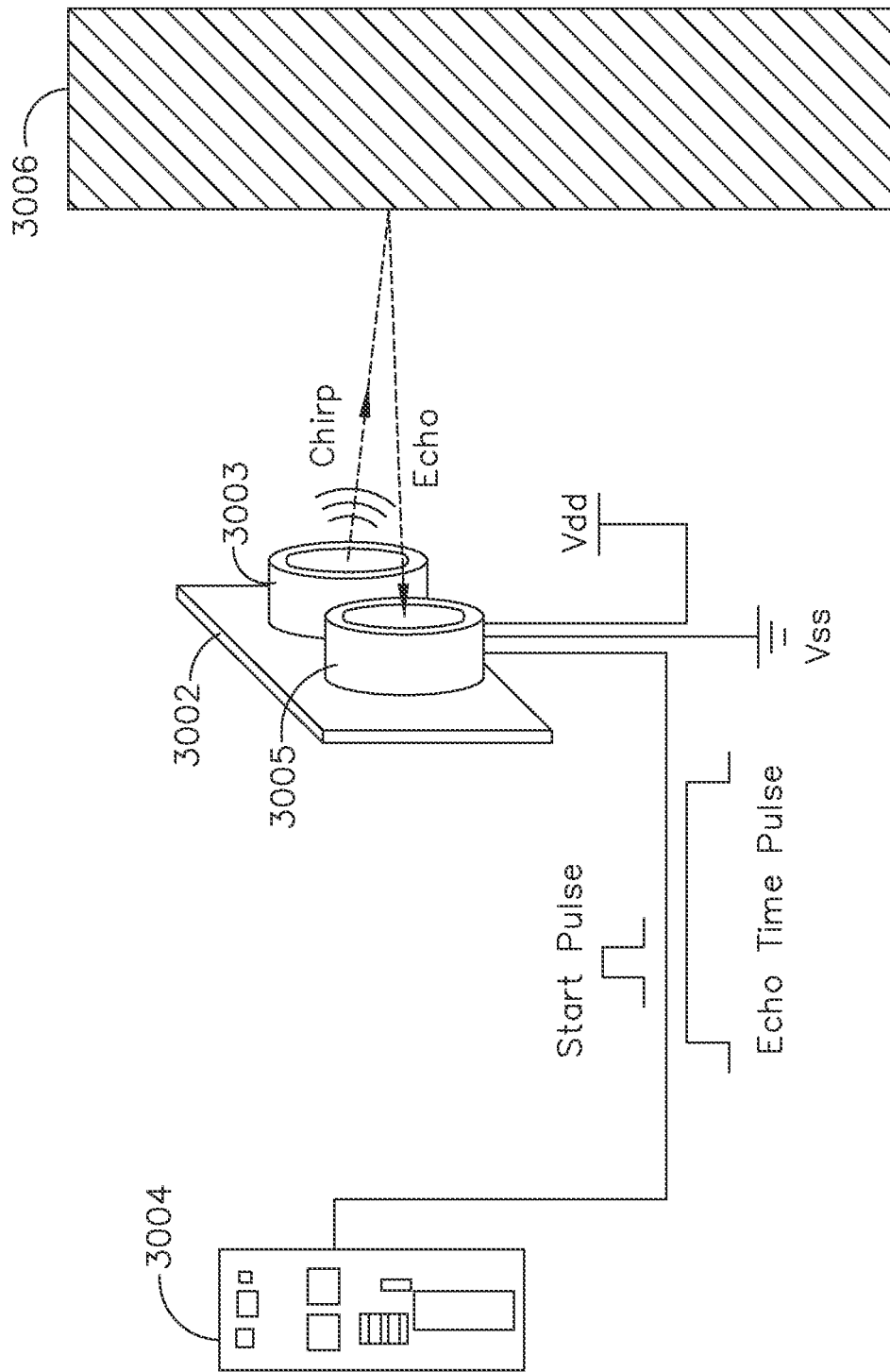
FIG. 24 illustrates ultrasonic pinging of an operating room wall to determine a distance between a surgical hub and the operating room wall, in accordance with at least one aspect of the present disclosure.

FIG. 24 illustrates ultrasonic pinging of an operating room wall to determine a distance between a surgical hub and the operating room wall, in accordance with at least one aspect of the present disclosure. With reference also to FIG. 2, the spatial awareness of the surgical hub 206 and its ability to map an operating room for potential components of the surgical system allows the surgical hub 206 to make autonomous decisions about whether to include or exclude such potential components as part of the surgical system, which relieves the surgical staff from dealing with such tasks. Furthermore, the surgical hub 206 is configured to make inferences about, for example, the type of surgical procedure to be performed in the operating room based on information gathered prior to, during, and/or after the performance of the surgical procedure. Examples of gathered information include the types of devices that are brought into the operating room, time of introduction of such devices into the operating room, and/or the devices sequence of activation.

In one aspect, the surgical hub 206 employs the operating-room mapping module, such as, for example, the non-contact sensor module 242 to determine the bounds of the surgical theater (e.g., a fixed, mobile, or temporary operating room or space) using either ultrasonic or laser non-contact measurement devices.

Referring now to FIG. 24, ultrasound based non-contact sensors 3002 can be employed to scan the operating theater by transmitting a burst of ultrasound and receiving the echo when it bounces off a perimeter wall 3006 of an operating theater to determine the size of the operating theater and to adjust short range wireless, e.g., Bluetooth, pairing distance limits. In one example, the non-contact sensors 3002 can be Ping ultrasonic distance sensors, as illustrated in FIG. 24.

FIG. 24 shows how an ultrasonic sensor 3002 sends a brief chirp with its ultrasonic speaker 3003 and makes it possible for a micro-controller 3004 of the operating-room mapping module to measure how long the echo takes to return to the ultrasonic sensor's ultrasonic microphone 3005. The micro-controller 3004 has to send the ultrasonic sensor 3002 a pulse to begin the measurement. The ultrasonic sensor 3002 then waits long enough for the micro-controller program to start a pulse input command. Then, at about the same time the ultrasonic sensor 3002 chirps a 40 kHz tone, it sends a high signal to the micro-controller 3004. When the ultrasonic sensor 3002 detects the echo with its ultrasonic microphone 3005, it changes that high signal back to low. The micro-controller's pulse input command measures the time between the high and low changes, and stores it measurement in a variable. This value can be used along with the speed of sound in air to calculate the distance between the surgical hub 106 and the operating-room wall 3006.

In one example, a surgical hub 206 can be equipped with four ultrasonic sensors 3002, wherein each of the four ultrasonic sensors is configured to assess the distance between the surgical hub 206 and a wall of the operating room 3000. A surgical hub 206 can be equipped with more or less than four ultrasonic sensors 3002 to determine the bounds of an operating room.

Other distance sensors can be employed by the operating-room mapping module to determine the bounds of an operating room. In one example, the operating-room mapping module can be equipped with one or more photoelectric sensors that can be employed to assess the bounds of an operating room. In one example, suitable laser distance sensors can also be employed to assess the bounds of an operating room. Laser based non-contact sensors may scan the operating theater by transmitting laser light pulses, receiving laser light pulses that bounce off the perimeter walls of the operating theater, and comparing the phase of the transmitted pulse to the received pulse to determine the size of the operating theater and to adjust short range wireless, e.g., Bluetooth, pairing distance limits.

Stripping Out Data from Images and Connected Smart Instrument Data to Allow Conglomeration but not Individualization In one aspect, the present disclosure provides a data stripping method which interrogates the electronic patient records provided, extracts the relevant portions to configure and operate the surgical hub and instruments coupled to the surgical hub, while anonymizing the surgery, patient, and all identifying parameters to maintain patient privacy.

With reference now back to FIG. 23 and also to FIGS. 1-11 to show interaction with an interactive surgical system 100 environment including a surgical hub 106, 206, once the size of the operating theater has been verified and Bluetooth pairing is complete, based on artificial real time, the computer processor 244 of the surgical hub 206 begins stripping 4038 data received from the modules coupled to the surgical hub 206. In one example, the processor 244 begins stripping 4083 images received from the imaging module 238 and connected smart instruments 235, for example. Stripping 4038 the data allows conglomeration of the data but not individualization of the data. This enables stripping 4038 the data identifier, linking the data, and monitoring an event while maintaining patient privacy by anonymizing the data.

With reference to FIGS. 1-24, in one aspect, a data stripping 4038 method is provided. In accordance with the data stripping 4038 method, the surgical hub 206 processor 244 interrogates the patient records stored in the surgical hub database 238 and extracts the relevant portions of the patient records to configure and operate the surgical hub 206 and its instruments 235, robots, and other modular devices, e.g., modules. The data stripping 4038 method anonymizes the surgical procedure, patient, and all identifying parameters associated with the surgical procedure. Stripping 4038 the data on the fly ensures that at no time the data is correlated to a specific patient, surgical procedure, surgeon, time or other possible identifier that can be used to correlate the data.

The data may be stripped 4038 for compilation of the base information at a remote cloud 204 database storage device 205 coupled to the remote server 213. The data stored in the database storage device 248 can be used in advanced cloud based analytics, as described in U.S. Provisional Patent Application Ser. No. 62/611,340, filed Dec. 28, 2017, titled CLOUD-BASED MEDICAL ANALYTICS, which is incorporated herein by reference in its entirety. A copy of the information with data links intact also can be stored into the patient EMR database 4002 (FIG. 22). For example, the surgical hub 206 may import patient tissue irregularities or co-morbidities to add to an existing data set stored in the database 248. The data may be stripped 4038 before the surgery and/or may be stripped 4038 as the data is transmitted to the cloud 204 database storage device 205 coupled to the remote server 213.

Figure 25:
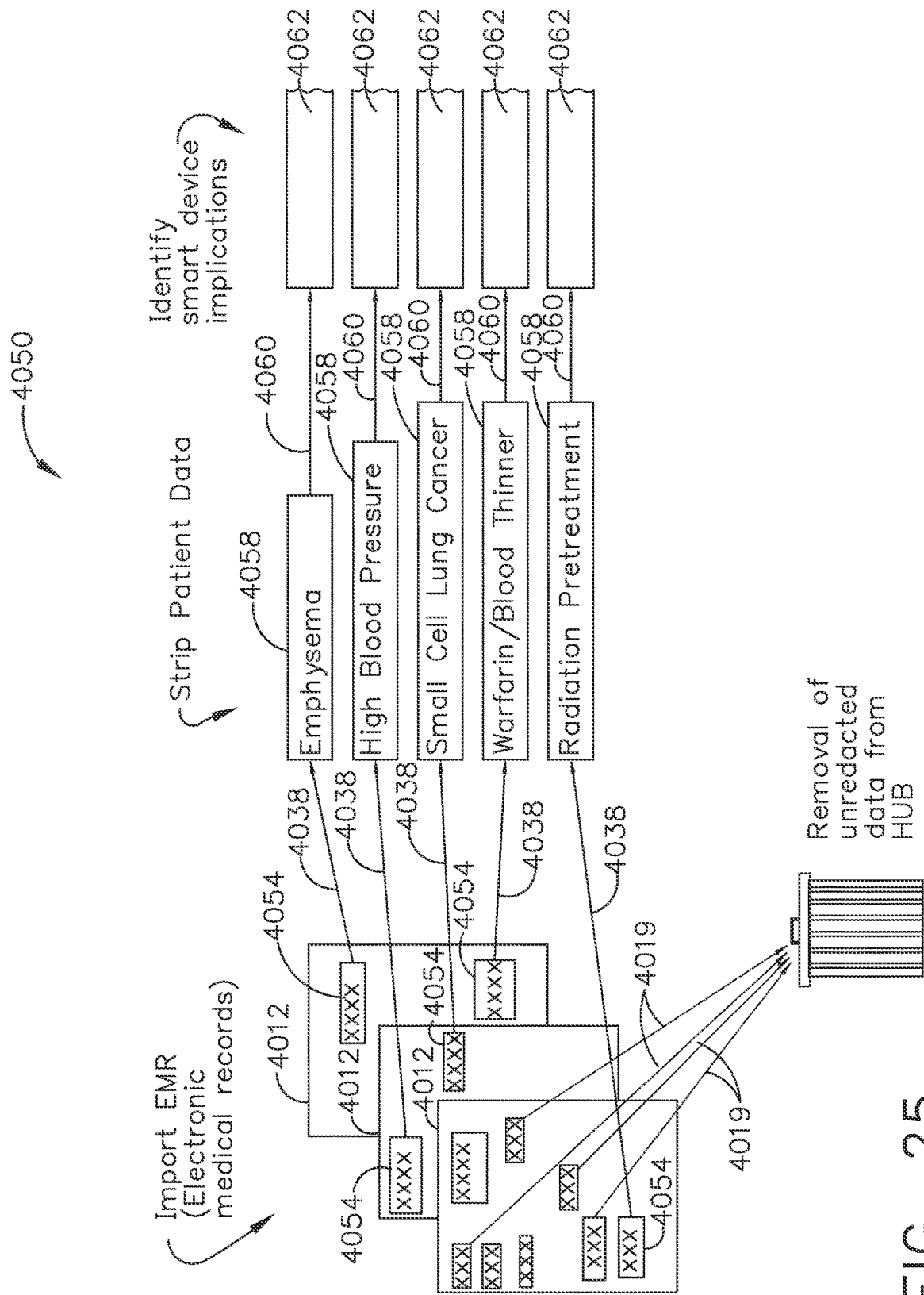
FIG. 25 illustrates a diagram depicting the process of importing patient data stored in an Electronic Medical Record (EMR) database, stripping the patient data, and identifying smart device implications, in accordance with at least one aspect of the present disclosure.

With continued reference to FIGS. 1-11 and 22-24, FIG. 25 is a diagram 4050 depicting the process of importing patient electronic medical records 4012 containing surgical procedure and relevant patient data 4018 stored in the EMR database 4002, stripping 4038 the relevant patient data 4018 from the imported medical records 4012, and identifying 4060 smart device implications 4062, or inferences, according to one aspect of the present disclosure. As shown in FIG. 25, the patient electronic medical records 4012, containing information stored in the patient EMR database 4002, are retrieved from the EMR database 4002, imported into the surgical hub 206, and stored in the surgical hub 206 storage device 248. Un-redacted data is removed or deleted 4019 from the patient electronic medical records 4012 before they are stored in the surgical hub 206 storage device 248 as an anonymous data file 4016 (FIG. 22). The relevant patient data 4018 is then stripped 4038 from the medical records 4012 to remove the desired relevant patient data 4018 and delete 4019 un-redacted data to maintain patient anonymity. In the illustrated example, the stripped data 4058 includes emphysema, high blood pressure, small lung cancer, warfarin/blood thinner, and/or radiation pretreatment. The stripped data 4058 is employed to identify 4060 smart device implications while maintaining patient anonymity as described hereinbelow.

Although the surgical procedure data and relevant patient data 4018 is described as being imported from patient electronic medical records 4012 stored in the EMR database 4002, in various aspects, the surgical procedure data and relevant patient data 4018 may be retrieved from a modular device coupled to the surgical hub 206 before being stored in the EMR database 4002. For example, the surgical hub 206 may interrogate the module to retrieve the surgical procedure data and relevant patient data 4018 from the module. As described herein, a module includes an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242, among other modules as illustrated in FIGS. 3 and 8-10.

For example, the anonymized stripped data 4058 may be employed to identify 4060 catastrophic failures of instruments, and other smart devices, and may initiate an automatic archive process and submission of data for further implications analysis. For example, the implication of detecting a counterfeit component or adapter on an original equipment manufacturer (OEM) device would be to initiate documentation of the component and recording of the results and outcome of its use. For example, the surgical hub 206 may execute situational awareness algorithms as described in connection FIG. 41. In one aspect, the surgical hub 206 may initially receive or identify a variety of implications 4062 that are derived from anonymized stripped data 4058. The surgical hub 206 is configured to control the instruments 235, or other modules, so that they operate correspondingly to the derived implications 4062. In one example, the surgical hub 206 control logic identifies that (i) lung tissue may be more fragile than normal (e.g., due to emphysema), (ii) hemostasis issues are more likely (e.g., due to high blood pressure and/or the patient being on a blood thinner, such as warfarin), (iii) cancer may be more aggressive (e.g., due to the target of the procedure being a small cell lung cancer), and (iv) lung tissue may be stiffer and more prone to fracture (e.g., due to the patient having received a radiation pretreatment). The control logic or processor 244 of the surgical hub 206 then interprets how this data impacts the instruments 235, or other modules, so that the instruments 235 are operated consistently with the data and then communicates the corresponding adjustments to each of the instruments 235.

In one example relating to a stapler type of surgical instrument 235, based on the implications 4062 identified 4060 from the anonymized stripped data 4058, the control logic or processor 244 of the surgical hub 206 may (i) notify the stapler to adjust the compression rate threshold parameter, (ii) adjust the surgical hub 206 visualization threshold value to quantify the bleeding and internal parameters, (iii) notify the combo generator module 240 of the lung tissue and vessel tissue types so that the power and generator module 240 control algorithms are adjusted accordingly, (iv) notify the imaging module 238 of the aggressive cancer tag to adjust the margin ranges accordingly, (v) notify the stapler of the margin parameter adjustment needed (the margin parameter corresponds to the distance or amount of tissue around the cancer that will be excised), and (vi) notify the stapler that the tissue is potentially fragile. Furthermore, the anonymized stripped data 4058, upon which the implications 40602 are based, is identified by the surgical hub 206 and is fed into the situational awareness algorithm (see FIG. 41). Examples include, without limitations, thoracic lung resection, e.g., segmentectomy, among others.

Figure 26:
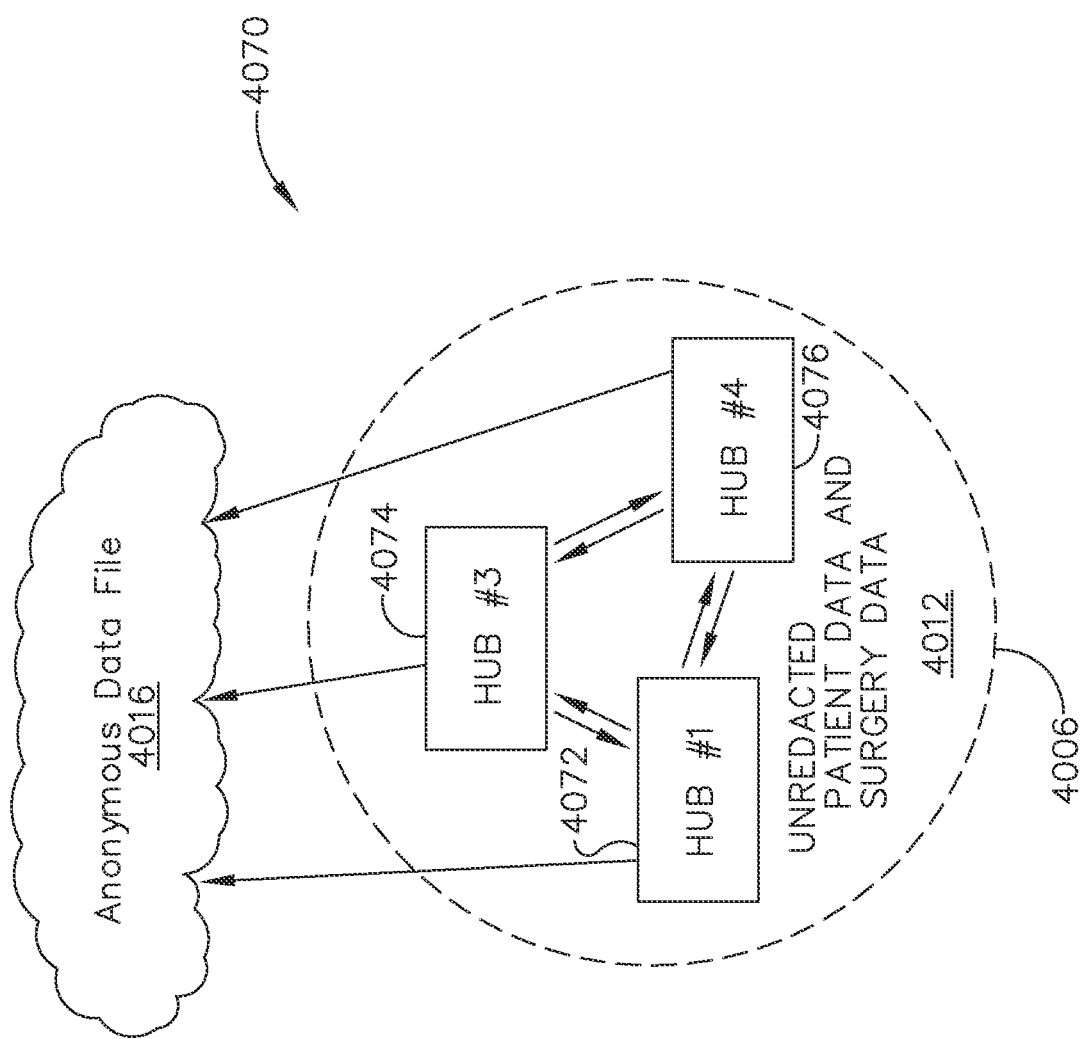
FIG. 26 illustrates the application of cloud based analytics to redacted and stripped patient data and independent data pairs, in accordance with at least one aspect of the present disclosure.

FIG. 26 is a diagram 4070 illustrating the application of cloud based analytics to un-redacted data, stripped relevant patient data 4018, and independent data pairs, according to one aspect of the present disclosure. As shown, multiple surgical hubs Hub #1 4072, Hub #3 4074, and Hub #4 4076 are located within the hospital data barrier 4006 (see also FIG. 22). The un-redacted patient electronic medical record 4012 including patient data and surgery related data may be used and exchanged between the surgical hubs: Hub #1 4072, Hub #3 4074, and Hub #4 4076 located within the hospital data barrier 4006. Prior to transmitting the un-redacted patient electronic medical record 4012 containing patient data and surgery related data outside the hospital data barrier 4006, however, the patient electronic medical record 4012 patient data is redacted and stripped to create an anonymous data file 4016 containing anonymized information for further analysis and processing of the redacted/stripped data by a cloud based analytic processes in the cloud 204.

Figure 27:
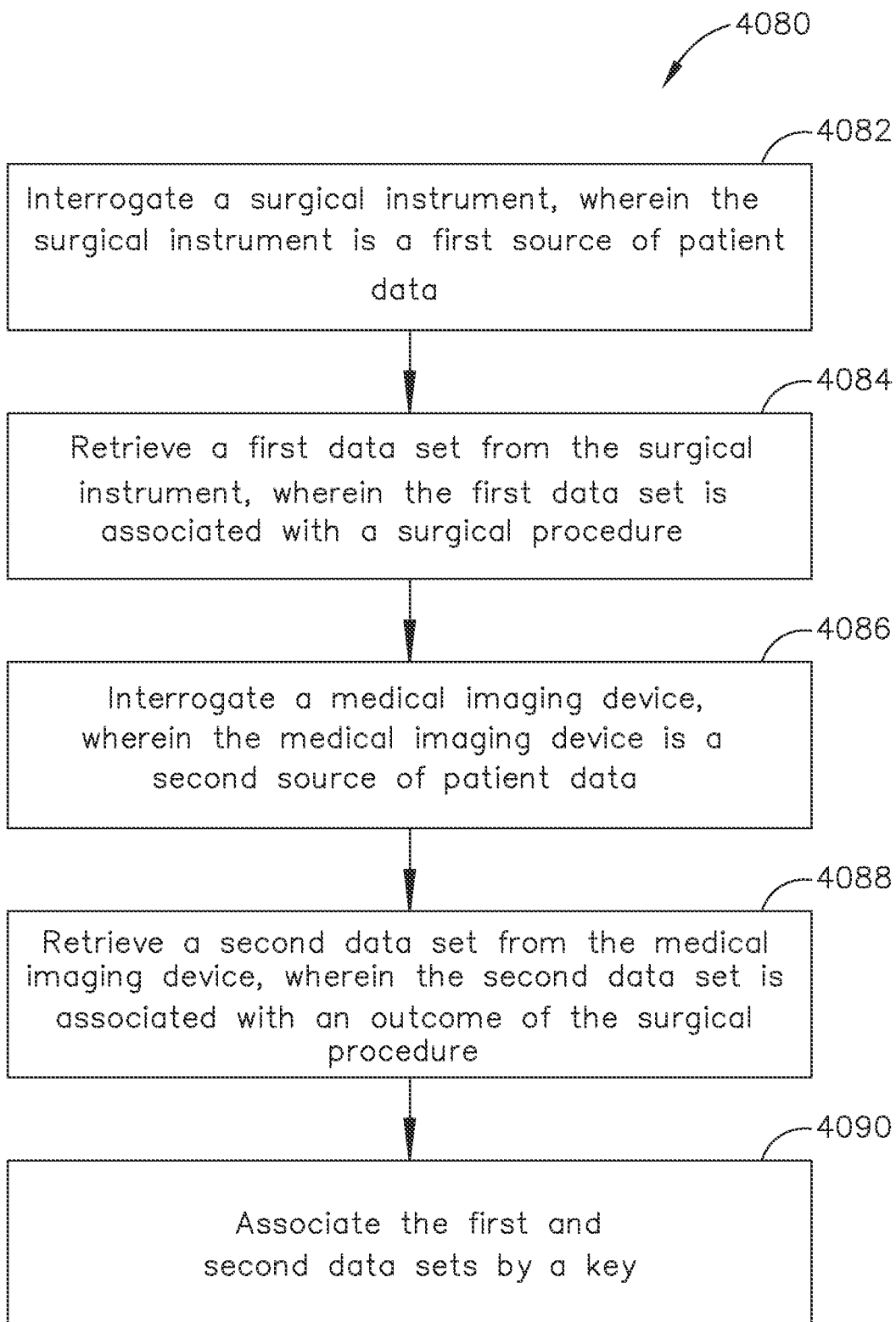
FIG. 27 is a logic flow diagram of a process depicting a control program or a logic configuration for associating patient data sets from first and second sources of data, in accordance with at least one aspect of the present disclosure.

FIG. 27 is a logic flow diagram 4080 of a process depicting a control program or a logic configuration for associating patient data sets from first and second sources of data, according to one aspect of the present disclosure. With reference to FIG. 27 and with reference also to FIGS. 1-11 to show interaction with an interactive surgical system 100 environment including a surgical hub 106, 206, in one aspect, the present disclosure provides a surgical hub 206, comprising a processor 244; and a memory 249 coupled to the processor 244. The memory 249 stores instructions executable by the processor 244 to interrogate 4082 a surgical instrument 235, retrieve 4084 a first data set from the surgical instrument 235, interrogate 4086 a medical imaging device 238, retrieve 4088 a second data set from the medical imaging device 238, associate 4090 the first and second data sets by a key, and transmit the associated first and second data sets to a remote network outside of the surgical hub 206. The surgical instrument 235 is a first source of patient data and the first data set is associated with a surgical procedure. The medical imaging device 238 is a second source of patient data and the second data set is associated with an outcome of the surgical procedure. The first and second data records are uniquely identified by the key.

In another aspect, the surgical hub 206 provides a memory 249 storing instructions executable by the processor 244 to retrieve the first data set using the key, anonymize the first data set, retrieve the second data set using the key, anonymize the second data set, pair the anonymized first and second data sets, and determine success rate of surgical procedures grouped by the surgical procedure based on the anonymized paired first and second data sets.

In another aspect, the surgical hub 206 provides a memory 249 storing instructions executable by the processor 244 to retrieve the anonymized first data set, retrieve the anonymized second data set, and reintegrate the anonymized first and second data sets using the key.

Figure 28:
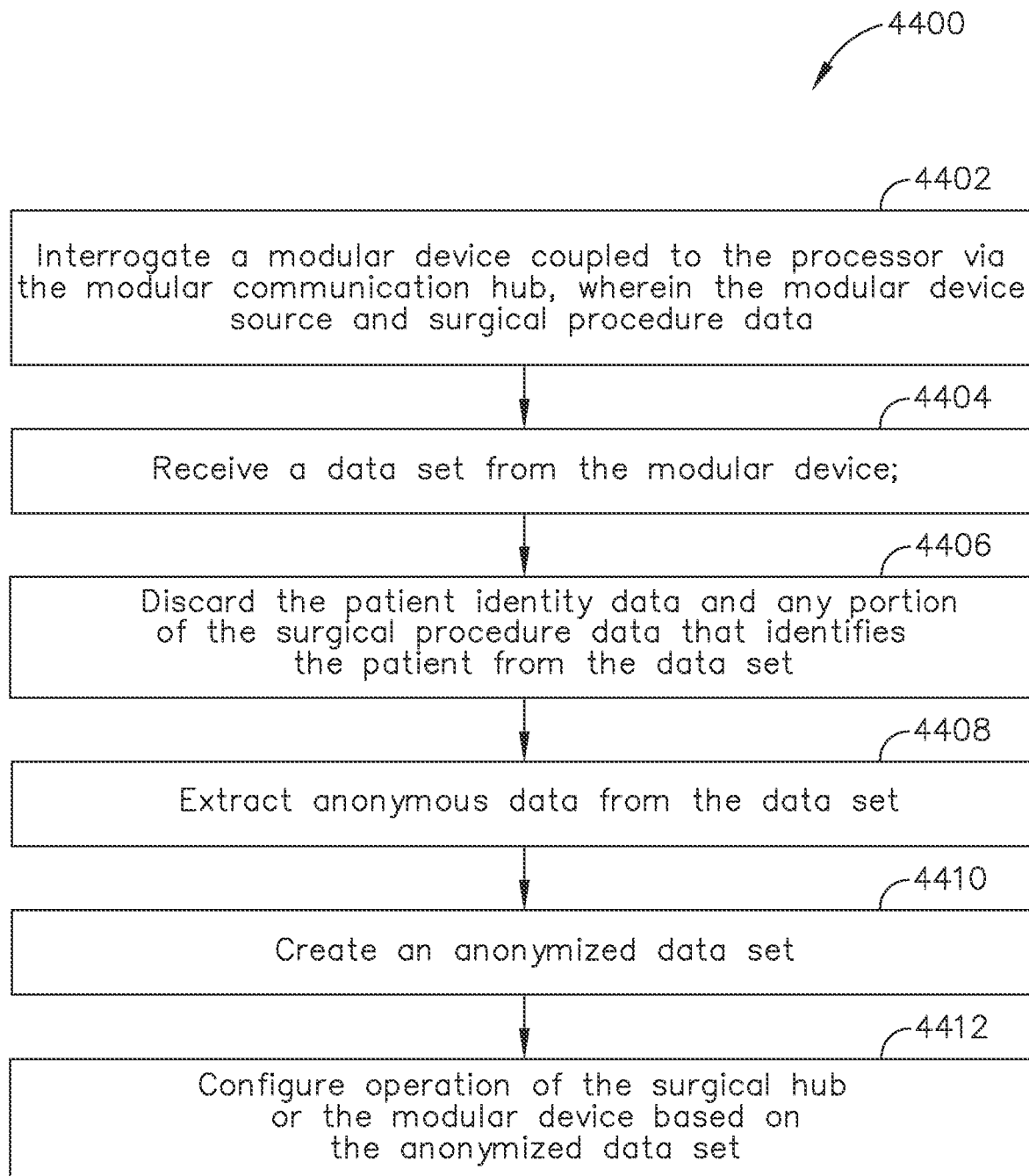
FIG. 28 is a logic flow diagram of a process depicting a control program or a logic configuration for stripping data to extract relevant portions of the data to configure and operate the surgical hub and modules (e.g., instruments) coupled to the surgical hub, in accordance with at least one aspect of the present disclosure.

FIG. 28 is a logic flow diagram of a process 4400 depicting a control program or a logic configuration for stripping data to extract relevant portions of the data to configure and operate the surgical hub 206 and modules (e.g., instruments 235) coupled to the surgical hub 206, according to one aspect of the present disclosure. With reference to FIG. 28 and with reference also to FIGS. 1-11 to show interaction with an interactive surgical system 100 environment including a surgical hub 106, 206, in one aspect, the surgical hub 206 may be configured to interrogate a module coupled to surgical hub 206 for data, and strip the data to extract relevant portions of the data to configure and operate the surgical hub 206 and modules (e.g., instruments 235) coupled to the surgical hub 206 and anonymize the surgery, patient, and other parameters that can be used to identify the patient to maintain patient privacy. According to the process 4400, in one aspect the present disclosure provides a surgical hub 206 including a processor 244, a modular communication hub 203 coupled to the processor 244, where the modular communication hub 203 is configured to connect modular devices located in one or more operating theaters to the surgical hub 206. The processor 244 is coupled to a memory 249, where the memory 249 stores instructions executable by the processor 244 to cause the processor to interrogate 4402 a modular device coupled to the processor 244 via the modular communication hub 203. The modular device is a source of data sets that include patient identity data and surgical procedure data. The processor 244 receives 4404 a data set from the modular device. The processor 244 discards 4406 the patient identity data and any portion of the surgical procedure data that identifies the patient from the data set. The processor 244 extracts 4408 anonymous data from the data set and creates 4410 an anonymized data set. The processor 244 configures 4412 the operation of the surgical hub 206 or the modular device based on the anonymized data set.

In another aspect, where the anonymized data set includes catastrophic failure of a modular device, the memory 249 stores instructions executable by the processor 244 to initiate automatic archiving and submission of data for implications analysis based on the catastrophic failure of the modular device. In another aspect, the memory 249 stores instructions executable by the processor 244 to detect counterfeit component information from the anonymized data set. In another aspect, the memory 249 stores instructions executable by the processor 244 to derive implications of the modular device from the anonymized data set and the memory 249 stores instructions executable by the processor 244 to configure the modular device to operate based on the derived implications or to configure the surgical hub based on the derived implications. In another aspect, the memory 249 stores instructions executable by the processor 244 to conglomerate the anonymized data. In another aspect, the memory 249 stores instructions executable by the processor 244 to extract the anonymized data prior to storing the received data in a storage device coupled to the surgical hub. In another aspect, the memory 249 stores instructions executable by the processor to transmit the anonymized data to a remote network outside of the surgical hub, compile the anonymized data at the remote network, and store a copy of the data set from the modular device in a patient electronic medical records database.

Storage of Data Creation and Use of Self-Describing Data Including Identification Features In one aspect, the present disclosure provides self-describing data packets generated at the issuing instrument and including identifiers for all devices that handled the packet. The self description allows the processor to interpret the data in the self-describing packet without knowing the data type in advance prior to receipt of the self-describing packet. The data applies to every data point or data string and includes the type of data, the source of the self-describing packet, the device identification that generated the packet, the units, the time of generation of the packet, and an authentication that the data contained in the packet is unaltered. When the processor (in the device or the surgical hub) receives an unexpected packet and verifies the source of the packet, the processor alters the collection techniques to be ready for any subsequent packets from that source.

With reference also to FIGS. 1-11 to show interaction with an interactive surgical system 100 environment including a surgical hub 106, 206, during a surgical procedure being performed in a surgical hub 206 environment, the size and quantity of data being generated by surgical devices 235 coupled to the surgical hub 206 can become quite large. Also, data exchanged between the surgical devices 235 and/or the surgical hub 206 can become quite large.

One solution provides a techniques for minimizing the size of the data and handling the data within a surgical hub 206 by generating a self-describing packet. The self-describing packet is initially assembled by the instrument 235 that generated it. The packet is then ordered and encrypted b generating an encryption certificate which is unique for each data packet. The data is then communicated from the instrument 235 via encrypted wired or wireless protocols and stored on the surgical hub 206 for processing and transmission to the cloud 204 analytics engine. Each self-describing data packet includes an identifier to identify the specific instrument that generated it and the time it was generated. A surgical hub 206 identifier is added to the packet when the packet is received by the surgical hub 206.

In one aspect, the present disclosure provides a surgical hub 206 comprising a processor 244 and a memory 249 coupled to the processor 244. The memory 249 storing instructions executable by the processor 244 to receive a first data packet from a first source, receive a second data packet from a second source, associate the first and second data packets, and generate a third data packet comprising the first and second data payloads. The first data packet comprises a first preamble, a first data payload, a source of the first data payload, and a first encryption certificate. The first preamble defines the first data payload and the first encryption certificate verifies the authenticity of the first data packet. The second data packet comprises a second preamble, a second data payload, a source of the second data payload, and a second encryption certificate. The second preamble defines the second data payload and the second encryption certificate verifies the authenticity of the second data packet.

In another aspect, the memory 249 stores instructions executable by the processor 244 to determine that a data payload is from a new source, verify the new source of the data payload, and alter a data collection process at the surgical hub to receive subsequent data packets from the new source.

In another aspect, the memory 249 stores instructions executable by the processor 244 to associate the first and second data packets based on a key. In another aspect, the memory 249 stores instructions executable by the processor 244 to anonymize the data payload of the third data packet. In another aspect, the memory 249 stores instructions executable by the processor 244 to receive an anonymized third data packet and reintegrate the anonymized third data packet into the first and second data packets using the key.

In various aspects, the present disclosure provides a control circuit to receive and process data packets as described above. In various aspects, the present disclosure provides a non-transitory computer-readable medium storing computer readable instructions, which when executed, causes a machine to receive and process data packets as described above.

In other aspects, the present disclosure a method of generating a data packet comprising self-describing data. In one aspect, a surgical instrument includes a processor and a memory coupled to the processor, a control circuit, and/or a computer-readable medium configured to generate a data packet comprising a preamble, a data payload, a source of the data payload, and an encryption certificate. The preamble defines the data payload and the encryption certificate verifies the authenticity of the data packet. In various aspects, the data packet may be generated by any module coupled to the surgical hub. Self-describing data packets minimize data size and data handing in the surgical hub.

In one aspect, the present disclosure provides a self-describing data packet generated at an issuing device (e.g., instrument, tool, robot). The self-describing data packet comprises identifiers for all devices that handle the data packet along a communication path; a self description to enable a processor to interpret that data contained in the data packet without having been told in advance of receipt of the data packet along a path; data for every data point or data string; and type of data, source of data, device IDs that generated the data, units of the data, time of generation, and authentication that the data packet is unaltered. In another aspect, when a processor receives a data packet from an unexpected source and verifies the source of the data, the processor alters the data collection technique to prepare for any subsequent data packets from the source.

In the creation and use of a data packet comprising self-describing data, the surgical hub includes identification features. The hub and intelligent devices use self-describing data packets to minimize data size and data handling. In a surgical hub that generates large volumes of data, the self-describing data packets minimize data size and data handling, thus saving time and enabling the operating theater to run more efficiently.

Figure 29:
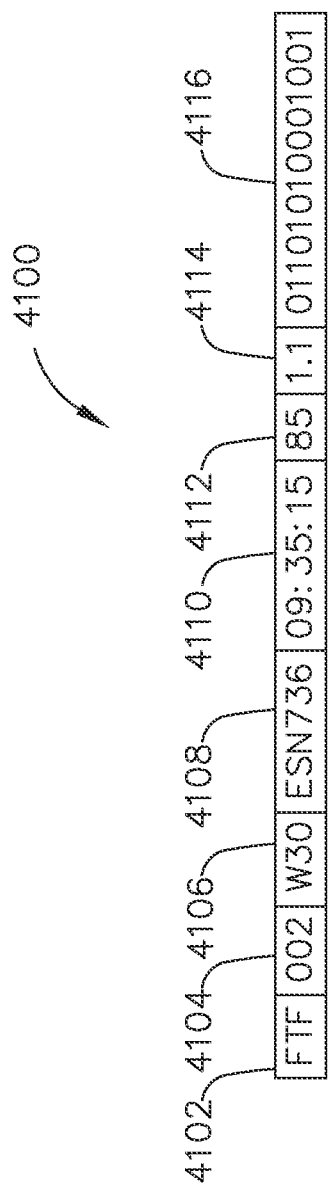
FIG. 29 illustrates a self-describing data packet comprising self-describing data, in accordance with at least one aspect of the present disclosure.

FIG. 29 illustrates a self-describing data packet 4100 comprising self-describing data, according to one aspect of the present disclosure. With reference also to FIGS. 1-11 to show interaction with an interactive surgical system 100 environment including a surgical hub 106, 206, in one aspect, self-describing data packets 4100 as shown in FIG. 29 are generated at an issuing instrument 235, or device or module located in or in communication with the operating theater, and include identifiers for all devices 235 that handle the packet along a communication path. The self description allows a processor 244 to interpret the data payload of the packet 4100 without having advance knowledge of the definition of the data payload prior to receiving the self-describing data packet 4100. The processor 244 can interpret the data payload by parsing an incoming self-describing packet 4100 as it is received and identifying the data payload without being notified in advance that the self-describing packet 4100 was received. The data is for every data point or data string. The data payload includes type of data, source of data, device IDs that generated the data, data units, time when data was generated, and an authentication that the self-describing data packet 4100 is unaltered. Once the processor 244, which may be located either in the device or the surgical hub 206, receives an unexpected self-describing data packet 4100 and verifies the source of the self-describing data packet 4100, the processor 244 alters the data collection means to be ready for any subsequent self-describing data packets 4100 from that source. In one example, the information contained in a self-describing packet 4100 may be recorded during the first firing 4172 in the lung tumor resection surgical procedure described in connection with FIGS. 31-35.

The self-describing data packet 4100 includes not only the data but a preamble which defines what the data is and where the data came from as well as an encryption certificate verifying the authenticity of each data packet 4100. As shown in FIG. 29, the data packet 4100 may comprise a self-describing data header 4102 (e.g., force-to-fire [FTF], force-to-close [FTC], energy amplitude, energy frequency, energy pulse width, speed of firing, and the like), a device ID 4104 (e.g., 002), a shaft ID 4106 (e.g., W30), a cartridge ID 4108 (e.g., ESN736), a unique time stamp 4110 (e.g., 09:35:15), a force-to-fire value 4112 (e.g., 85) when the self-describing data header 4102 includes FTF (force-to-fire), otherwise, this position in the data packet 4100 includes the value of force-to-close, energy amplitude, energy frequency, energy pulse width, speed of firing, and the like. The data packet 4100, further includes tissue thickness value 4114 (e.g., 1.1 mm), and an identification certificate of data value 4116 (e.g., 01101010001001) that is unique for each data packet 4100. Once the self-describing data packet 4100 is received by another instrument 235, surgical hub 206, cloud 204, etc., the receiver parses the self-describing data header 4102 and based on its value knows what data type is contained in the self-describing data packet 4100. TABLE 1 below lists the value of the self-describing data header 4102 and the corresponding data value.

TABLE 1

| Self-Describing Data Header (4102) | Data Type |
|---|---|
| FTF | Force To Fire (N) |
| FTC | Force To Close (N) |
| EA | Energy Amplitude (J) |
| EF | Energy Frequency (Hz) |
| EPW | Energy Pulse Width (Sec) |
| SOF | Speed Of Firing (mm/sec) |

Each self-describing data packet 4100 comprising self-describing data is initially assembled by the instrument 235, device, or module that generated the self-describing data packet 4100. Subsequently, the self-describing data packet 4100 comprising self-describing data is ordered and encrypted to generate an encryption certificate. The encryption certificate is unique for each self-describing data packet 4100. That data is then communicated via encrypted wired or wireless protocols and stored on the surgical hub 206 for processing and transmission to the cloud 204 analytics engine.

Each self-describing data packet 4100 comprising self-describing data includes a device ID 4104 to identify the specific instrument 235 that generated the self-describing data packet 4100, a time stamp 4110 to indicate the time that the data packet 4100 was generated, and when the self-describing data packet 4100 is received by the surgical hub 206. The surgical hub 206 ID also may be added to the self-describing data packet 4100.

Each of the self-describing data packets 4100 comprising self-describing data may include a packet wrapper that defines the beginning of the data packet 4100 and the end of the data packet 4100 including any identifiers necessary to forecast the number and order of the bits in the self-describing data packet.

The surgical hub 206 also manages redundant data sets. As the device 235 functions and interconnects with other surgical hubs 206, multiple sets of the same data may be created and stored on various devices 235. Accordingly, the surgical hub 206 manages multiple images of redundant data as well as anonymization and security of data. The surgical hub 206 also provides temporary visualization and communication, incident management, peer-to-peer processing or distributed processing, and storage backup and protection of data.

Figure 30:
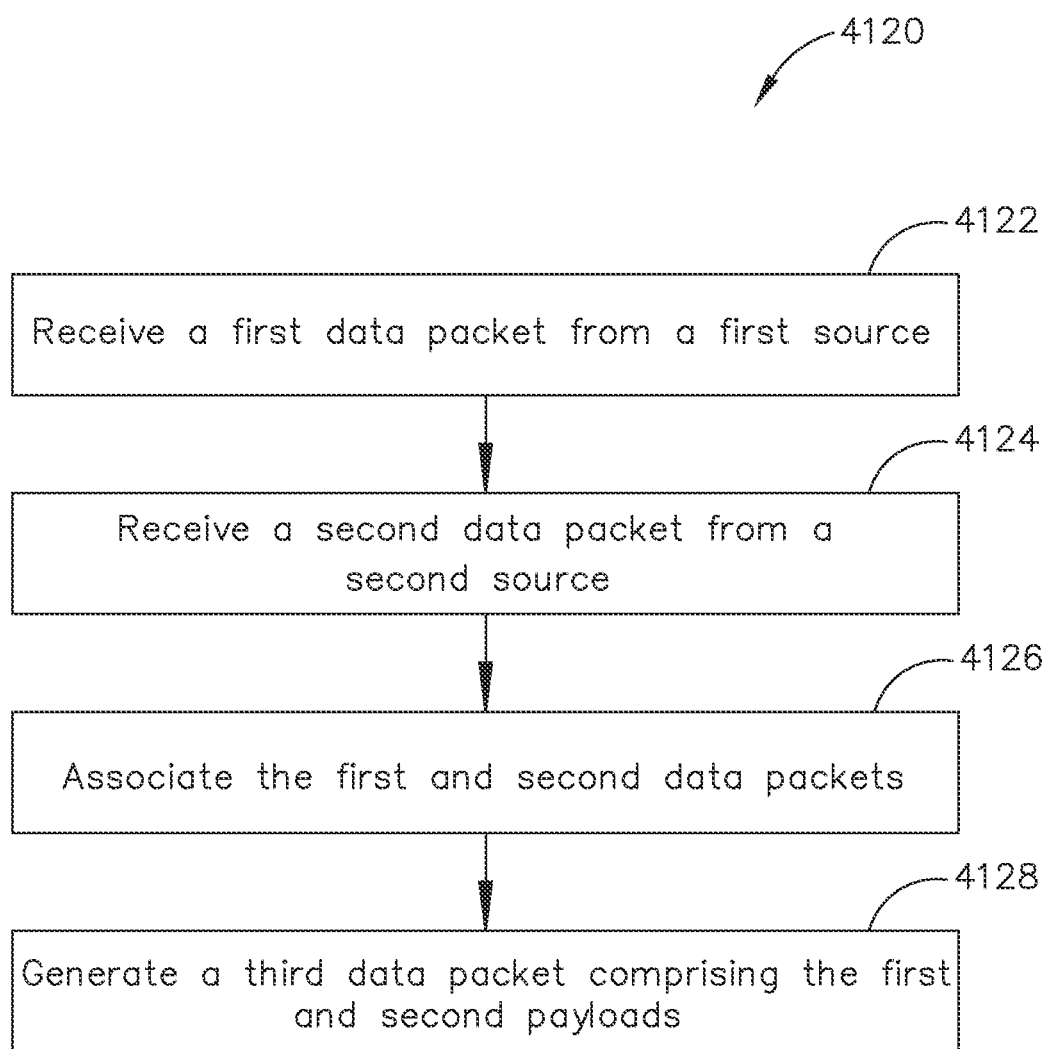
FIG. 30 is a logic flow diagram of a process depicting a control program or a logic configuration for using data packets comprising self-describing data, in accordance with at least one aspect of the present disclosure.

FIG. 30 is a logic flow diagram 4120 of a process depicting a control program or a logic configuration for using data packets comprising self-describing data, according to one aspect of the present disclosure. With reference to FIGS. 1-29, in one aspect, the present disclosure provides a surgical hub 206 comprising a processor 244 and a memory 249 coupled to the processor 244. The memory 249 storing instructions executable by the processor 244 to receive a first data packet from a first source, receive a second data packet from a second source, associate the first and second data packets, and generate a third data packet comprising the first and second data payloads. The first data packet comprises a first preamble, a first data payload, a source of the first data payload, and a first encryption certificate. The first preamble defines the first data payload and the first encryption certificate verifies the authenticity of the first data packet. The second data packet comprises a second preamble, a second data payload, a source of the second data payload, and a second encryption certificate. The second preamble defines the second data payload and the second encryption certificate verifies the authenticity of the second data packet.

In another aspect, the memory 249 stores instructions executable by the processor 244 to determine that a data payload is from a new source, verify the new source of the data payload, and alter a data collection process at the surgical hub to receive subsequent data packets from the new source.

In another aspect, the memory 249 stores instructions executable by the processor 244 to associate the first and second data packets based on a key. In another aspect, the memory 249 stores instructions executable by the processor 244 to anonymize the data payload of the third data packet. In another aspect, the memory 244 stores instructions executable by the processor 244 to receive an anonymized third data packet and reintegrate the anonymized third data packet into the first and second data packets using the key.

Figure 31:
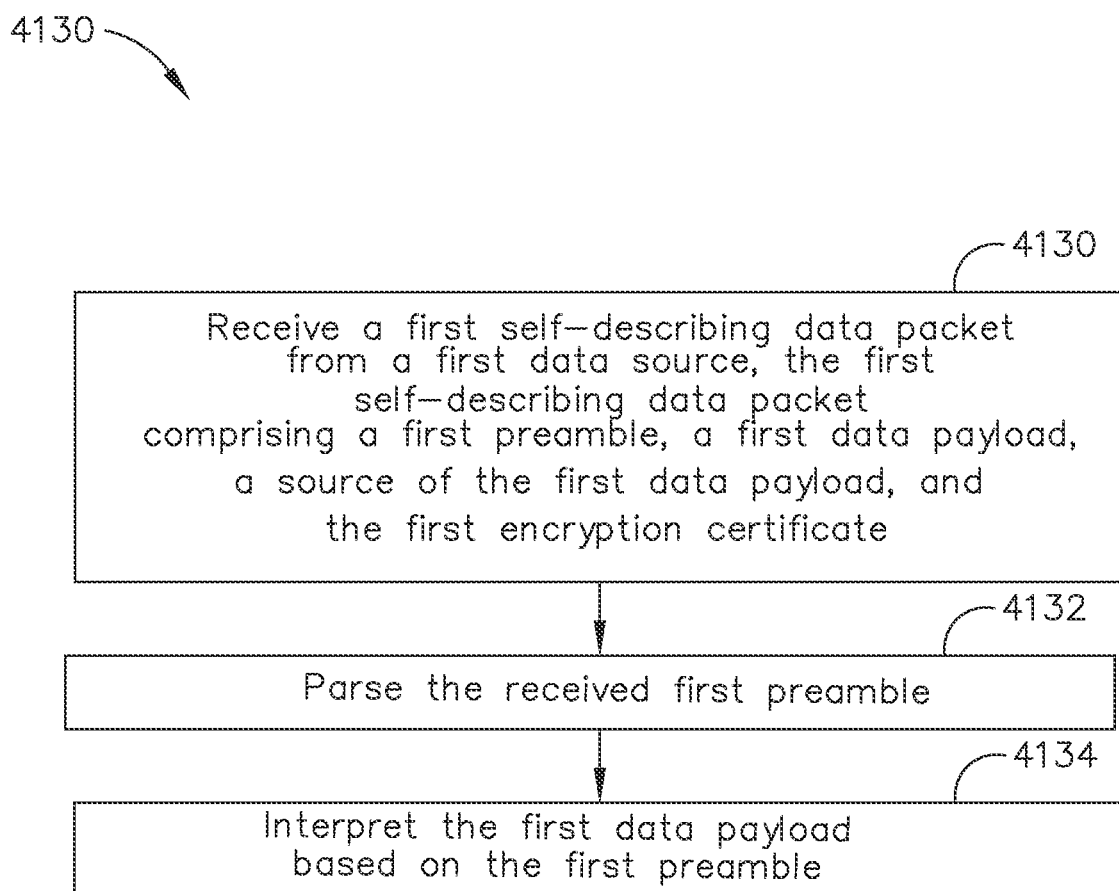
FIG. 31 is a logic flow diagram of a process depicting a control program or a logic configuration for using data packets comprising self-describing data, in accordance with at least one aspect of the present disclosure.

FIG. 31 is a logic flow diagram 4130 of a process depicting a control program or a logic configuration for using data packets comprising self-describing data, according to one aspect of the present disclosure. With reference to FIG. 31 and with reference also to FIGS. 1-11 to show interaction with an interactive surgical system 100 environment including a surgical hub 106, 206, in one aspect, the present disclosure provides a surgical hub 206 comprising a processor 244 and a memory 249 coupled to the processor 244. The memory 249 storing instructions executable by the processor 244 to receive 4132 a first self-describing data packet from a first data source, the first self-describing data packet comprising a first preamble, a first data payload, a source of the first data payload, and a first encryption certificate. The first preamble defines the first data payload and the first encryption certificate verifies the authenticity of the first data packet. The memory 249 storing instructions executable by the processor 244 to parse 4134 the received first preamble and interpret 4136 the first data payload based on the first preamble.

In various aspects, the memory 249 stores instructions executable by the processor 244 to receive a second self-describing data packet from a second data source, the second self-describing data packet comprising a second preamble, a second data payload, a source of the second data payload, and a second encryption certificate. The second preamble defines the second data payload and the second encryption certificate verifies the authenticity of the second data packet. The memory 249 storing instructions executable by the processor 244 to parse the received second preamble, interpret the second data payload based on the second preamble, associate the first and second self-describing data packets, and generate a third self-describing data packet comprising the first and second data payloads. In one aspect, the memory stores instructions executable by the processor to anonymize the data payload of the third self-describing data packet.

In various aspects, the memory stores instructions executable by the processor to determine that a data payload was generated by a new data source, verify the new data source of the data payload, and alter a data collection process at the surgical hub to receive subsequent data packets from the new data source. In one aspect, the memory stores instructions executable by the processor to associate the first and second self-describing data packets based on a key. In another aspect, the memory stores instructions executable by the processor to receive an anonymized third self-describing data packet and reintegrate the anonymized third self-describing data packet into the first and second self-describing data packets using the key.

Storage of the Data in a Manner of Paired Data Sets which can be Grouped by Surgery but not Necessarily Keyed to Actual Surgical Dates and Surgeons In one aspect, the present disclosure provides a data pairing method that allows a surgical hub to interconnect a device measured parameter with a surgical outcome. The data pair includes all the relevant surgical data or patient qualifiers without any patient identifier data. The data pair is generated at two separate and distinct times. The disclosure further provides configuring and storing the data in such a manner as to be able to rebuild a chronological series of events or merely a series of coupled but unconstrained data sets. The disclosure further provides storing data in an encrypted form and having predefined backup and mirroring to the cloud.

To determine the success or failure of a surgical procedure, data stored in a surgical instrument should be correlated with the outcome of the surgical procedure while simultaneously anonymizing the data to protect the privacy of the patient. One solution is to pair data associated with a surgical procedure, as recorded by the surgical instrument during the surgical procedure, with data assessing the efficacy of the procedure. The data is paired without identifiers associated with surgery, patient, or time to preserve anonymity. The paired data is generated at two separate and distinct times.

In one aspect, the present disclosure provides a surgical hub configured to communicate with a surgical instrument. The surgical hub comprises a processor and a memory coupled to the processor. The memory storing instructions executable by the processor to receive a first data set associated with a surgical procedure, receive a second data set associated with the efficacy of the surgical procedure, anonymize the first and second data sets by removing information that identifies a patient, a surgery, or a scheduled time of the surgery, and store the first and second anonymized data sets to generate a data pair grouped by surgery. The first data set is generated at a first time, the second data set is generated at a second time, and the second time is separate and distinct from the first time.

In another aspect, the memory stores instructions executable by the processor to reconstruct a series of chronological events based on the data pair. In another aspect, the memory stores instructions executable by the processor to reconstruct a series of coupled but unconstrained data sets based on the data pair. In another aspect, the memory stores instructions executable by the processor to encrypt the data pair, define a backup format for the data pair, and mirror the data pair to a cloud storage device.

In various aspects, the present disclosure provides a control circuit to receive and process data sets as described above. In various aspects, the present disclosure provides a non-transitory computer-readable medium storing computer readable instructions, which when executed, causes a machine to receive and process data sets as described above.

Storage of paired anonymous data enables the hospital or surgeon to use the data pairs locally to link to specific surgeries or to store the data pairs to analyze overall trends without extracting specific events in chronological manner.

In one aspect, the surgical hub provides user defined storage and configuration of data. Storage of the data may be made in a manner of paired data sets which can be grouped by surgery, but not necessarily keyed to actual surgical dates and surgeons. This technique provides data anonymity with regard to the patient and surgeon.

In one aspect, the present disclosure provides a data pairing method. The data pairing method comprises enabling a surgical hub to interconnect a device measured parameter with an outcome, wherein a data pair includes all the relevant tissue or patient qualifiers without any of the identifiers, wherein the data pair is generated at two distinct and separate times. In another aspect, the present disclosure provides a data configuration that includes whether the data is stored in such a manner as to enable rebuilding a chronological series of events or merely a series of coupled but unconstrained data sets. In another aspect, the data may be stored in an encrypted form. The stored data may comprise a predefined backup and mirroring to the cloud.

The data may be encrypted locally to the device. The data backup may be automatic to an integrated load secondary storage device. The device and/or the surgical hub may be configured to maintain the time of storage of the data and compile and transmit the data to another location for storage, e.g., another surgical hub or a cloud storage device. The data may be grouped together and keyed for transmission to the cloud analytics location. A cloud based analytics system is described in commonly owned U.S. Provisional Patent Application Ser. No. 62/611,340, filed Dec. 28, 2017, titled CLOUD-BASED MEDICAL ANALYTICS, which is incorporated herein by reference in its entirety.

In another aspect, the hub provides user selectable options for storing the data. In one technique, the hub enables the hospital or the surgeon to select if the data should be stored in such a manner that it could be used locally in a surgical hub to link to specific surgeries. In another technique, the surgical hub enables the data to be stored as data pairs so that overall trends can be analyzed without specific events extracted in a chronological manner.

Figure 32:
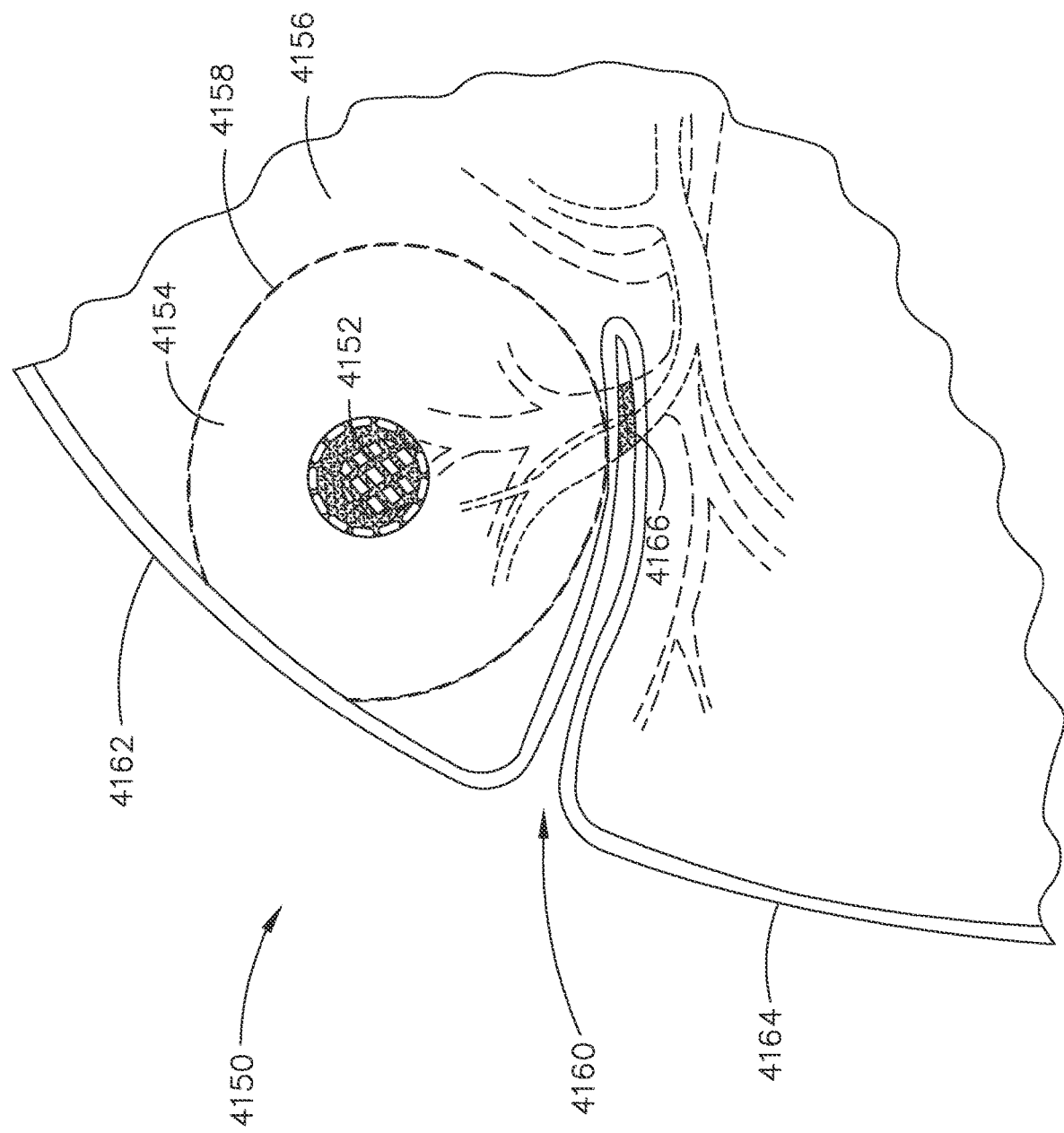
FIG. 32 is a diagram of a tumor embedded in the right superior posterior lobe of the right lung, in accordance with at least one aspect of the present disclosure.
Figure 38:
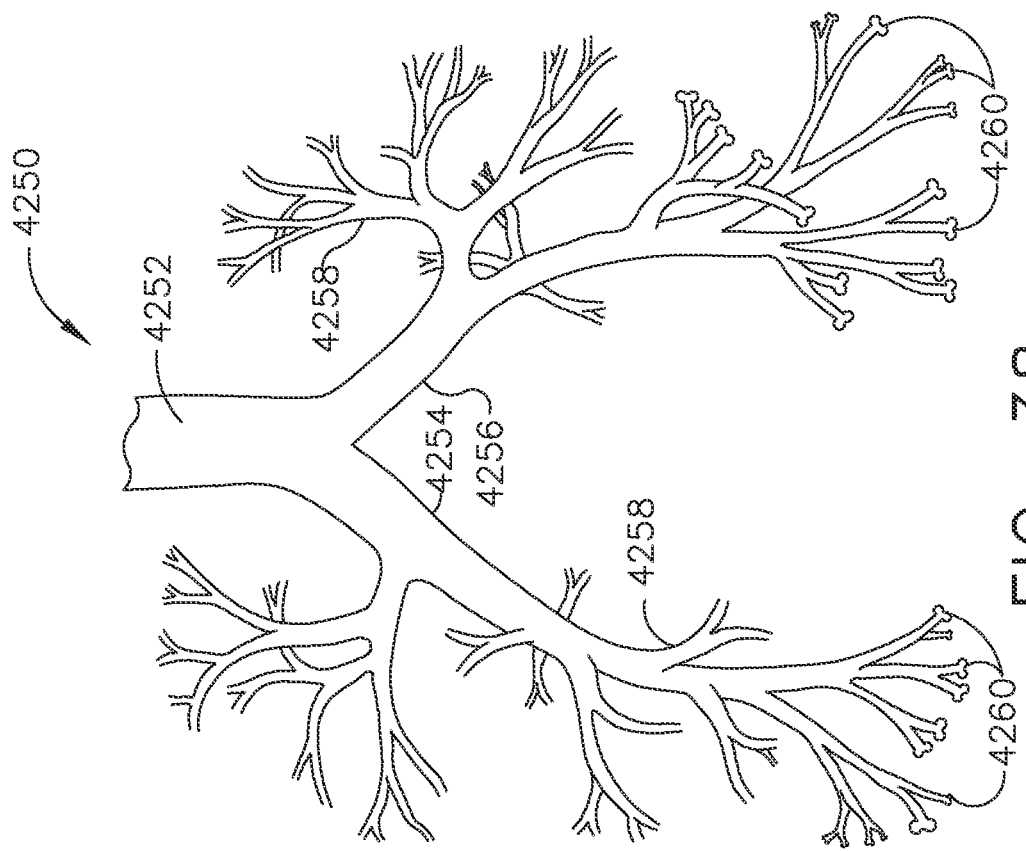
FIG. 38 is a diagram of the bronchial tree including the trachea and bronchi of the lung.
Figure 37:
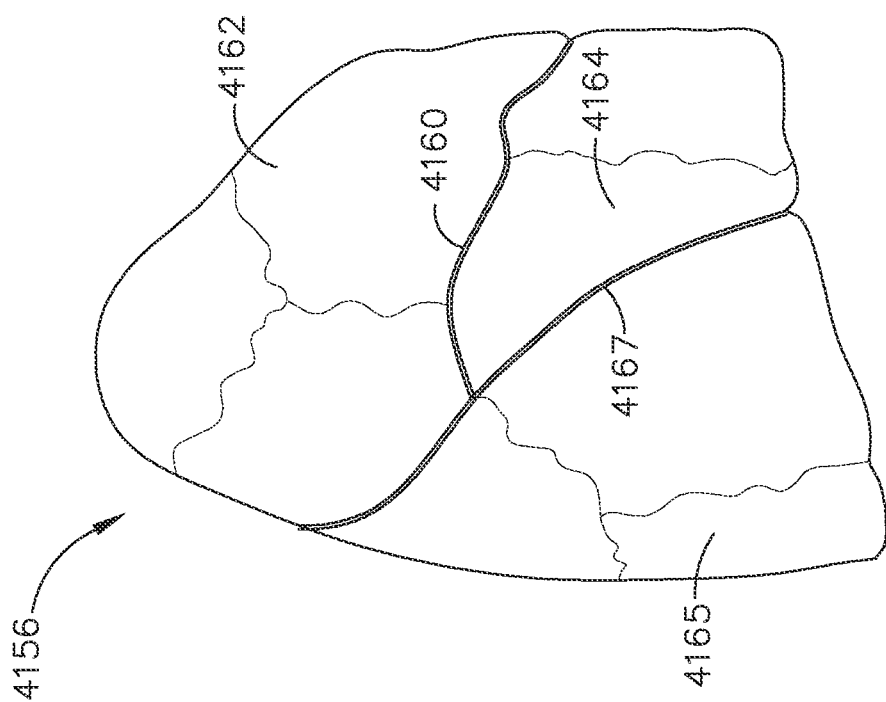
FIG. 37 is a diagram of the right lung.

FIG. 32 is a diagram 4150 of a tumor 4152 embedded in the right superior posterior lobe 4154 of the right lung 4156, according to one aspect of the present disclosure. To remove the tumor 4152, the surgeon cuts around the tumor 4152 along the perimeter generally designated as a margin 4158. A fissure 4160 separates the upper lobe 4162 and the middle lobe 4164 of the right lung 4156. In order to cut out the tumor 4152 about the margin 4158, the surgeon must cut the bronchial vessels 4166 leading to and from the middle lobe 4164 and the upper lobe 4162 of the right lung 4156. The bronchial vessels 4166 must be sealed and cut using a device such as a surgical stapler, electrosurgical instrument, ultrasonic instrument, a combo electrosurgical/ultrasonic instrument, and/or a combo stapler/electrosurgical device generally represented herein as the instrument/device 235 coupled to the surgical hub 206. The device 235 is configured to record data as described above, which is formed as a data packet, encrypted, stored, and/or transmitted to a remote data storage device 105 and processed by the server 113 in the cloud 104. FIGS. 37 and 38 are diagrams that illustrate the right lung 4156 and the bronchial tree 4250 embedded within the parenchyma tissue of the lung.

In one aspect, the data packet may be in the form of the self-describing data 4100 described in connection with FIGS. 29-31. The self-describing data packet 4100 will contain the information recorded by the device 235 during the procedure. Such information may include, for example, a self-describing data header 4102 (e.g., force-to-fire [FTF], force-to-close [FTC], energy amplitude, energy frequency, energy pulse width, speed of firing, and the like) based on the particular variable. The device ID 4104 (e.g., 002) of the instrument/device 235 used in the procedure including components of the instrument/device 235 such as the shaft ID 4106 (e.g., W30) and the cartridge ID 4108 (e.g., ESN736). The self-describing packet 4100 also records a unique time stamp 4110 (e.g., 09:35:15) and procedural variables such as a force-to-fire value 4112 (e.g., 85) when the self-describing data header 4102 includes FTF (force-to-fire), otherwise, this position in the data packet 4100 includes the value of force-to-close (FTC), energy amplitude, energy frequency, energy pulse width, speed of firing, and the like, as shown in TABLE 1, for example. The data packet 4100, further may include tissue thickness value 4114 (e.g., 1.1 mm), which in this example refers to the thickness of the bronchial vessel 4166 exposed in the fissure 4160 that were sealed and cut. Finally, each self-describing packet 4100 includes an identification certificate of data value 4116 (e.g., 01101010001001) that uniquely identifies each data packet 4100 transmitted by the device/instrument 235 to the surgical hub 206, further transmitted from the surgical hub 206 to the cloud 204 and stored on the storage device 205 coupled to the server 213, and/or further transmitted to the robot hub 222 and stored.

The data transmitted by way of a self-describing data packet 4100 is sampled by the instrument device 235 at a predetermined sample rate. Each sample is formed into a self-describing data packet 4100 which is transmitted to the surgical hub 206 and eventually is transmitted from the surgical hub 206 to the cloud 204. The samples may be stored locally in the instrument device 235 prior to packetizing or may be transmitted on the fly. The predetermined sampling rate and transmission rate are dictated by communication traffic in the surgical hub 206 and may be adjusted dynamically to accommodate current bandwidth limitations. Accordingly, in one aspect, the instrument device 235 may record all the samples taken during surgery and at the end of the procedure packetize each sample into a self-describing packet 4100 and transmit the self-describing packet 4100 to the surgical hub 206. In another aspect, the sampled data may be packetized as it is recorded and transmitted to the surgical hub 206 on the fly.

Figure 33:
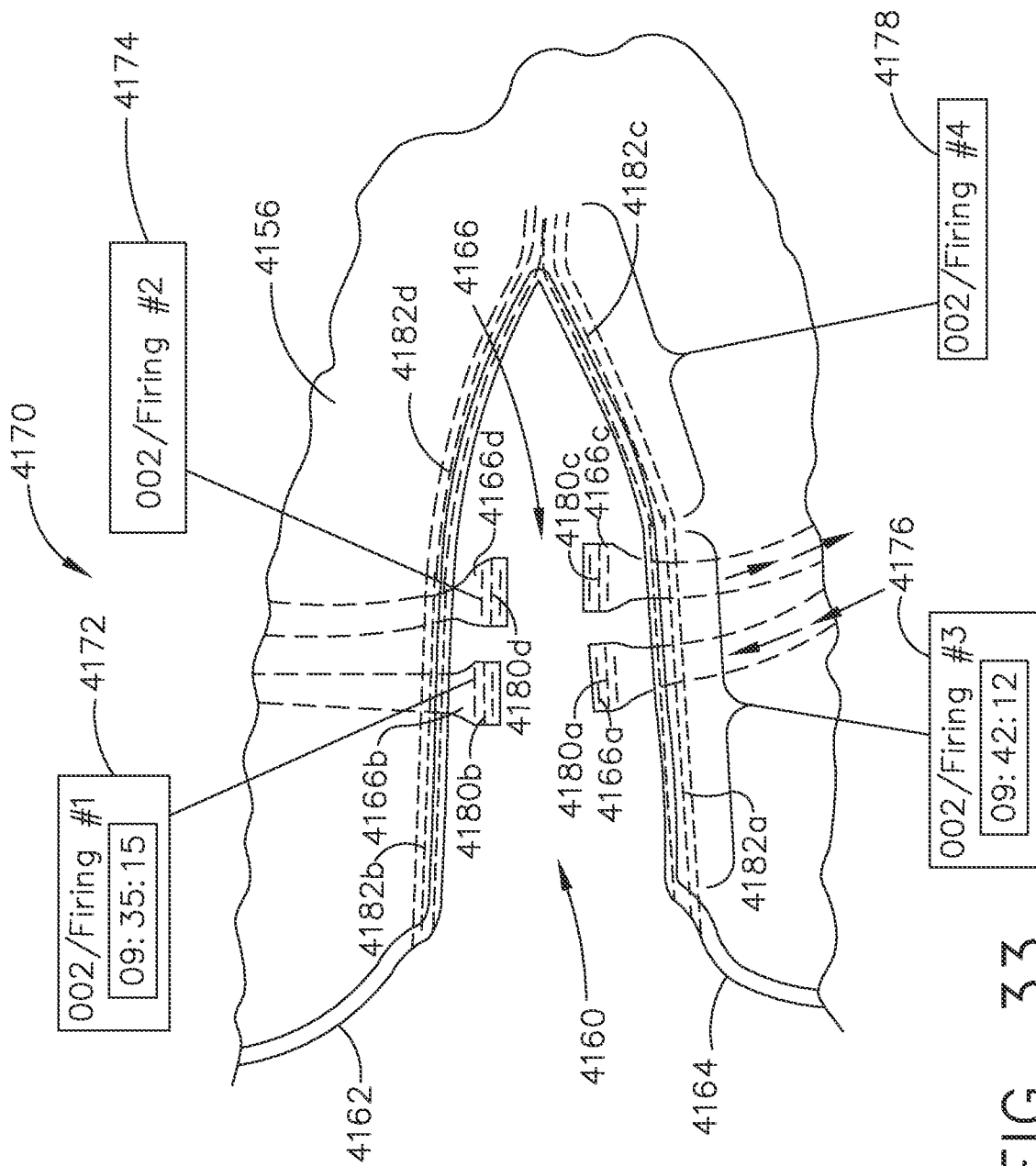
FIG. 33 is a diagram of a lung tumor resection surgical procedure including four separate firings of a surgical stapler to seal and cut bronchial vessels exposed in the fissure leading to and from the upper and lower lobes of the right lung shown in FIG. 32, in accordance with at least one aspect of the present disclosure.

FIG. 33 is a diagram 4170 of a lung tumor resection surgical procedure including four separate firings of a surgical stapler device 235 to seal and cut bronchial vessels 4166 exposed in the fissure 4160 leading to and from the upper and lower lobes 4162, 4164 of the right lung 4156 shown in FIG. 32, according to one aspect of the present disclosure. The surgical stapler device 235 is identified by a Device ID "002". The data from each firing of the surgical stapler device 235 is recorded and formed into a data packet 4100 comprising self-describing data as shown in FIG. 30. The self-describing data packet 4100 shown in FIG. 30 is representative of the first firing of device "002" having a staple cartridge serial number of ESN736, for example. In the following description, reference also is made to FIGS. 12-19 for descriptions of various architectures of instruments/devices 235 that include a processor or a control circuit coupled to a memory for recording (e.g., saving or storing) data collected during a surgical procedure.

Figure 34:
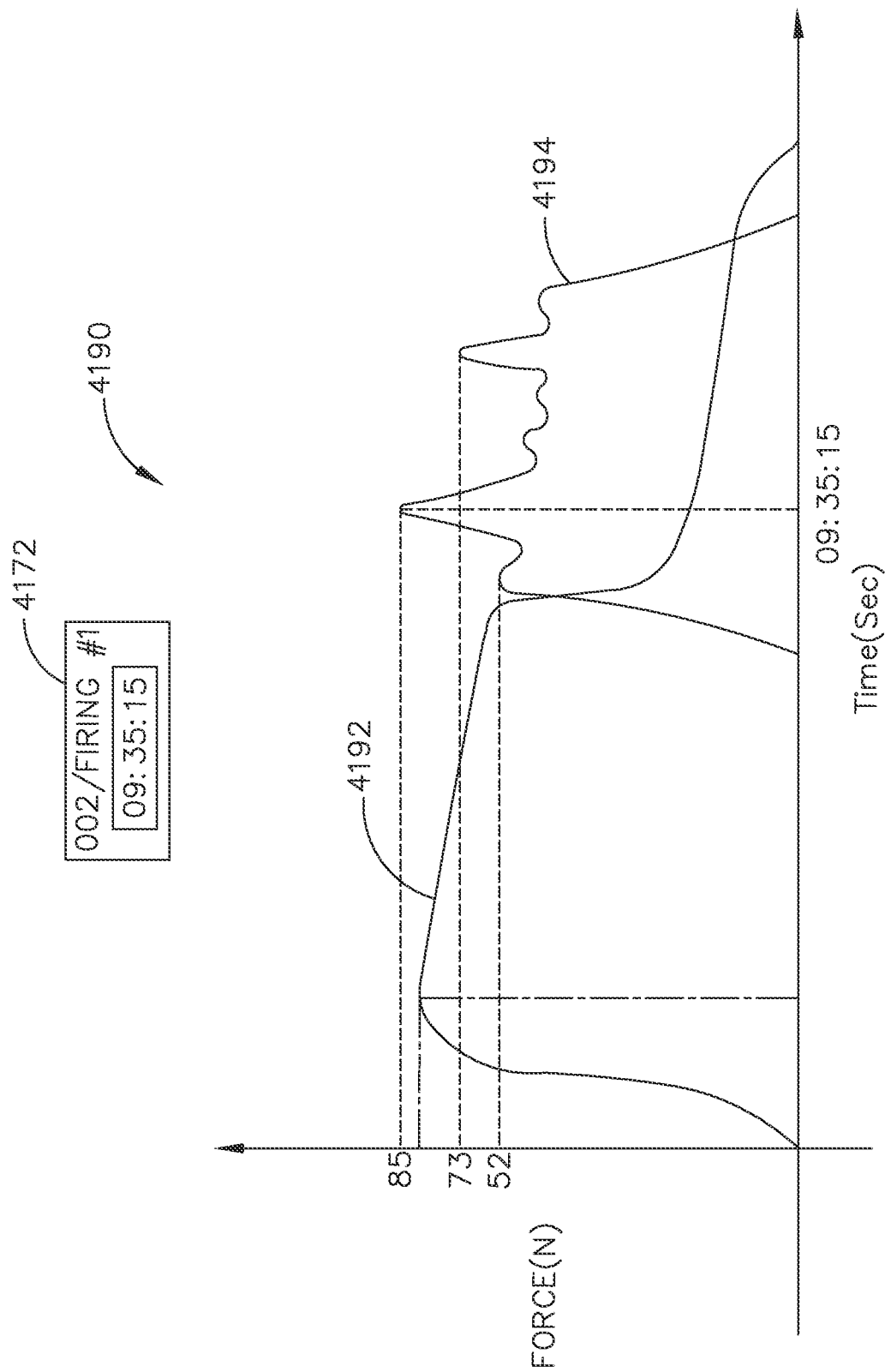
FIG. 34 is a graphical illustration of a force-to-close (FTC) versus time curve and a force-to-fire (FTF) versus time curve characterizing the first firing of device 002 as shown in FIG. 32, in accordance with at least one aspect of the present disclosure.

The first firing 4172 is recorded at anonymous time 09:35:15. The first firing 4172 seals and severs a first bronchial vessel 4166 leading to and from the middle lobe 4164 and the upper lobe 4162 of the right lung 4156 into a first portion 4166a and a second portion 4166b, where each portion 4166a, 4166b is sealed by respective first and second staple lines 4180a, 4180b. Information associated with the first firing 4172, for example the information described in connection with FIG. 30, is recorded in the surgical stapler device 235 memory and is used to build a first self-describing data packet 4100 described in connection with FIGS. 29-31. The first self-describing packet 4100 may be transmitted upon completion of the first firing 4172 or may be kept stored in the surgical stapler device 235 memory until the surgical procedure is completed. Once transmitted by the surgical stapler device 235, the first self-describing data packet 4100 is received by the surgical hub 206. The first self-describing data packet 4100 is anonymized by stripping and time stamping 4038 the data, as discussed, for example, in connection with FIG. 23. After the lung resection surgical is completed, the integrity of the seals of the first and second staple lines 4182a, 4182b will be evaluated as shown in FIG. 34, for example, and the results of the evaluation will be paired with information associated with the first firing 4172.

The second firing 4174 seals and severs a second bronchial vessel of the bronchial vessels 4166 leading to and from the middle lobe 4164 and the upper lobe 4162 of the right lung 4156 into a first portion 4166c and a second portion 4166d, where each portion 4166c, 4166d is sealed by first and second staple lines 4180c, 4180d. Information associated with the second firing 4174, for example the information described in connection with FIGS. 29-31, is recorded in the surgical stapler device 235 memory and is used to build a second self-describing data packet 4100 described in connection with FIGS. 29-31. The second self-describing data packet 4100 may be transmitted upon completion of the second firing 4174 or may be kept stored in the surgical stapler device 235 memory until the surgical procedure is completed. Once transmitted by the surgical stapler device 235, the second self-describing data packet 4100 is received by the surgical hub 206. The second self-describing data packet 4100 is anonymized by stripping and time stamping 4038 the data as discussed, for example, in connection with FIG. 23. After the lung resection surgical is completed, the integrity of the seals of the first and second staple lines 4182c, 4182d will be evaluated as shown in FIG. 34, for example, and the results of the evaluation will be paired with information associated with the second firing 4174.

The third firing 4176 is recorded at anonymous time 09:42:12. The third firing 4176 seals and severs an outer portion of the upper and middle lobes 4162, 4164 of the right lung 4156. First and second staple lines 4182a, 4182b are used to seal the outer portion of the upper and middle lobes 4162, 4162. Information associated with the third firing 4176, for example the information described in connection with FIGS. 29-31, is recorded in the surgical stapler device 235 memory and is used to build a third self-describing data packet 4100 described in connection with FIGS. 29-31. The third self-describing packet 4100 may be transmitted upon completion of the third firing 4176 or may be kept stored in the surgical stapler device 235 memory until the surgical procedure is completed. Once transmitted by the surgical stapler device 235, the third self-describing data packet 4100 is received by the surgical hub 206. The third self-describing data packet 4100 is anonymized by stripping and time stamping 4038 the data, as discussed, for example, in connection with FIG. 23. After the lung resection surgical is completed, the integrity of the seals of the first and second staple lines 4180a, 4180b will be evaluated as shown in FIG. 34, for example, and the results of the evaluation will be paired with information associated with the third firing 4172.

The fourth firing 4178 seals and severs an inner portion of the upper and middle lobes 4162, 4162 of the right lung 4156. First and second staple lines 4182c, 4182d are used to seal the inner portions of the upper and middle lobes 4162, 4164. Information associated with the fourth firing 4178, for example the information described in connection with FIG. 30, is recorded in the surgical stapler device 235 memory and is used to build a fourth self-describing data packet 4100 described in connection with FIGS. 29-31. The fourth self-describing packet 4100 may be transmitted upon completion of the fourth firing 4178 or may be kept stored in the surgical stapler device 235 memory until the surgical procedure is completed. Once transmitted by the surgical stapler device 235, the fourth self-describing data packet 4100 is received by the surgical hub 206. The fourth self-describing data packet 4100 is anonymized by stripping and time stamping 4038 the data, as discussed, for example, in connection with FIG. 23. After the lung resection surgical is completed, the integrity of the seals of the first and second staple lines 4182a, 4182b will be evaluated as shown in FIG. 34, for example, and the results of the evaluation will be paired with information associated with the fourth firing 4172.

FIG. 34 is a graphical illustration 4190 of a force-to-close (FTC) versus time curve 4192 and a force-to-fire (FTF) versus time curve 4194 characterizing the first firing 4172 of device 002 shown in FIG. 33, according to one aspect of the present disclosure. The surgical stapler device 235 is identified as 002 with a 30 mm staple cartridge S/N ESN736 with a PVS shaft S/N M3615N (Shaft ID W30). The surgical stapler device 235 was used for the first firing 4172 to complete the lung resection surgical procedure shown in FIG. 33. As shown in FIG. 34, the peak force-to-fire force of 85 N. is recorded at anonymous time 09:35:15. Algorithms in the surgical stapler device 235 determine a tissue thickness of about 1.1 mm. As described hereinbelow, the FTC versus time curve 4192 and the FTF versus time curve 4194 characterizing the first firing 4172 of the surgical device 235 identified by ID 002 will be paired with the outcome of the lung resection surgical procedure, transmitted to the surgical hub 206, anonymized, and either stored in the surgical hub 206 or transmitted to the cloud 204 for aggregation, further processing, analysis, etc.

Figure 35:
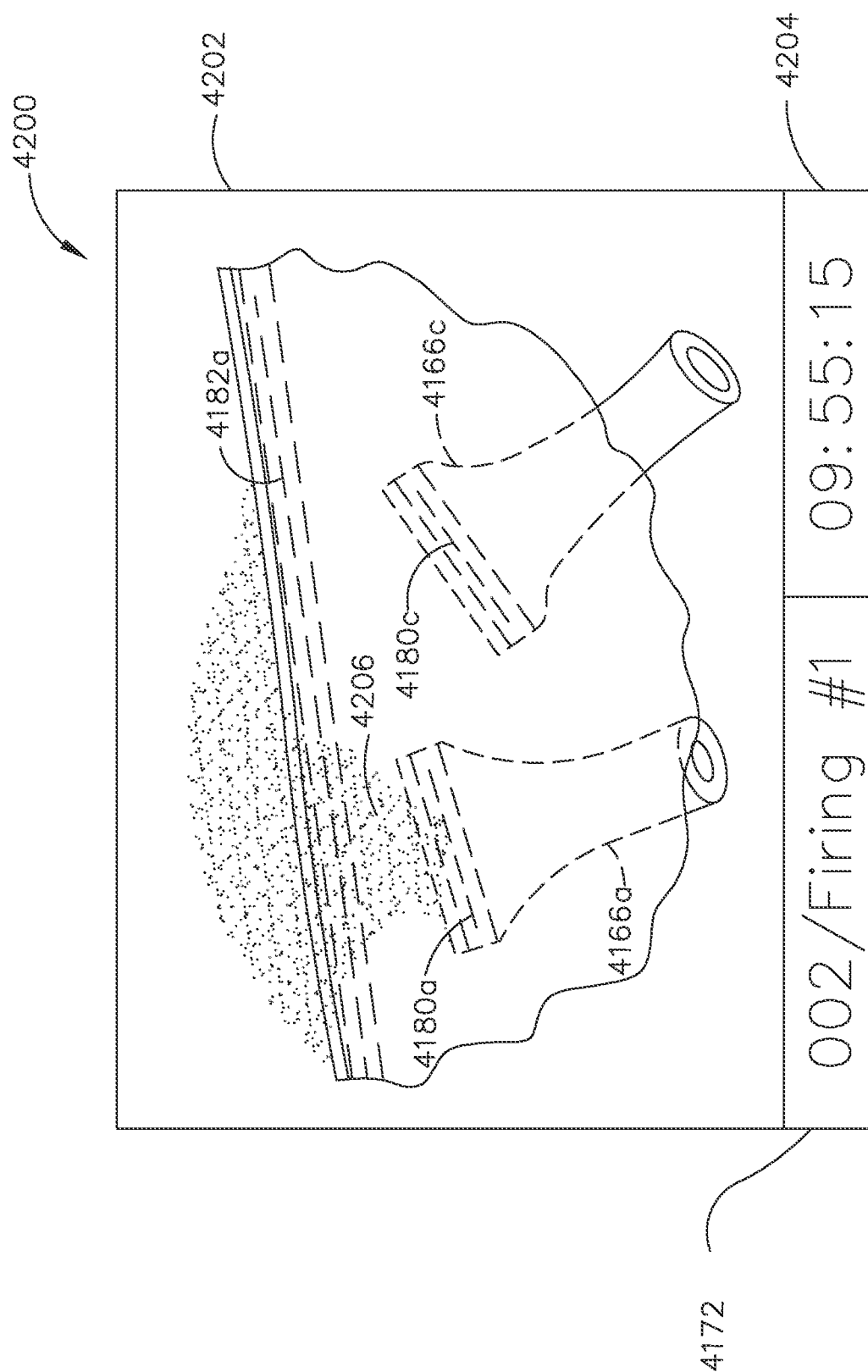
FIG. 35 is a diagram of a staple line visualization laser Doppler to evaluate the integrity of staple line seals by monitoring bleeding of a vessel after a firing of a surgical stapler, in accordance with at least one aspect of the present disclosure.

FIG. 35 is a diagram 4200 illustrating a staple line visualization laser Doppler to evaluate the integrity of staple line seals by monitoring bleeding of a vessel after a firing of a surgical stapler, according to one aspect of the present disclosure. A laser Doppler technique is described in above under the heading "Advanced Imaging Acquisition Module," in U.S. Provisional Patent Application Ser. No. 62/611,341, filed Dec. 28, 2017, and titled INTERACTIVE SURGICAL PLATFORM, which is hereby incorporated by reference herein in its entirety. The laser Doppler provides an image 4202 suitable for inspecting seals along the staple lines 4180a, 4180b, 4182a and for visualizing bleeding 4206 of any defective seals. Laser Doppler inspection of the first firing 4172 of device 002 shows a defective seal at the first staple line 4180a of the first portion 4166a of the bronchial vessel sealed during the first firing 4172. The staple line 4180a seal is bleeding 4206 out at a volume of 0.5 cc. The image 4202 is recorded at anonymous time 09:55:15 4204 and is paired with the force-to-close curve 4192 and force-to-fire curve 4194 shown in FIG. 34. The data pair set is grouped by surgery and is stored locally in the surgical hub 206 storage 248 and/or remotely to the cloud 204 storage 205 for aggregation, processing, and analysis, for example. For example, the cloud 204 analytics engine associates the information contained in the first self-describing packet 4100 associated with the first firing 4172 and indicate that a defective seal was produced at the staple line 4166a. Over time, this information can be aggregated, analyzed, and used to improve outcomes of the surgical procedure, such as, resection of a lung tumor, for example.

Figure 36:
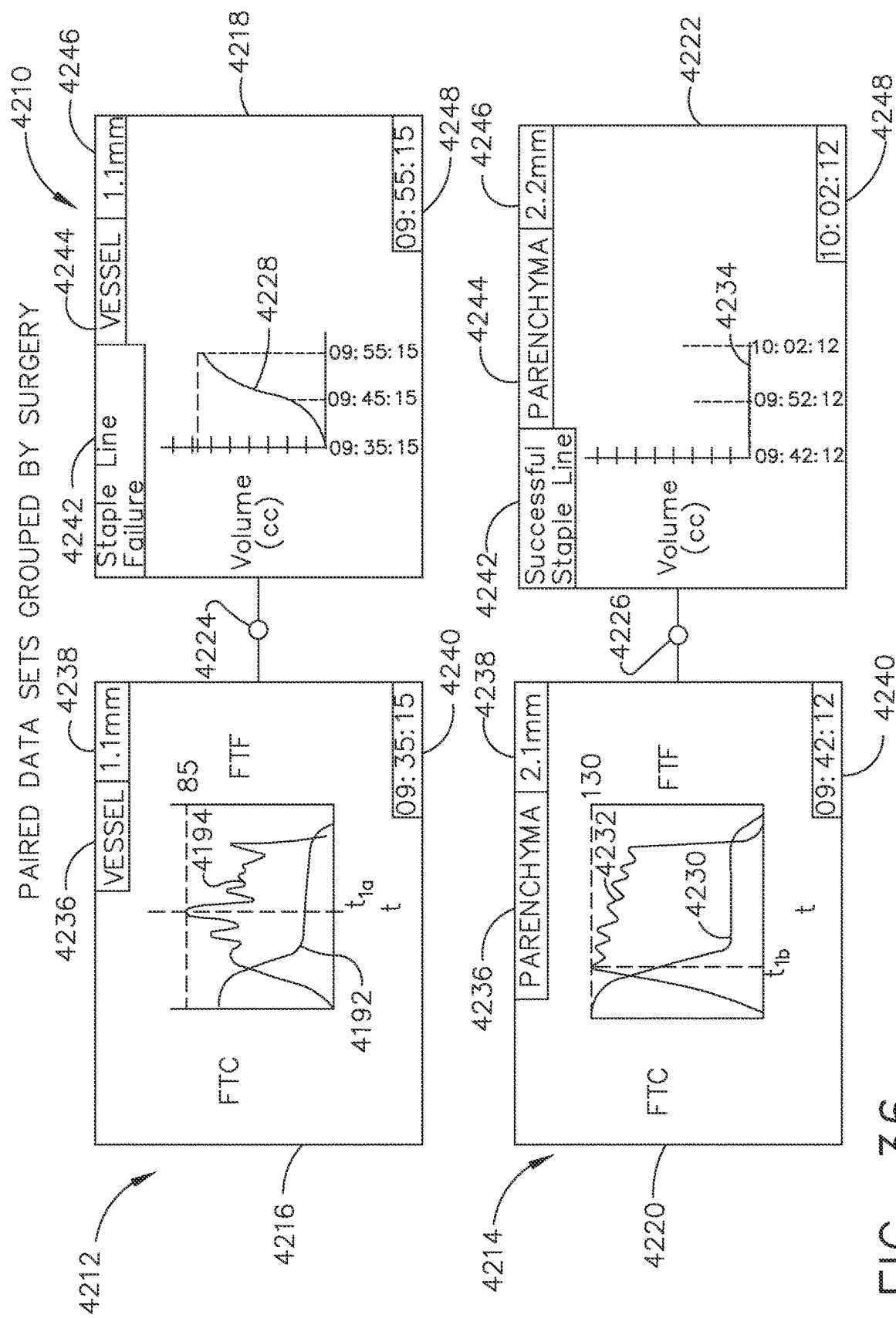
FIG. 36 illustrates a paired data set grouped by surgery, in accordance with at least one aspect of the present disclosure.

FIG. 36 illustrates two paired data sets 4210 grouped by surgery, according to one aspect of the present disclosure. The upper paired data set 4212 is grouped by one surgery and a lower paired data set 4214 grouped by another surgery. The upper paired data set 4212, for example, is grouped by the lung tumor resection surgery discussed in connection with FIGS. 33-36. Accordingly, the rest of the description of FIG. 36 will reference information described in FIGS. 32-35 as well as FIGS. 1-21 to show interaction with an interactive surgical system 100 environment including a surgical hub 106, 206. The lower paired data set 4214 is grouped by a liver tumor resection surgical procedure where the surgeon treated parenchyma tissue. The upper paired data set is associated with a failed staple line seal and the bottom paired data set is associated with a successful staple line seal. The upper and lower paired data sets 4212, 4214 are sampled by the instrument device 235 and each sample formed into a self-describing data packet 4100 which is transmitted to the surgical hub 206 and eventually is transmitted from the surgical hub 206 to the cloud 204. The samples may be stored locally in the instrument device 235 prior to packetizing or may be transmitted on the fly. Sampling rate and transmission rate are dictated by communication traffic in the surgical hub 206 and may be adjusted dynamically to accommodate current bandwidth limitations.

The upper paired data set 4212 includes a left data set 4216 recorded by the instrument/device 235 during the first firing 4172 linked 4224 to a right data set 4218 recorded at the time the staple line seal 4180a of the first bronchial vessel 4166a was evaluated. The left data set 4216 indicates a "Vessel" tissue type 4236 having a thickness 4238 of 1.1 mm. Also included in the left data set 4216 is the force-to-close curve 4192 and force-to-fire curve 4194 versus time (anonymous real time) recorded during the first firing 4172 of the lung tumor resection surgical procedure. The left data set 4216 shows that the force-to-fire peaked at 85 Lbs. and recorded at anonymous real time 4240 $t_{1a}$ (09:35:15). The right data set 4218 depicts the staple line visualization curve 4228 depicting leakage versus time. The right data set 4218 indicates that a "Vessel" tissue type 4244 having a thickness 4246 of 1.1 mm experienced a staple line 4180a seal failure 4242. The staple line visualization curve 4228 depicts leakage volume (cc) versus time of the staple line 4180a seal. The staple line visualization curve 4228 shows that the leakage volume reached 0.5 cc, indicating a failed staple line 4180a seal of the bronchial vessel 4166a, recorded at anonymous time 4248 (09:55:15).

The lower paired data set 4214 includes a left data set 4220 recorded by the instrument/device 235 during a firing linked 4226 to a right data set 4222 recorded at the time the staple line seal of the parenchyma tissue was evaluated. The left data set 4220 indicates a "Parenchyma" tissue type 4236 having a thickness 4238 of 2.1 mm. Also included in the left data set 4220 is the force-to-close curve 4230 and force-to-fire curve 4232 versus time (anonymous real time) recorded during the first firing of the liver tumor resection surgical procedure. The left data set 4220 shows that the force-to-fire peaked at 100 Lbs. and recorded at anonymous real time 4240 $t_{1b}$ (09:42:12). The right data set 4222 depicts the staple line visualization curve 4228 depicting leakage versus time. The right data set 4234 indicates that a "Parenchyma" tissue type 4244 having a thickness 4246 of 2.2 mm experienced a successful staple line seal. The staple line visualization curve 4234 depicts leakage volume (cc) versus time of the staple line seal. The staple line visualization curve 4234 shows that the leakage volume was 0.0 cc, indicating a successful staple line seal of the parenchyma tissue, recorded at anonymous time 4248 (10:02:12).

The paired date sets 4212, 4214 grouped by surgery are collected for many procedures and the data contained in the paired date sets 4212, 4214 is recorded and stored in the cloud 204 storage 205 anonymously to protect patient privacy, as described in connection with FIGS. 22-29. In one aspect, the paired date sets 4212, 4214 data are transmitted from the instrument/device 235, or other modules coupled to the surgical hub 206, to the surgical hub 206 and to the cloud 204 in the form of the self-describing packet 4100 as described in connection with FIGS. 31 and 32 and surgical procedure examples described in connection with FIGS. 32-36. The paired date sets 4212, 4214 data stored in the cloud 204 storage 205 is analyzed in the cloud 204 to provide feedback to the instrument/device 235, or other modules coupled to the surgical hub 206, notifying a surgical robot coupled to the robot hub 222, or the surgeon, that the conditions identified by the left data set ultimately lead to either a successful or failed seal. As described in connection with FIG. 36, the upper left data set 4216 led to a failed seal and the bottom left data set 4220 led to a successful seal. This is advantageous because the information provided in a paired data set grouped by surgery can be used to improve resection, transection, and creation of anastomosis in a variety of tissue types. The information can be used to avoid pitfalls that may lead to a failed seal.

FIG. 37 is a diagram of the right lung 4156 and FIG. 38 is a diagram of the bronchial tree 4250 including the trachea 4252 and the bronchi 4254, 4256 of the lungs. As shown in FIG. 37, the right lung 4156 is composed of three lobes divided into the upper lobe 4162, the middle lobe 4160, and the lower lobe 4165 separated by the oblique fissure 4167 and horizontal fissure 4160. The left lung is composed of only two smaller lobes due to the position of heart. As shown in FIG. 38, inside each lung, the right bronchus 4254 and the left bronchus 4256 divide into many smaller airways called bronchioles 4258, greatly increasing surface area. Each bronchiole 4258 terminates with a cluster of air sacs called alveoli 4260, where gas exchange with the bloodstream occurs.

Figure 39:
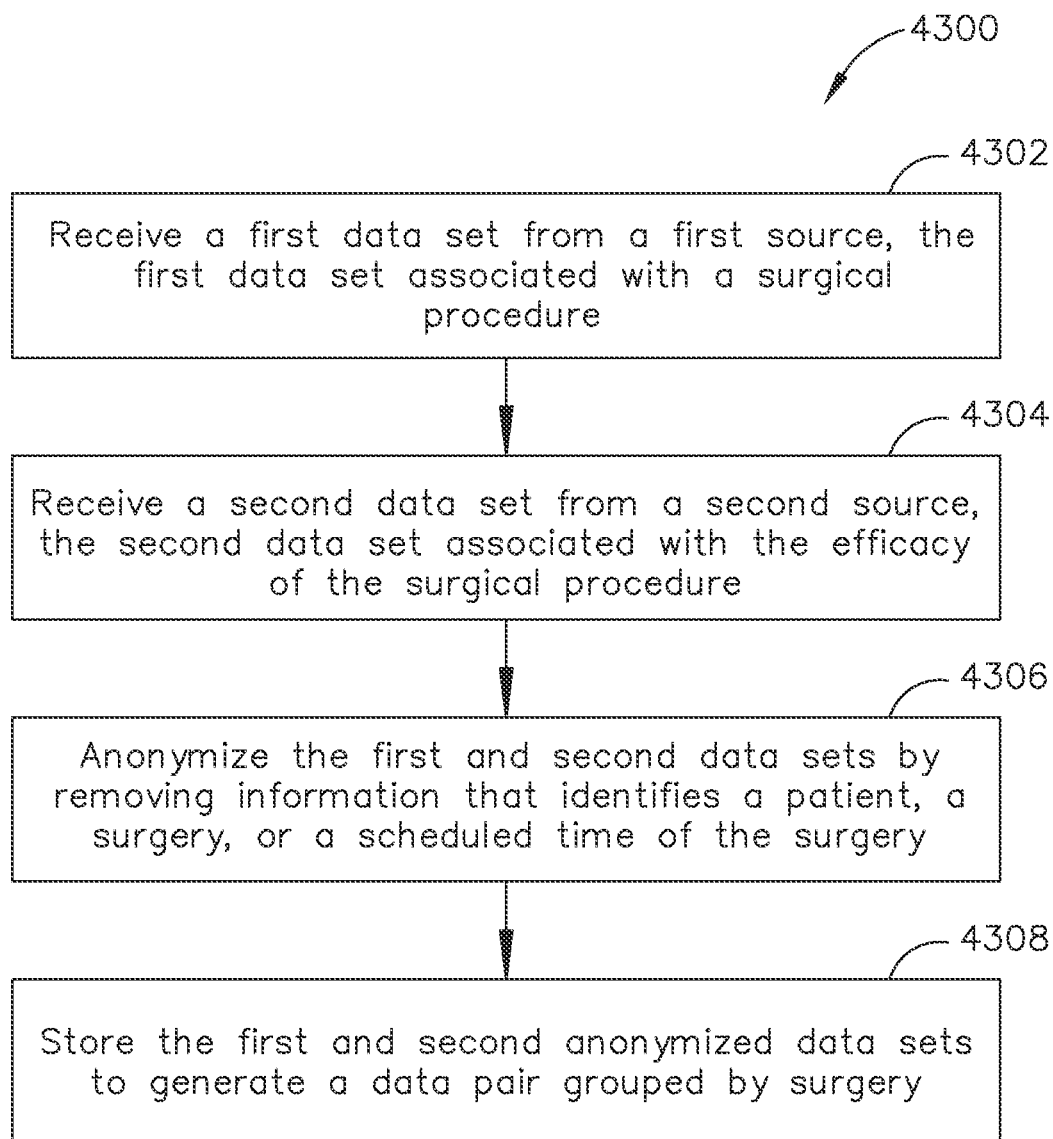
FIG. 39 is a logic flow diagram of a process depicting a control program or a logic configuration for storing paired anonymous data sets grouped by surgery, in accordance with at least one aspect of the present disclosure.

FIG. 39 is a logic flow diagram 4300 of a process depicting a control program or a logic configuration for storing paired anonymous data sets grouped by surgery, according to one aspect of the present disclosure. With reference to FIGS. 1-39, in one aspect, the present disclosure provides a surgical hub 206 configured to communicate with a surgical instrument 235. The surgical hub 206 comprises a processor 244 and a memory 249 coupled to the processor 244. The memory 249 storing instructions executable by the processor 244 to receive 4302 a first data set from a first source, the first data set associated with a surgical procedure, receive 4304 a second data set from a second source, the second data set associated with the efficacy of the surgical procedure, anonymize 4306 the first and second data sets by removing information that identifies a patient, a surgery, or a scheduled time of the surgery, and store 4308 the first and second anonymized data sets to generate a data pair grouped by surgery. The first data set is generated at a first time, the second data set is generated at a second time, and the second time is separate and distinct from the first time.

In another aspect, the memory 249 stores instructions executable by the processor 244 to reconstruct a series of chronological events based on the data pair. In another aspect, the memory 249 stores instructions executable by the processor 244 to reconstruct a series of coupled but unconstrained data sets based on the data pair. In another aspect, the memory 249 stores instructions executable by the processor 244 to encrypt the data pair, define a backup format for the data pair, and mirror the data pair to a cloud 204 storage device 205.

Determination of Data to Transmit to Cloud Based Medical Analytics

In one aspect, the present disclosure provides a communication hub and storage device for storing parameters and status of a surgical device what has the ability to determine when, how often, transmission rate, and type of data to be shared with a cloud based analytics system. The disclosure further provides techniques to determine where the analytics system communicates new operational parameters for the hub and surgical devices.

In a surgical hub environment, large amounts of data can be generated rather quickly and may cause storage and communication bottlenecks in the surgical hub network. One solution may include local determination of when and what data is transmitted for to the cloud-based medical analytics system for further processing and manipulation of surgical hub data. The timing and rate at which the surgical hub data is exported can be determined based on available local data storage capacity. User defined inclusion or exclusion of specific users, patients, or procedures enable data sets to be included for analysis or automatically deleted. The time of uploads or communications to the cloud-based medical analytics system may be determined based on detected surgical hub network down time or available capacity.

With reference to FIGS. 1-39, in one aspect, the present disclosure provides a surgical hub 206 comprising a storage device 248, a processor 244 coupled to the storage device 248, and a memory 249 coupled to the processor 244. The memory 249 stores instructions executable by the processor 244 to receive data from a surgical instrument 235, determine a rate at which to transfer the data to a remote cloud-based medical analytics network 204 based on available storage capacity of the storage device 248, determine a frequency at which to transfer the data to the remote cloud-based medical analytics network 204 based on the available storage capacity of the storage device 248 or detected surgical hub network 206 down time, and determine a type of data to transfer the data to a remote cloud-based medical analytics network 204 based on inclusion or exclusion of data associated with a users, patient, or surgical procedure.

In another aspect, the memory 249 stores instructions executable by the processor 244 to receive new operational parameters for the surgical hub 206 or the surgical instrument 235.

In various aspects, the present disclosure provides a control circuit to determine, rate, frequency and type of data to transfer the data to the remote cloud-based medical analytics network as described above. In various aspects, the present disclosure provides a non-transitory computer-readable medium storing computer readable instructions which, when executed, causes a machine to determine, rate, frequency and type of data to transfer to the remote cloud-based medical analytics network.

In one aspect, the surgical hub 206 is configured to determine what data to transmit to the cloud based analytics system 204. For example, a surgical hub 206 modular device 235 that includes local processing capabilities may determine the rate, frequency, and type of data to be transmitted to the cloud based analytics system 204 for analysis and processing.

In one aspect, the surgical hub 206 comprises a modular communication hub 203 and storage device 248 for storing parameters and status of a device 235 that has the ability to determine when and how often data can be shared with a cloud based analytics system 204, the transmission rate and the type of data that can be shared with the cloud based analytics system 204. In another aspect, the cloud analytics system 204 communicates new operational parameters for the surgical hub 206 and surgical devices 235 coupled to the surgical hub 206. A cloud based analytics system 204 is described in commonly owned U.S. Provisional Patent Application Ser. No. 62/611,340, filed Dec. 28, 2017, and titled CLOUD-BASED MEDICAL ANALYTICS, which is incorporated herein by reference in its entirety.

In one aspect, a device 235 coupled to a local surgical hub 206 determines when and what data is transmitted to the cloud analytics system 204 for company analytic improvements. In one example, the available local data storage capacity remaining in the storage device 248 controls the timing and rate at which the data is exported. In another example, user defined inclusion or exclusion of specific users, patients, or procedures allows data sets to be included for analysis or automatically deleted. In yet another example, detected network down time or available capacity determines the time of uploads or communications.

In another aspect, transmission of data for diagnosis of failure modes is keyed by specific incidents. For example, user defined failure of a device, instrument, or tool within a procedure initiates archiving and transmission of data recorded with respect to that instrument for failure modes analysis. Further, when a failure event is identified, all the data surrounding the event is archived and packaged for sending back for predictive informatics (PI) analytics. Data that is part of a PI failure is flagged for storage and maintenance until either the hospital or the cloud based analytics system releases the hold on the data.

Catastrophic failures of instruments may initiate an automatic archive and submission of data for implications analysis. Detection of a counterfeit component or adapter on an original equipment manufacturer (OEM) device initiates documentation of the component and recording of the results and outcome of its use.

Figure 40:
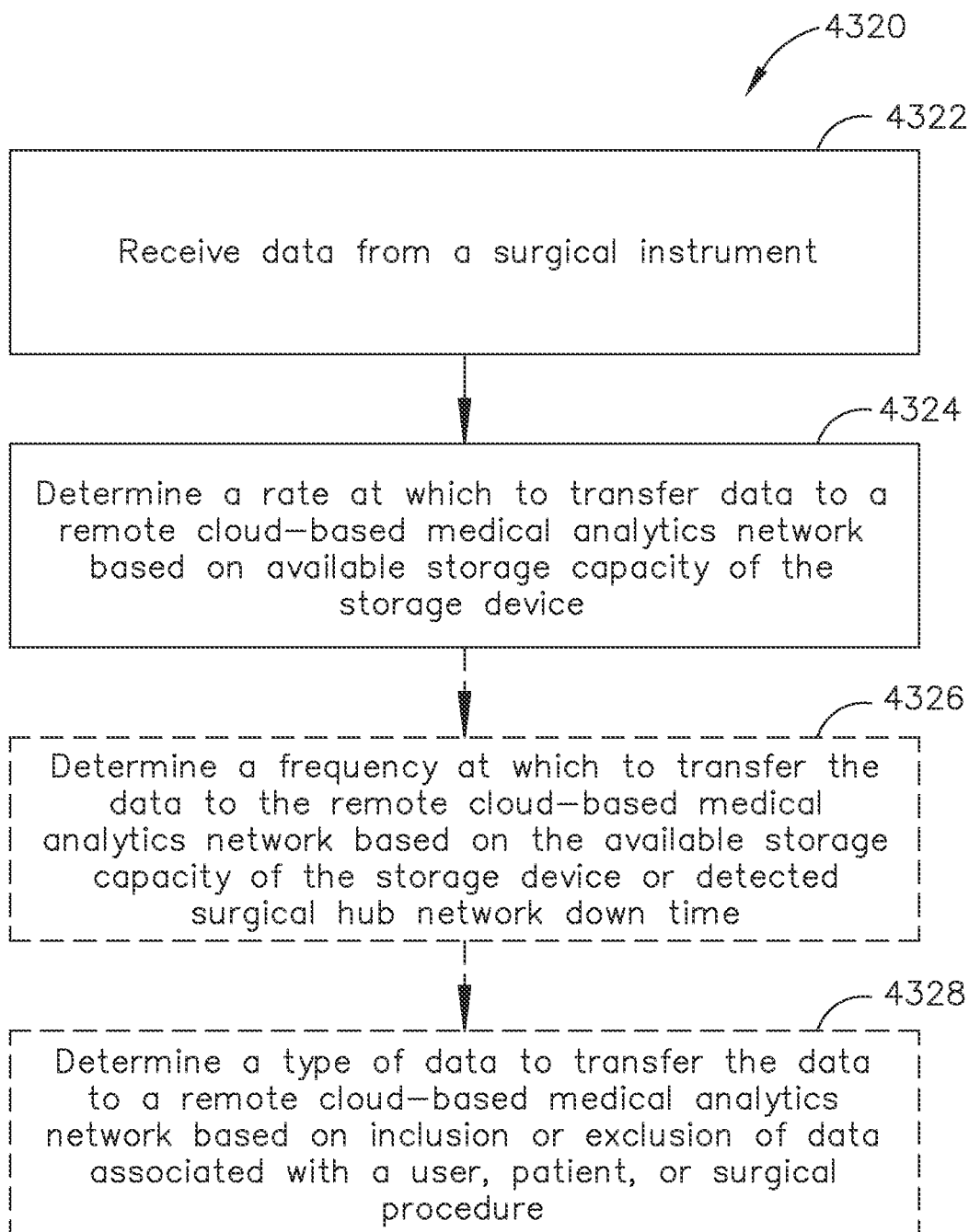
FIG. 40 is a logic flow diagram of a process depicting a control program or a logic configuration for determining rate, frequency, and type of data to transfer to a remote cloud-based analytics network, in accordance with at least one aspect of the present disclosure.

FIG. 40 is a logic flow diagram 4320 of a process depicting a control program or a logic configuration for determining rate, frequency, and type of data to transfer to a remote cloud-based analytics network, according to one aspect of the present disclosure. With reference to FIGS. 1-40, in one aspect, the present disclosure provides a surgical hub 206 comprising a storage device 248, a processor 244 coupled to the storage device 248, and a memory 249 coupled to the processor 244. The memory 249 stores instructions executable by the processor 244 to receive 4322 data from a surgical instrument 235, determine 4324 a rate at which to transfer the data to a remote cloud-based medical analytics network 204 based on available storage capacity of the storage device 248. Optionally, the memory 249 stores instructions executable by the processor 244 to determine 4326 a frequency at which to transfer the data to the remote cloud-based medical analytics network 204 based on the available storage capacity of the storage device 248. Optionally, the memory 249 stores instructions executable by the processor 244 to detect surgical hub network downtime and to determine 4326 a frequency at which to transfer the data to the remote cloud-based medical analytics network 204 based on the detected surgical hub network 206 down time. Optionally, the memory 249 stores instructions executable by the processor 244 to determine 4328 a type of data to transfer the data to a remote cloud-based medical analytics network 204 based on inclusion or exclusion of data associated with a users, patient, or surgical procedure.

In another aspect, the memory 249 stores instructions executable by the processor 244 to receive new operational parameters for the surgical hub 206 or the surgical instrument 235.

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

Figure 41:
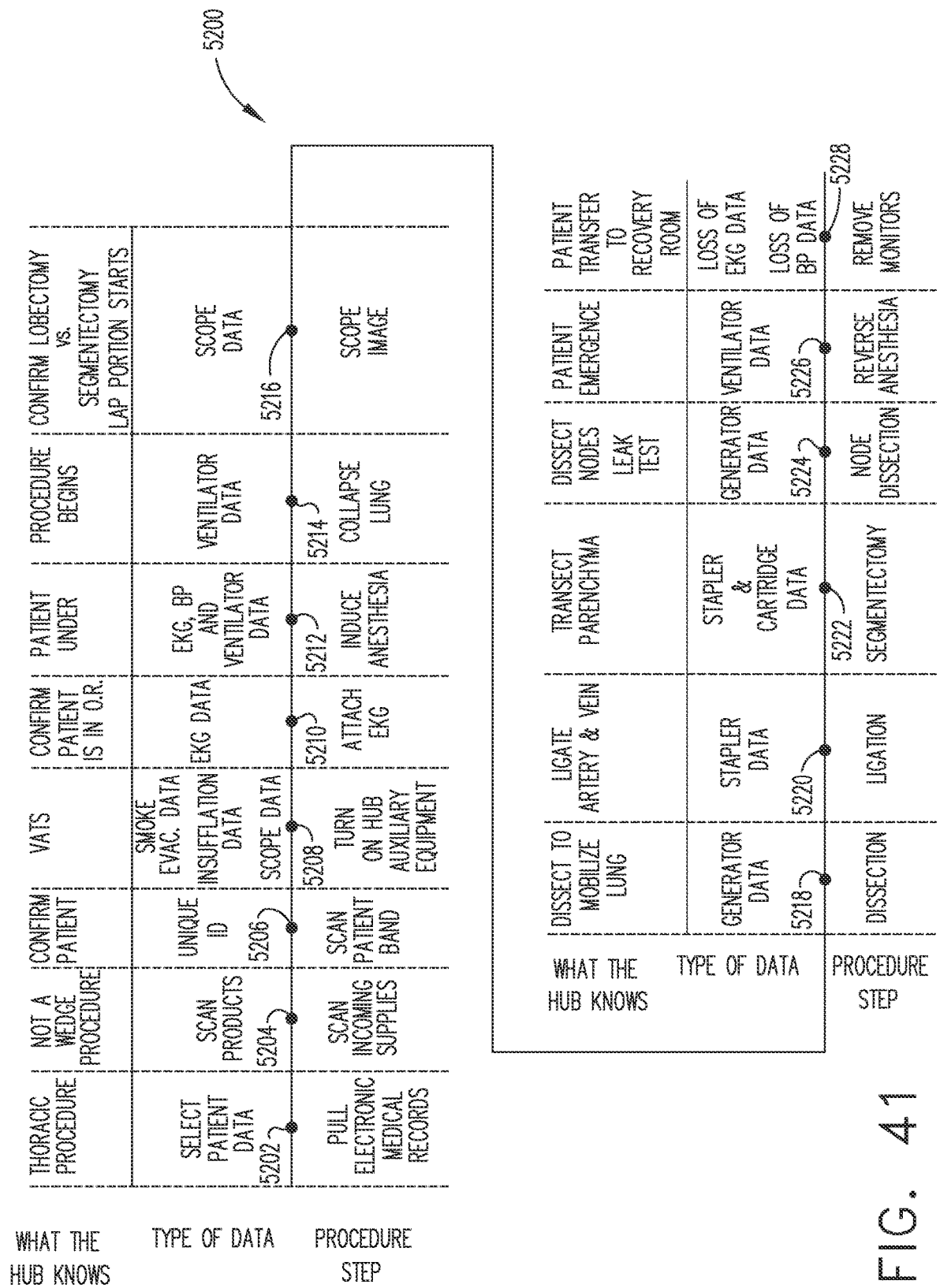
FIG. 41 is a timeline depicting situational awareness of a surgical hub, in accordance with at least one aspect of the present disclosure.

Referring now to FIG. 41, a timeline 5200 depicting situational awareness of a hub, such as the surgical hub 106 or 206, for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 5202 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 5204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 5206, the medical personnel scan the patient band via a scanner that is communicably connected to the surgical hub 106, 206. The surgical hub 106, 206 can then confirm the patient's identity based on the scanned data.

Fourth step 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 5210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 5212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 5212, the pre-operative portion of the lung segmentectomy procedure is completed and the operative portion begins.

Seventh step 5214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 5216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 5218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 5220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 5222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 5224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 5224, the incisions are closed up and the post-operative portion of the procedure begins.

Thirteenth step 5226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 5228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

Situational awareness is further described in U.S. Provisional Patent Application Ser. No. 62/611,341, titled INTERACTIVE SURGICAL PLATFORM, filed Dec. 28, 2017, which is incorporated by reference herein in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 102.

In one aspect, the present disclosure provides a surgical hub, comprising: a processor; and a memory coupled to the processor, the memory storing instructions executable by the processor to: interrogate a surgical instrument, wherein the surgical instrument is a first source of patient data; retrieve a first data set from the surgical instrument, wherein the first data set is associated with a patient and a surgical procedure; interrogate a medical imaging device, wherein the medical imaging device is a second source of patient data; retrieve a second data set from the medical imaging device, wherein the second data set is associated with the patient and an outcome of the surgical procedure; associate the first and second data sets by a key; and transmit the associated first and second data sets to remote network outside of the surgical hub. The present disclosure further provides, a surgical hub wherein the memory stores instructions executable by the processor to: retrieve the first data set using the key; anonymize the first data set by removing its association with the patient; retrieve the second data set using the key; anonymize the second data set by removing its association with the patient; pair the anonymized first and second data sets; and determine success rates of surgical procedures grouped by the surgical procedure based on the anonymized paired first and second data sets. The present disclosure further provides a surgical hub, wherein the memory stores instructions executable by the processor to: retrieve the anonymized first data set; retrieve the anonymized second data set; and reintegrate the anonymized first and second data sets using the key. The present disclosure further provides a surgical hub, wherein the first and second data sets define first and second data payloads in respective first and second data packets. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub, comprising: a processor; and a memory coupled to the processor, the memory storing instructions executable by the processor to: receive a first data packet from a first source, the first data packet comprising a first preamble, a first data payload, a source of the first data payload, and a first encryption certificate, wherein the first preamble defines the first data payload and the first encryption certificate verifies the authenticity of the first data packet; receive a second data packet from a second source, the second data packet comprising a second preamble, a second data payload, a source of the second data payload, and a second encryption certificate, wherein the second preamble defines the second data payload and the second encryption certificate verifies the authenticity of the second data packet; associate the first and second data packets; and generate a third data packet comprising the first and second data payloads. The present disclosure further provides a surgical hub, wherein the memory stores instructions executable by the processor to: determine that a data payload is from a new source; verify the new source of the data payload; and alter a data collection process at the surgical hub to receive subsequent data packets from the new source. The present disclosure further provides a surgical, wherein the memory stores instructions executable by the processor to associate the first and second data packets based on a key. The present disclosure further provides a surgical hub, wherein the memory stores instructions executable by the processor to anonymize the data payload of the third data packet. The present disclosure further provides a surgical hub, wherein the memory stores instructions executable by the processor to receive an anonymized third data packet and reintegrate the anonymized third data packet into the first and second data packets using the key. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub configured to communicate with a surgical instrument, the surgical hub comprising: a processor; and a memory coupled to the processor, the memory storing instructions executable by the processor to: receive a first data set associated with a surgical procedure, wherein the first data set is generated at a first time; receive a second data set associated with the efficacy of the surgical procedure, wherein the second data set is generated at a second time, wherein the second time is separate and distinct from the first time; anonymize the first and second data sets by removing information that identifies a patient, a surgery, or a scheduled time of the surgery; and store the first and second anonymized data sets to generate a data pair grouped by surgery. The present disclosure further provides a surgical hub, wherein the memory stores instructions executable by the processor to reconstruct a series of chronological events based on the data pair. The present disclosure further provides a surgical hub, wherein the memory stores instructions executable by the processor to reconstruct a series of coupled but unconstrained data sets based on the data pair. The present disclosure further provides a surgical hub, wherein the memory stores instructions executable by the processor to: encrypt the data pair; define a backup format for the data pair; and mirror the data pair to a cloud storage device. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub comprising: a storage device; a processor coupled to the storage device; and a memory coupled to the processor, the memory storing instructions executable by the processor to: receive data from a surgical instrument; determine a rate at which to transfer the data to a remote cloud-based medical analytics network based on available storage capacity of the storage device; determine a frequency at which to transfer the data to the remote cloud-based medical analytics network based on the available storage capacity of the storage device or detected surgical hub network down time; and determine a type of data to transfer the data to a remote cloud-based medical analytics network based on inclusion or exclusion of data associated with a users, patient, or surgical procedure. The present disclosure further provides a surgical hub, wherein the memory stores instructions executable by the processor to receive new operational parameters for the surgical hub or the surgical instrument. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub comprising: a control configured to: receive data from a surgical instrument; determine a rate at which to transfer the data to a remote cloud-based medical analytics network based on available storage capacity of the storage device; determine a frequency at which to transfer the data to the remote cloud-based medical analytics network based on the available storage capacity of the storage device or detected surgical hub network down time; and determine a type of data to transfer the data to a remote cloud-based medical analytics network based on inclusion or exclusion of data associated with a users, patient, or surgical procedure.

Various aspects of the subject matter described herein are set out in the following numbered examples.

Example 1. A surgical hub, comprising: a processor; a memory coupled to the processor, the memory storing instructions executable by the processor to: interrogate a modular device coupled to the processor via a modular communication hub, wherein the modular device is a source of data sets that include patient identity data and surgical procedure data; receive a data set from the modular device; discard the patient identity data and any portion of the surgical procedure data that identifies the patient from the data set; extract anonymous data from the data set and create an anonymized data set; and configure operation of the surgical hub or the modular device based on the anonymized data set.

Example 2. The surgical hub of Example 1, wherein the anonymized data set includes catastrophic failure of a modular device, and wherein the memory stores instructions executable by the processor to initiate automatic archive and submission of data for implications analysis based on the catastrophic failure of the modular device.

Example 3. The surgical hub of any one of Examples 1-2, wherein the memory stores instructions executable by the processor to detect counterfeit component information from the anonymized data set.

Example 4. The surgical hub of any one of Examples 1-3, wherein the memory stores instructions executable by the processor to derive implications of the modular device from the anonymized data set.

Example 5. The surgical hub of any one of Examples 1-4, wherein the memory stores instructions executable by the processor to configure the modular device to operate based on the derived implications.

Example 6. The surgical hub of any one of Examples 1-5, wherein the memory stores instructions executable by the processor to configure the surgical hub based on the derived implications.

Example 7. The surgical hub of any one of Examples 1-6, wherein the memory stores instructions executable by the processor to conglomerate the anonymized data.

Example 8. The surgical hub of any one of Examples 1-7, wherein the memory stores instructions executable by the processor to extract the anonymized data prior to storing the received data in a storage device coupled to the surgical hub.

Example 9. The surgical hub of any one of Examples 1-8, wherein the memory stores instructions executable by the processor to: transmit the anonymized data to a remote network outside of the surgical hub; compile the anonymized data at the remote network; and store a copy of the data set from the modular device in a patient electronic medical records database.

Example 10. The surgical hub of any one of Examples 1-9, comprising a modular communication hub coupled to the processor, the modular communication hub configured to connect modular devices located in one or more operating theaters to the surgical hub.

Example 11. A method of stripping data originating from a modular device coupled to a surgical hub by a communication hub, the surgical hub comprising a processor and a memory coupled to the processor, the memory storing instructions executable by the processor, the method comprising: interrogating, by a processor, a modular device coupled to the processor via a modular communication hub, wherein the modular communication hub is configured to connect modular devices located in one or more operating theaters to a surgical hub, wherein the modular device is a source of data sets that include patient identity data and surgical procedure data; receiving, by the processor, a data set from the modular device by the processor via the communication hub; discarding, by the processor, the patient identity data and any portion of the surgical procedure data that identifies the patient from the data set; extracting, by the processor, anonymous data from the data set and create an anonymized data set; and configuring, by the processor, operation of the surgical hub or the modular device based on the anonymized data set.

Example 12. The method of Example 11, comprising: initiating, by the processor, automatic archive and submission of data for implications analysis based on the catastrophic failure of the modular device wherein the anonymized data set includes catastrophic failure of a modular device.

Example 13. The method of any one of Examples 11-12, comprising by the processor, detecting counterfeit component information from the anonymized data set.

Example 14. The method of any one of Examples 11-13, comprising deriving implications of the modular device from the anonymized data set.

Example 15. The method of Example 14, comprising configuring, by the processor, the modular device to operate based on the derived implications.

Example 16. The method of any one of Examples 14-15, comprising configuring, by the processor, the surgical hub based on the derived implications.

Example 17. The method of any one of Examples 14-16, comprising, conglomerating by the processor, the anonymized data.

Example 18. The method of Example 11, extracting, by the processor, the anonymized data prior to storing the received data in a storage device coupled to the surgical hub.

Example 19. The method of Example 11, comprising: transmitting, by the processor, the anonymized data to a remote network outside of the surgical hub; compiling, by a server at the remote network, the anonymized data at the remote network; and storing, by the processor, a copy of the data set from the modular device in a patient electronic medical records database.

Example 20. A non-transitory computer readable medium storing computer readable instructions which, when executed, causes a machine to: interrogate a modular device coupled to the processor via the modular communication hub, wherein the modular device is a source of data sets that include patient identity data and surgical procedure data; receive a data set from the modular device; discard the patient identity data and any portion of the surgical procedure data that identifies the patient from the data set; extract anonymous data from the data set and create an anonymized data set; and configure operation of the surgical hub or the modular device based on the anonymized data set.

Example 21. The non-transitory computer readable medium of Example 20, storing computer readable instructions which, when executed, causes a machine to derive implications of the modular device from the anonymized data set.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A surgical system configured to enhance a patient's privacy during a surgical procedure, the surgical system comprising:

a surgical instrument configured for use during the surgical procedure;
a database configured to store a medical record associated with the patient; and
a surgical hub configured to be communicably coupled to the surgical instrument and the database, wherein the surgical hub comprises a memory and a control circuit configured to:
receive the medical record from the database;
determine that the medical record comprises medical information and personal information associated with the patient;
remove the medical information from the medical record;
generate an anonymous data file that exclusively comprises the medical information;
generate a recommended action for the surgical instrument based, at least in part, on the anonymous data file;
temporarily store the personal information in the memory;
generate a reassembled data file comprising the personal information temporarily stored in the memory and the medical information; and
delete the personal information temporarily stored in the memory of the surgical hub.

2. The surgical system of claim 1, wherein the database is further configured to store a key that uniquely identifies the medical record, wherein the control circuit is further configured to receive the key from the database, and wherein the generation of the reassembled data file is based, at least in part, on the key.

3. The surgical system of claim 1, wherein the control circuit is further configured to:
receive a signal from the surgical instrument, wherein the signal is associated with information generated by the surgical instrument during the surgical procedure;
determine that the information generated by the surgical instrument during the surgical procedure comprises personal patient information and medical patient information associated with the patient based, at least in part, on the received signal;
remove the medical patient information generated by the surgical instrument during the surgical procedure from the personal patient information generated by the surgical instrument during the surgical procedure; and
modify the anonymous data file to further comprise the medical patient information generated by the surgical instrument during the surgical procedure.

4. The surgical system of claim 3, wherein the medical patient information generated by the surgical instrument comprises a surgical outcome.

5. The surgical system of claim 4, further comprising a cloud-based analytics subsystem configured to analyze surgical outcome data, wherein the control circuit is further configured to transmit the anonymous data file to the cloud-based analytics subsystem.

6. The surgical system of claim 5, wherein the cloud-based analytics subsystem is separated from the surgical hub and the database by a hospital data barrier, and wherein data located outside the hospital data barrier exclusively comprises medical information associated with the patient to maintain anonymity.

7. The surgical system of claim 6, wherein the database is further configured to store a key that uniquely identifies the medical record, wherein the control circuit is further configured to access the medical record, and wherein accessing the medical record is based, at least in part, on the key.

8. The surgical system of claim 7, wherein the memory is configured to locally store the key in an encrypted format.

9. The surgical system of claim 1, wherein the recommended action comprises a suggested configuration for the surgical instrument.

10. The surgical system of claim 1, wherein the recommended action comprises a suggested operation for the surgical instrument.

11. The surgical system of claim 1, wherein the medical information comprises at least one of: a diagnosis associated with the patient, a pre-operative treatment associated with the patient, or a patient parameter that alone cannot be used to ascertain an identity of the patient, or combinations thereof.

12. The surgical system of claim 1, wherein the personal information comprises at least one of: an age of the patient, an employer of the patient, a body mass index of the patient, or a patient parameter that alone can be used to ascertain an identity of the patient, or combinations thereof.

13. A surgical hub configured to enhance a patient's privacy during a surgical procedure, wherein the surgical hub is configured to be communicably coupled to a surgical instrument and a database configured to store a medical record associated with the patient, the surgical hub comprising:
a memory; and
a control circuit configured to:
receive the medical record from the database;
determine that the medical record comprises medical information and personal information associated with the patient;
remove the medical information from the medical record;
generate an anonymous data file that exclusively comprises the medical information;
generate a recommended action for the surgical instrument based, at least in part, on the anonymous data file;
temporarily store the personal information in the memory;
generate a reassembled data file comprising the personal information temporarily stored in the memory and the medical information; and
delete the personal information temporarily stored in the memory of the surgical hub.

14. The surgical hub of claim 13, wherein the control circuit is further configured to:
receive a signal from the surgical instrument, wherein the signal is associated with information generated by the surgical instrument during the surgical procedure;
determine that the information generated by the surgical instrument during the surgical procedure comprises personal patient information and medical patient information associated with the patient based, at least in part, on the received signal;
remove the medical patient information generated by the surgical instrument during the surgical procedure from the personal patient information generated by the surgical instrument during the surgical procedure; and
modify the anonymous data file to further comprise the medical patient information generated by the surgical instrument during the surgical procedure.

15. The surgical hub of claim 13, further comprising a cloud-based analytics subsystem configured to analyze surgical outcome data, wherein the control circuit is further configured to transmit the anonymous data file to the cloud-based analytics subsystem.

16. The surgical hub of claim 15, wherein the cloud-based analytics subsystem is separated from the surgical hub by a hospital data barrier, and wherein data located outside the hospital data barrier exclusively comprises medical information associated with the patient to maintain anonymity.

17. A method of enhancing a patient's privacy during a surgical procedure, wherein data external to a data barrier is anonymous, and wherein the surgical procedure comprises a surgical hub configured to be communicably coupled to a database configured to store a medical record and a surgical instrument, the method comprising:
  retrieving a medical record from the database;
  determining that the medical record comprises medical information and personal information associated with the patient;
  removing the medical information from the medical record;
  generating an anonymous data file that exclusively comprises the medical information;
  generating a recommended action for the surgical instrument based, at least in part, on the anonymous data file;
  storing, temporarily, the personal information in the surgical hub;
  generating a reassembled data file comprising the personal information temporarily stored in the surgical hub and the medical information; and
  deleting the personal information temporarily stored in the surgical hub.

18. The method of claim 17, further comprising:
  receiving a signal from the surgical instrument, wherein the signal is associated with information generated by the surgical instrument during the surgical procedure;
  determining that the information generated by the surgical instrument during the surgical procedure comprises personal patient information and medical patient information associated with the patient based, at least in part, on the received signal;
  removing the medical patient information generated by the surgical instrument during the surgical procedure from the personal patient information generated by the surgical instrument during the surgical procedure; and
  modifying the anonymous data file to further comprise the medical patient information generated by the surgical instrument during the surgical procedure.

* * * * *